(12) United States Patent
Strube et al.

(10) Patent No.: US 10,182,949 B2
(45) Date of Patent: Jan. 22, 2019

(54) NONWOVEN MATERIAL HAVING DISCRETE THREE-DIMENSIONAL DEFORMATIONS WITH WIDE BASE OPENINGS THAT ARE BASE BONDED TO ADDITIONAL LAYER

(71) Applicant: The Procter & Gamble Company, Cincinnati, OH (US)

(72) Inventors: John Brian Strube, Okeana, OH (US); Jill Marlene Orr, Liberty Township, OH (US); James Terry Knapmeyer, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 14/844,603

(22) Filed: Sep. 3, 2015

(65) Prior Publication Data

US 2016/0074251 A1 Mar. 17, 2016

Related U.S. Application Data

(60) Provisional application No. 62/049,376, filed on Sep. 12, 2014.

(51) Int. Cl.
*A61F 13/511* (2006.01)
*A61F 13/513* (2006.01)
(Continued)

(52) U.S. Cl.
CPC .. *A61F 13/51104* (2013.01); *A61F 13/15577* (2013.01); *A61F 13/15699* (2013.01);
(Continued)

(58) Field of Classification Search
CPC .. B32B 3/28; B32B 3/30; B32B 5/022; B32B 5/06; B32B 2555/02; B32B 5/142;
(Continued)

(56) References Cited

U.S. PATENT DOCUMENTS

| 4,041,951 A | 8/1977 | Sanford |
| 4,323,068 A | 4/1982 | Aziz |

(Continued)

FOREIGN PATENT DOCUMENTS

| CA | 2518857 | 11/2004 |
| EP | 1283028 A2 | 2/2003 |

(Continued)

OTHER PUBLICATIONS

Translation of WO 2012/176656; published Dec. 27, 2012.*
(Continued)

*Primary Examiner* — Catherine A. Simone
(74) *Attorney, Agent, or Firm* — Christian M. Best

(57) ABSTRACT

A composite sheet that includes a first sheet and a second sheet is disclosed. The first and second sheets are bonded to each other at a number of spaced apart discrete inter-sheet bond locations. The first sheet is a nonwoven material that has discrete three-dimensional deformations therein forming protrusions that extend outward from the first surface of the first sheet to their distal ends and wide base openings adjacent to the second surface of the first sheet. The second sheet is a generally planar sheet that contacts the distal ends of the protrusions on the first sheet. The second sheet is bonded to the first sheet at spaced apart inter-sheet bond locations where the first region of the first sheet contacts the second sheet.

18 Claims, 32 Drawing Sheets

(51) Int. Cl.
   *B23B 3/28*     (2006.01)
   *B23B 3/30*     (2006.01)
   *B23B 5/04*     (2006.01)
   *B23B 5/06*     (2006.01)
   *B23B 5/02*     (2006.01)
   *B23B 5/14*     (2006.01)
   *D04H 13/00*    (2006.01)
   *A61F 13/15*    (2006.01)
   *B32B 5/26*     (2006.01)
   *B32B 5/02*     (2006.01)
   *B32B 5/06*     (2006.01)
   *B32B 5/08*     (2006.01)
   *B32B 5/14*     (2006.01)
   *B32B 5/22*     (2006.01)
   *B32B 3/28*     (2006.01)
   *B32B 3/30*     (2006.01)
   *D04H 1/74*     (2006.01)
   *D04H 1/559*    (2012.01)
   *A61F 13/51*    (2006.01)

(52) U.S. Cl.
   CPC .... *A61F 13/5116* (2013.01); *A61F 13/51108* (2013.01); *A61F 13/51121* (2013.01); *A61F 13/51394* (2013.01); *B32B 3/28* (2013.01); *B32B 3/30* (2013.01); *B32B 5/022* (2013.01); *B32B 5/06* (2013.01); *B32B 5/08* (2013.01); *B32B 5/142* (2013.01); *B32B 5/22* (2013.01); *B32B 5/26* (2013.01); *D04H 1/559* (2013.01); *D04H 1/74* (2013.01); *D04H 13/00* (2013.01); *D04H 13/001* (2013.01); *A61F 2013/51007* (2013.01); *A61F 2013/51014* (2013.01); *A61F 2013/51186* (2013.01); *B32B 2262/02* (2013.01); *B32B 2262/0253* (2013.01); *B32B 2262/0261* (2013.01); *B32B 2262/0276* (2013.01); *B32B 2262/04* (2013.01); *B32B 2262/06* (2013.01); *B32B 2262/062* (2013.01); *B32B 2262/08* (2013.01); *B32B 2262/12* (2013.01); *B32B 2262/14* (2013.01); *B32B 2307/726* (2013.01); *B32B 2555/00* (2013.01); *B32B 2555/02* (2013.01); *D10B 2403/0111* (2013.01); *D10B 2509/02* (2013.01)

(58) Field of Classification Search
   CPC ..... B32B 5/22; B32B 5/26; B32B 5/08; A61F 13/51104; A61F 13/5116; A61F 13/511; A61F 13/51108; A61F 13/15699; A61F 13/512; A61F 13/51121; A61F 13/51394; D04H 13/00; D04H 13/001; D04H 1/74; D04H 1/495; D04H 1/498; D04H 1/492; Y10T 428/24479; Y10T 428/24612; Y10T 428/24636
   USPC ........................................................ 428/198
   See application file for complete search history.

(56) References Cited

U.S. PATENT DOCUMENTS

| | | |
|---|---|---|
| 4,333,979 A | 6/1982 | Sciaraffa et al. |
| 4,846,821 A * | 7/1989 | Lyons ............... A61F 13/51476 428/152 |
| 4,921,034 A | 5/1990 | Burgess et al. |
| 5,036,758 A | 8/1991 | Kobayashi et al. |
| 5,518,801 A | 5/1996 | Chappell et al. |
| 5,599,335 A | 2/1997 | Goldman et al. |
| 5,628,097 A | 5/1997 | Benson et al. |
| 5,804,021 A | 9/1998 | Abuto et al. |
| 5,888,607 A | 3/1999 | Seth et al. |
| 5,938,650 A | 8/1999 | Baer et al. |
| 5,972,477 A | 10/1999 | Kim et al. |
| 6,080,276 A | 6/2000 | Burgess |
| 6,136,124 A | 10/2000 | Wagner |
| 6,228,462 B1 | 5/2001 | Yee et al. |
| 6,274,218 B1 | 8/2001 | Shimizu |
| 6,344,102 B1 | 2/2002 | Wagner |
| 6,344,111 B1 | 2/2002 | Wilhelm |
| 6,368,444 B1 | 4/2002 | Jameson et al. |
| 6,395,957 B1 | 5/2002 | Chen et al. |
| 6,440,564 B1 | 8/2002 | McLain et al. |
| 6,610,904 B1 | 8/2003 | Thomas |
| 6,641,902 B1 | 11/2003 | Kobayashi et al. |
| 6,685,686 B2 | 2/2004 | Hermansson et al. |
| 6,700,036 B2 | 3/2004 | Thomas et al. |
| 6,733,626 B2 | 5/2004 | Ruthven et al. |
| 6,739,024 B1 | 5/2004 | Wagner |
| 6,818,802 B2 | 11/2004 | Takai et al. |
| 6,867,156 B1 | 3/2005 | White et al. |
| 6,887,349 B2 | 5/2005 | Ruthven et al. |
| 6,888,046 B2 | 5/2005 | Toyoshima et al. |
| 7,037,406 B2 | 5/2006 | Kershaw et al. |
| 7,060,344 B2 | 6/2006 | Pourdeyhimi et al. |
| 7,172,801 B2 | 2/2007 | Hoying et al. |
| 7,182,838 B2 | 2/2007 | Ruthven et al. |
| 7,267,860 B2 | 9/2007 | Toyoshima et al. |
| 7,294,231 B2 | 11/2007 | Kershaw et al. |
| 7,297,226 B2 | 11/2007 | Schulz |
| 7,326,322 B2 | 2/2008 | Ruthven et al. |
| 7,410,683 B2 | 8/2008 | Gray et al. |
| 7,435,313 B2 | 10/2008 | Boatman et al. |
| 7,468,114 B2 | 12/2008 | Sato et al. |
| 7,531,062 B2 | 5/2009 | Kershaw et al. |
| 7,553,532 B2 | 6/2009 | Gray et al. |
| 7,648,752 B2 | 1/2010 | Gray et al. |
| 7,678,034 B2 | 3/2010 | Wilhelm |
| 7,682,686 B2 | 3/2010 | Gray et al. |
| 7,687,679 B2 | 3/2010 | Mishima |
| 7,799,176 B2 | 9/2010 | Wilhelm |
| 7,842,849 B2 | 11/2010 | Datta |
| 7,857,941 B2 | 12/2010 | Ruthven et al. |
| 7,951,127 B2 | 5/2011 | Sanabria et al. |
| 7,971,526 B2 | 7/2011 | Blenke et al. |
| 8,142,617 B2 | 3/2012 | Ruthven et al. |
| D662,326 S | 6/2012 | Shanbhag et al. |
| 8,231,377 B2 | 7/2012 | Wittner et al. |
| 8,241,543 B2 | 8/2012 | O'Donnell et al. |
| 8,287,694 B2 | 10/2012 | Schulz |
| 8,304,600 B2 | 11/2012 | Noda et al. |
| 8,313,473 B2 | 11/2012 | Nada |
| D672,152 S | 12/2012 | Shanbhag et al. |
| 8,393,374 B2 | 3/2013 | Sato et al. |
| 8,535,481 B2 | 9/2013 | Schulz |
| 8,574,209 B2 | 11/2013 | Nishitani et al. |
| 8,585,958 B2 | 11/2013 | Gray et al. |
| 8,617,449 B2 | 12/2013 | Baker et al. |
| 8,865,965 B2 | 10/2014 | Sato et al. |
| 8,877,316 B2 | 11/2014 | Hasenoehrl et al. |
| 9,067,357 B2 | 6/2015 | Orr et al. |
| 9,108,355 B2 | 8/2015 | Kume et al. |
| 9,566,761 B2 | 2/2017 | Mitsuno et al. |
| 9,579,924 B2 | 2/2017 | Boegli |
| 2002/0004654 A1 | 1/2002 | Daniels et al. |
| 2003/0195487 A1 | 10/2003 | Thomas |
| 2003/0211802 A1 | 11/2003 | Keck et al. |
| 2004/0002688 A1 | 1/2004 | Thomas et al. |
| 2004/0140047 A1 | 7/2004 | Sato et al. |
| 2004/0229008 A1 | 11/2004 | Hoying |
| 2004/0265534 A1 | 12/2004 | Curro et al. |
| 2005/0008825 A1 | 1/2005 | Casey et al. |
| 2005/0281976 A1 | 12/2005 | Curro |
| 2006/0111684 A1 | 5/2006 | Berba et al. |
| 2006/0194027 A1 | 8/2006 | Pourdeyhimi et al. |
| 2006/0286343 A1 | 12/2006 | Gray et al. |
| 2007/0049153 A1 | 3/2007 | Dunbar et al. |
| 2007/0212966 A1 | 9/2007 | Abed et al. |
| 2008/0221538 A1 | 9/2008 | Zhao et al. |
| 2008/0227356 A1 | 9/2008 | Porouthoor et al. |
| 2009/0030390 A1 | 1/2009 | Hammons et al. |

(56) References Cited

U.S. PATENT DOCUMENTS

| | | |
|---|---|---|
| 2010/0028621 A1 | 2/2010 | Byrne et al. |
| 2010/0035014 A1 | 2/2010 | Hammons et al. |
| 2010/0036338 A1 | 2/2010 | Hammons et al. |
| 2010/0209664 A1* | 8/2010 | Sato .................. B32B 3/266 428/138 |
| 2010/0233438 A1 | 9/2010 | Stone et al. |
| 2010/0247844 A1 | 9/2010 | Curro et al. |
| 2010/0249740 A1 | 9/2010 | Miyamoto et al. |
| 2010/0297377 A1 | 11/2010 | Buscher et al. |
| 2010/0310810 A1 | 12/2010 | Bond et al. |
| 2011/0073513 A1 | 3/2011 | Weisman et al. |
| 2011/0094669 A1 | 4/2011 | Oetjen |
| 2011/0125120 A1 | 5/2011 | Nishitani et al. |
| 2011/0260371 A1 | 10/2011 | Arora et al. |
| 2011/0302733 A1 | 12/2011 | Yuan |
| 2012/0059343 A1 | 3/2012 | Kume et al. |
| 2012/0064280 A1 | 3/2012 | Hammons et al. |
| 2012/0064298 A1 | 3/2012 | Curro et al. |
| 2012/0136329 A1 | 5/2012 | Carney |
| 2012/0234475 A1 | 9/2012 | Paldey |
| 2012/0238984 A1 | 9/2012 | Paldey |
| 2013/0165883 A1 | 6/2013 | Kimura et al. |
| 2013/0309439 A1 | 11/2013 | Close et al. |
| 2014/0023822 A1 | 1/2014 | Tai et al. |
| 2014/0039434 A1 | 2/2014 | Xu et al. |
| 2014/0052088 A1 | 2/2014 | Weisman et al. |
| 2014/0054827 A1 | 2/2014 | Mullane et al. |
| 2014/0121621 A1 | 5/2014 | Biggs et al. |
| 2014/0121623 A1 | 5/2014 | Biggs et al. |
| 2014/0121624 A1 | 5/2014 | Biggs et al. |
| 2014/0121625 A1 | 5/2014 | Biggs et al. |
| 2014/0121626 A1 | 5/2014 | Finn et al. |
| 2014/0163500 A1 | 6/2014 | Roe et al. |
| 2014/0163501 A1 | 6/2014 | Ehrnsperger et al. |
| 2014/0170367 A1 | 6/2014 | Turner et al. |
| 2014/0234575 A1 | 8/2014 | Mitsuno et al. |
| 2014/0276517 A1 | 9/2014 | Chester et al. |
| 2014/0367290 A1 | 12/2014 | Nomoto et al. |
| 2015/0059599 A1 | 3/2015 | Boegli |
| 2015/0073366 A1 | 3/2015 | Ehrnsperger et al. |
| 2015/0080826 A1 | 3/2015 | Ehrnsperger et al. |
| 2015/0182386 A1 | 7/2015 | Nakakado |
| 2015/0250660 A1 | 9/2015 | Tally et al. |
| 2015/0283003 A1 | 10/2015 | Rosati et al. |
| 2016/0067118 A1 | 3/2016 | Hammons et al. |
| 2016/0074237 A1 | 3/2016 | Rosati et al. |
| 2016/0074257 A1 | 3/2016 | Orr et al. |
| 2016/0220421 A1 | 8/2016 | Kuramochi |
| 2017/0258645 A1 | 9/2017 | Orr et al. |
| 2017/0258650 A1 | 9/2017 | Rosati et al. |
| 2017/0259524 A1 | 9/2017 | Neton et al. |
| 2017/0259550 A1 | 9/2017 | Neton et al. |

FOREIGN PATENT DOCUMENTS

| | | |
|---|---|---|
| EP | 861646 | 5/2003 |
| EP | 1208828 B1 | 7/2005 |
| EP | 1184075 B1 | 1/2007 |
| EP | 1842513 | 10/2007 |
| EP | 1787611 B1 | 9/2011 |
| EP | 2554730 | 2/2013 |
| EP | 1982013 B1 | 6/2013 |
| EP | 1774940 B1 | 9/2013 |
| EP | 2437708 B1 | 9/2013 |
| EP | 2277485 B1 | 5/2014 |
| JP | A-H06-169948 | 6/1994 |
| JP | 02055058 | 5/1996 |
| JP | A-H11-286863 | 10/1999 |
| JP | 3124190 | 1/2001 |
| JP | 2003116909 | 4/2003 |
| JP | A-2006-297076 | 11/2006 |
| JP | 2006341455 A | 12/2006 |
| JP | 3868880 | 1/2007 |
| JP | 3880502 | 2/2007 |
| JP | 2008073396 | 4/2008 |
| JP | A-2008-245959 | 10/2008 |
| JP | 4184253 | 11/2008 |
| JP | A-2009-089965 | 4/2009 |
| JP | 4282428 B2 | 6/2009 |
| JP | 2009153731 A | 7/2009 |
| JP | 2009172354 A | 8/2009 |
| JP | 2011200446 | 10/2011 |
| JP | 2012010884 | 1/2012 |
| JP | 4901425 | 3/2012 |
| JP | 4931580 | 5/2012 |
| JP | 4974524 | 7/2012 |
| JP | 5074174 | 11/2012 |
| JP | 5099752 B2 | 12/2012 |
| JP | 5103100 | 12/2012 |
| JP | 5148182 | 2/2013 |
| JP | 2013074978 | 4/2013 |
| JP | 2013126455 | 6/2013 |
| JP | 5268416 | 8/2013 |
| JP | 2013169388 | 9/2013 |
| JP | A-2013-176895 | 9/2013 |
| JP | 5319367 | 10/2013 |
| JP | A-2014-018647 | 2/2014 |
| JP | A-2014-034145 | 2/2014 |
| JP | A-2014-083228 | 5/2014 |
| JP | A-2014-110890 | 6/2014 |
| WO | WO 9301781 | 2/1993 |
| WO | WO9403677 | 2/1994 |
| WO | WO 9827904 | 7/1998 |
| WO | WO 200029199 | 5/2000 |
| WO | WO 2000/38604 | 7/2000 |
| WO | WO 200174281 | 10/2001 |
| WO | WO200224133 | 3/2002 |
| WO | WO 200429349 | 4/2004 |
| WO | WO 2004058214 A1 | 7/2004 |
| WO | WO 2004098869 | 11/2004 |
| WO | WO 2006007149 | 1/2006 |
| WO | WO 2006009997 A2 | 1/2006 |
| WO | WO 2007001270 A1 | 1/2007 |
| WO | WO 2007116944 | 10/2007 |
| WO | WO 2008146594 A1 | 12/2008 |
| WO | WO 2009139255 | 11/2009 |
| WO | WO 201074205 | 7/2010 |
| WO | WO 2010118272 | 10/2010 |
| WO | WO 2011142272 | 11/2011 |
| WO | WO 2012176656 | 12/2012 |
| WO | WO 2013047890 | 4/2013 |
| WO | WO 201377074 | 5/2013 |
| WO | WO 2013099463 | 7/2013 |
| WO | WO 2013147222 | 10/2013 |
| WO | WO 2013175360 | 11/2013 |
| WO | WO 2014084066 A1 | 6/2014 |
| WO | WO 201545842 | 4/2015 |
| WO | WO2015157254 A1 | 10/2015 |
| WO | WO2016040104 | 3/2016 |

OTHER PUBLICATIONS

U.S. Appl. No. 14/844,459, filed Sep. 3, 2015, John Brian Strube et al.

U.S. Appl. No. 14/844,499, filed Sep. 3, 2015, Jill Marlene Orr et al.

U.S. Appl. No. 14/844,526, filed Sep. 3, 2015, Jill Marlene Orr et al.

U.S. Appl. No. 14/844,457, filed Sep. 3, 2015, John Brian Strube et al.

U.S. Appl. No. 14/844,482, filed Sep. 3, 2015, John Brian Strube et al.

U.S. Appl. No. 14/844,507, filed Sep. 3, 2015, John Brian Strube et al.

U.S. Appl. No. 14/844,523, filed Sep. 3, 2015, John Brian Strube et al.

U.S. Appl. No. 14/844,582, filed Sep. 3, 2015, John Brian Strube et al.

U.S. Appl. No. 14/844,591, filed Sep. 3, 2015, John Brian Strube et al.

U.S. Appl. No. 14/844,613, filed Sep. 3, 2015, John Brian Strube et al.

(56) References Cited

OTHER PUBLICATIONS

U.S. Appl. No. 14/844,018, filed Sep. 3, 2015, Jill Marlene Orr et al.
U.S. Appl. No. 14/844,026, filed Sep. 3, 2015, Jill Marlene Orr et al.
U.S. Appl. No. 14/844,033, filed Sep. 3, 2015, Rodrigo Rosati et al.
U.S. Appl. No. 14/844,037, filed Sep. 3, 2015, Rodrigo Rosati et al.
U.S. Appl. No. 14/844,043, filed Sep. 3, 2015, Rodrigo Rosati et al.
U.S. Appl. No. 14/844,047, filed Sep. 3, 2015, Rodrigo Rosati et al.
U.S. Appl. No. 14/844,272, filed Sep. 3, 2015, Rodrigo Rosati et al.
U.S. Appl. No. 14/844,343, filed Sep. 3, 2015, Rodrigo Rosati et al.
U.S. Appl. No. 14/844,358, filed Sep. 3, 2015, Rodrigo Rosati et al.
U.S. Appl. No. 14/844,374, filed Sep. 3, 2015, Rodrigo Rosati et al.
U.S. Appl. No. 14/844,385, filed Sep. 3, 2015, Rodrigo Rosati et al.
U.S. Appl. No. 14/844,402, filed Sep. 3, 2015, Rodrigo Rosati et al.
U.S. Appl. No. 14/844,411, filed Sep. 3, 2015, Rodrigo Rosati et al.
U.S. Appl. No. 14/844,256, filed Sep. 3, 2015, Rodrigo Rosati et al.
U.S. Appl. No. 14/844,269, filed Sep. 3, 2015, Rodrigo Rosati et al.
International Search Report and Written Opinion dated Nov. 3, 2015, U.S. Appl. No. 14/844,459, 10 pgs.
International Search Report and Written Opinion dated Nov. 5, 2015, U.S. Appl. No. 14/844,499, 11 pgs.
International Search Report and Written Opinion dated Nov. 18, 2015, U.S. Appl. No. 14/844,526, 12 pgs.
International Search Report and Written Opinion dated Nov. 9, 2015, U.S. Appl. No. 14/844,457, 11 pgs.
International Search Report and Written Opinion dated Dec. 3, 2015, U.S. Appl. No. 14/844,018, 15 pgs.
International Search Report and Written Opinion dated Nov. 23, 2015, U.S. Appl. No. 14/844,482, 13 pgs.
International Search Report and Written Opinion dated Nov. 13, 2015, U.S. Appl. No. 14/844,507, 13 pgs.
International Search Report and Written Opinion dated Dec. 1, 2015, U.S. Appl. No. 14/844,523, 11 pgs.
International Search Report and Written Opinion dated Nov. 9, 2015, U.S. Appl. No. 14/844,543, 12 pgs.
International Search Report and Written Opinion dated Dec. 11, 2015, U.S. Appl. No. 14/844,582, 10 pgs.
International Search Report and Written Opinion dated Nov. 13, 2015, U.S. Appl. No. 14/844,591, 13 pgs.
International Search Report and Written Opinion dated Dec. 3, 2015, U.S. Appl. No. 14/844,603, 10 pgs.
International Search Report and Written Opinion dated Nov. 20, 2015, U.S. Appl. No. 14/844,613, 13 pgs.
All Office Actions for U.S. Appl. No. 14/844,026.
All Office Actions for U.S. Appl. No. 14/844,033.
All Office Actions for U.S. Appl. No. 14/844,037.
All Office Actions for U.S. Appl. No. 14/844,043.
All Office Actions for U.S. Appl. No. 14/844,047.
All Office Actions for U.S. Appl. No. 14/844,292.
All Office Actions for U.S. Appl. No. 14/844,343.
All Office Actions for U.S. Appl. No. 14/844,358.
All Office Actions for U.S. Appl. No. 14/844,374.
All Office Actions for U.S. Appl. No. 14/844,385.
All Office Actions for U.S. Appl. No. 14/844,402.
All Office Actions for U.S. Appl. No. 14/844,411.
All Office Actions for U.S. Appl. No. 14/844,256.
All Office Actions for U.S. Appl. No. 14/844,269.
All Office Actions for U.S. Appl. No. 14/844,459.
All Office Actions for U.S. Appl. No. 14/844,499.
All Office Actions for U.S. Appl. No. 14/844,526.
All Office Actions for U.S. Appl. No. 14/844,457.
All Office Actions for U.S. Appl. No. 14/844,507.
All Office Actions for U.S. Appl. No. 14/844,523.
All Office Actions for U.S. Appl. No. 14/844,543.
All Office Actions for U.S. Appl. No. 14/844,582.
All Office Actions for U.S. Appl. No. 14/844,591.
All Office Actions for U.S. Appl. No. 14/844,603.
All Office Actions for U.S. Appl. No. 14/844,613.

* cited by examiner

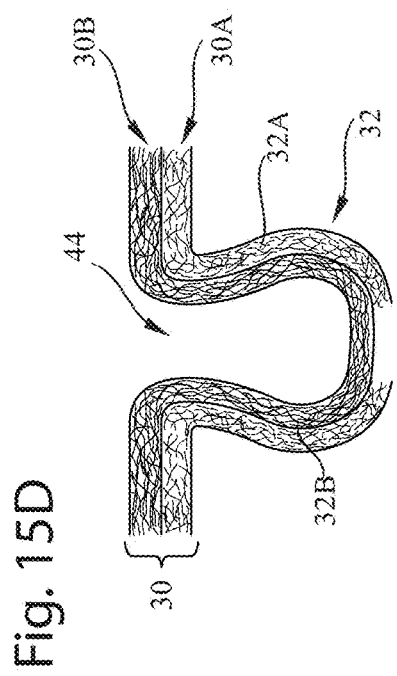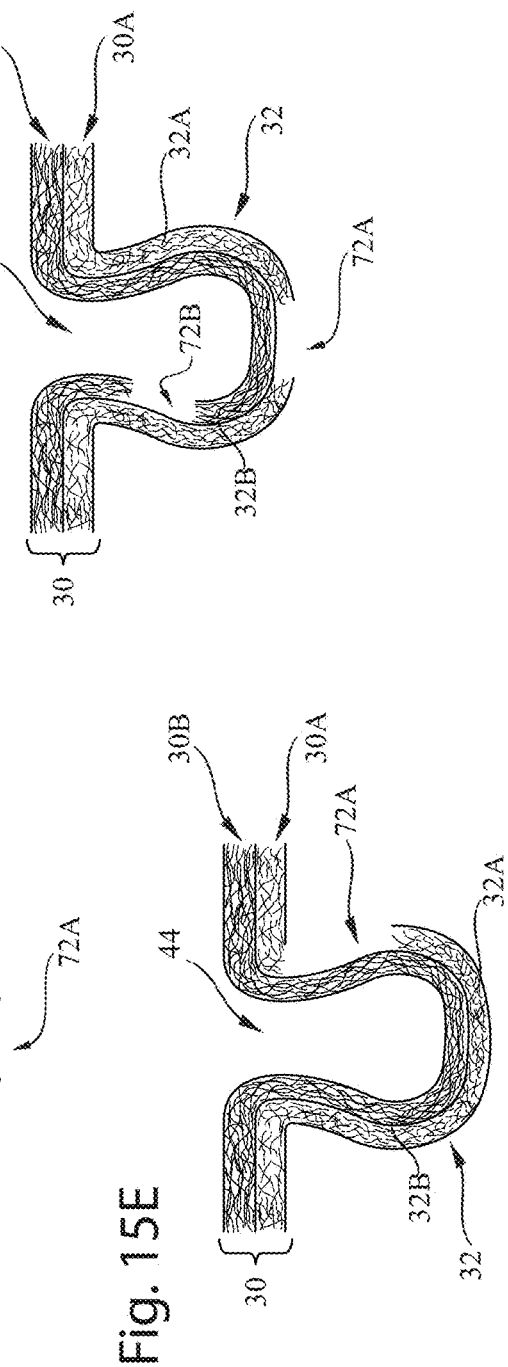

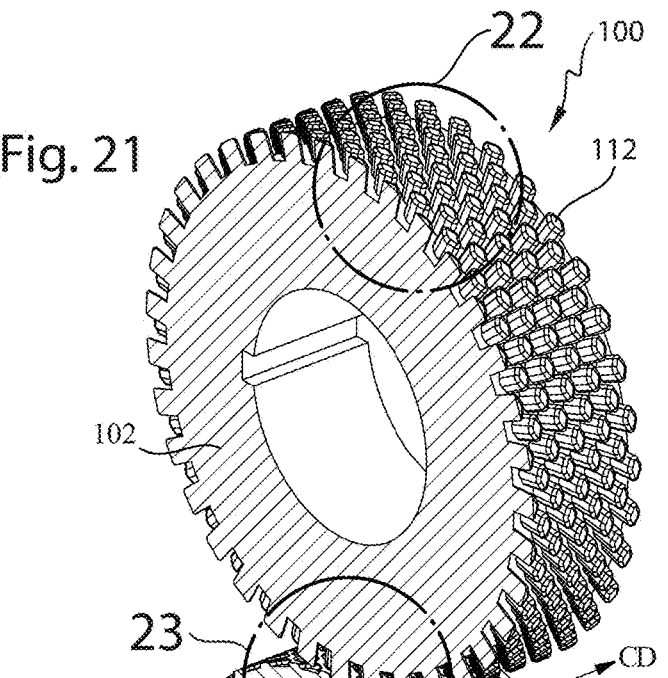
Fig. 21
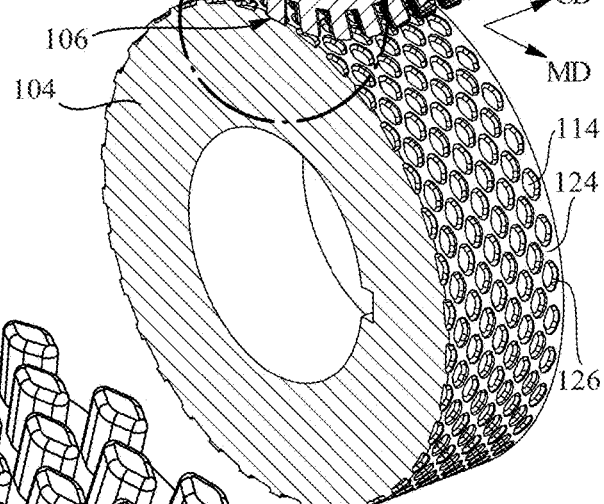
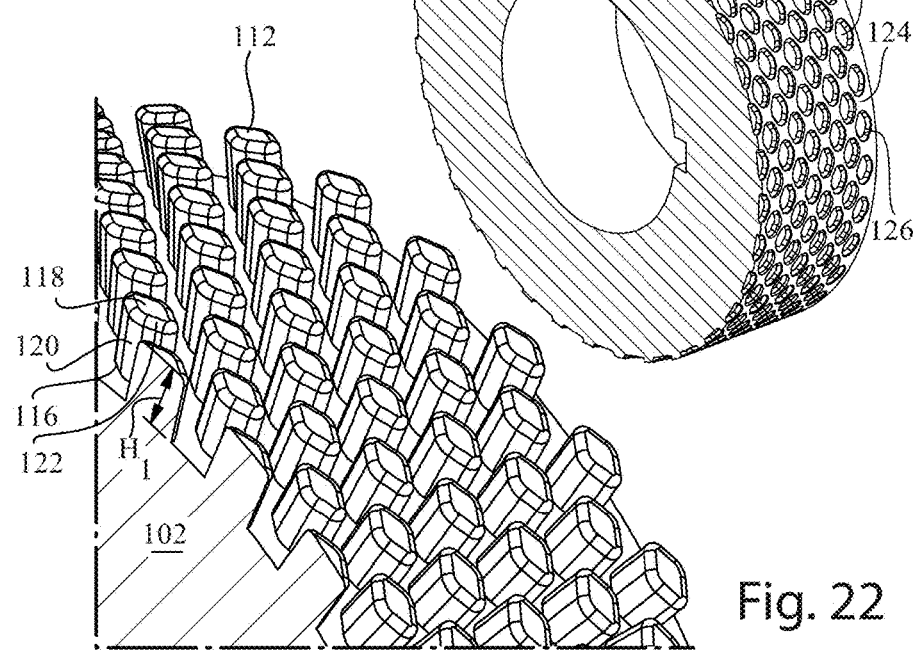
Fig. 22

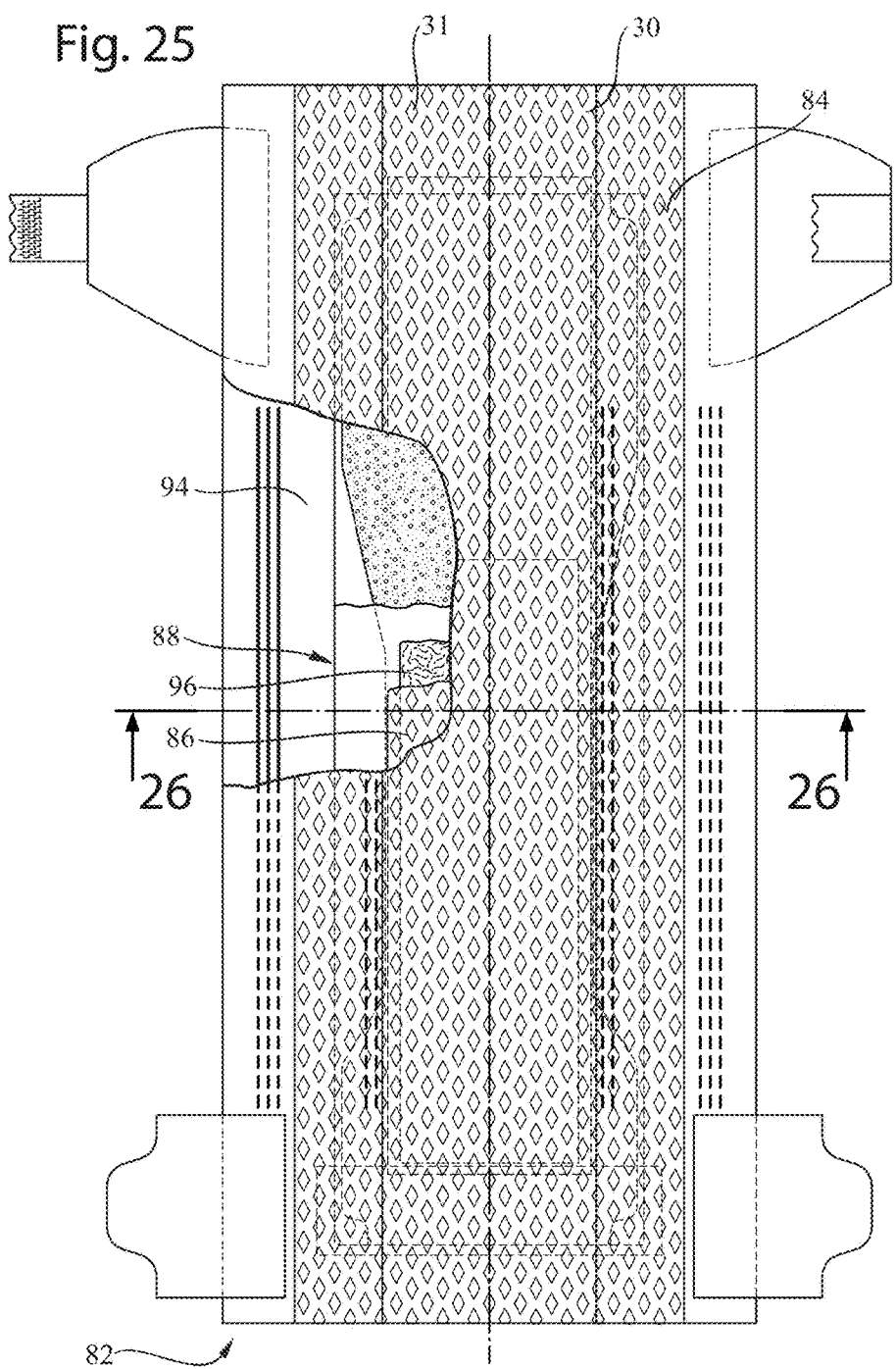

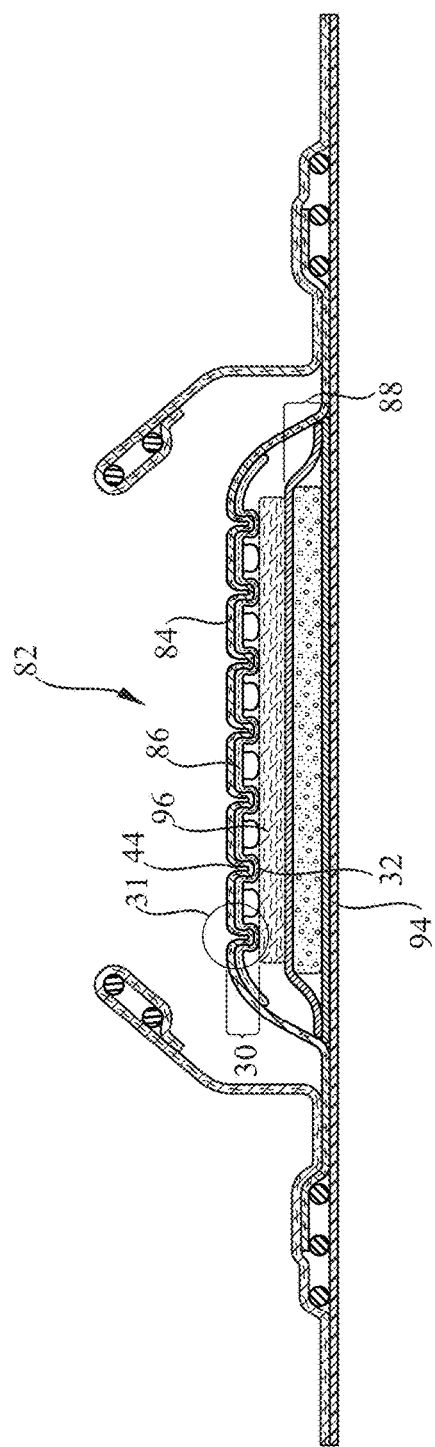

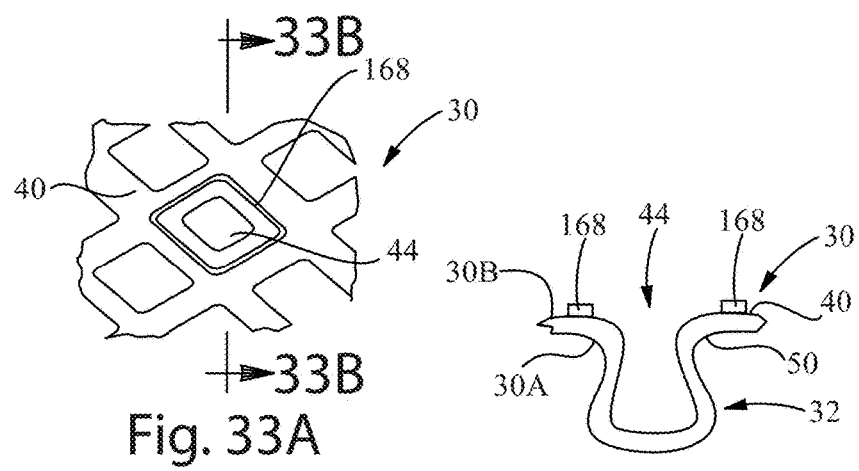
Fig. 33A
Fig. 33B
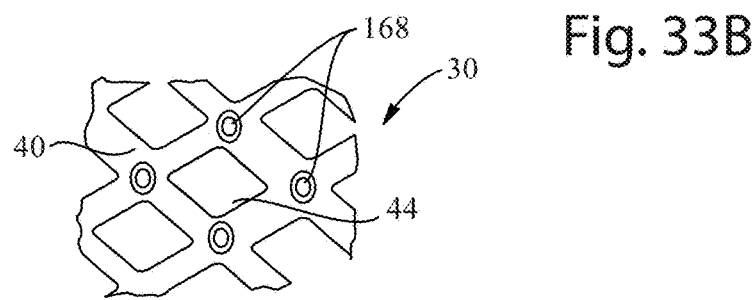
Fig. 34
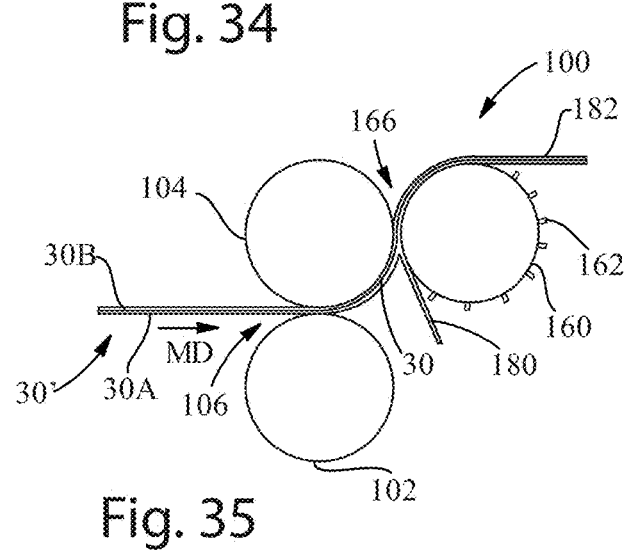
Fig. 35

NONWOVEN MATERIAL HAVING DISCRETE THREE-DIMENSIONAL DEFORMATIONS WITH WIDE BASE OPENINGS THAT ARE BASE BONDED TO ADDITIONAL LAYER

FIELD OF THE INVENTION

The present invention is directed to nonwoven materials having discrete three-dimensional deformations with wide base openings, methods of making the same, and articles including such nonwoven materials.

BACKGROUND

Various materials for use in absorbent articles are disclosed in the patent literature. Patent publications disclosing such materials and methods for making the same include: U.S. Pat. No. 4,323,068, Aziz; U.S. Pat. No. 5,518,801, Chappell, et al.; U.S. Pat. No. 5,628,097, Benson, et al.; U.S. Pat. No. 5,804,021, Abuto, et al.; U.S. Pat. No. 6,440,564 B1, McLain, et al.; U.S. Pat. No. 7,172,801, Hoying, et al.; U.S. Pat. No. 7,410,683, Curro, et al.; U.S. Pat. No. 7,553,532, Turner, et al.; U.S. Pat. No. 7,648,752 B2, Hoying, et al.; U.S. Pat. No. 7,682,686 B2, Curro, et al.; U.S. Pat. No. 8,241,543 B2, O'Donnell, et al.; U.S. Pat. No. 8,393,374 B2, Sato, et al.; U.S. Pat. No. 8,585,958 B2, Gray, et al.; U.S. Pat. No. 8,617,449 B2, Baker, et al.; U.S. Patent Application Publications US 2006/0286343 A1; US 2010/0028621 A1; US 2010/0297377 A1; US 2012/0064298 A1; US 2013/0165883 A1; US 2014/0121621 A1; US 2014/0121623 A1; US 2014/0121624 A1; US 2014/0121625 A1; US 2014/0121626 A1; EP 1774940 B1; EP 1787611 B1; EP 1982013 B1; PCT WO 2008/146594 A1; and WO 2014/084066 A1 (Zuiko). Kao MERRIES™ diapers and Kimberly-Clark HUGGIES® diapers have premium products in which a textured topsheet is bonded to another non-textured layer via heated embossing or hydroentangling.

A need exists for improved materials for use in absorbent articles, and methods of making such materials. In certain cases, a need exists for improved nonwoven materials or laminates of nonwoven materials that look and feel soft, and have improved dryness. In particular, a need exists for improved nonwoven materials having three-dimensional features formed therein to provide improved softness and dryness, as well as a visual signal of softness and dryness. The three dimensional features may form depressions on one side of the material and protrusions on the opposing side. In some cases, it may be desirable to place such materials in an absorbent article so that the depressions are visible on the topsheet of the absorbent article. In some of such cases, it is desirable for such depressions to be well-defined and have a wide opening formed thereby so that they may not only improve liquid acquisition, but may also provide a "signal" to the consumer of the liquid acquisition properties of an absorbent article and ability to handle viscous fluids such as bowel movements. It becomes increasingly more difficult to form three-dimensional features that remain well-defined when making such materials at high line speeds. In addition, in the event that the material is incorporated into a product (such as a disposable diaper) that is made or packaged under compression, it becomes difficult to preserve the three-dimensional character of the features/deformations after the material is subjected to such compressive forces. Certain prior three dimensional structures have a tendency to collapse or close and become much less visible after compression. Further, a need exists for materials that can be provided with such properties using mechanical deformation methods, which are less costly than higher energy processes such as hydroentangling and hydro-molding.

Therefore, a need exists for such materials and high speed, relatively inexpensive methods of making the same that have deformations therein that provide well-defined three-dimensional features, even after being compressed. A specific facet of high speed is the compatibility with manufacturing lines for absorbent articles, which offers the advantages of pattern flexibility and zoning, and reduces the need to ship bulky materials.

SUMMARY

The present invention is directed to nonwoven materials having discrete three-dimensional deformations with wide base openings, methods of making the same, and articles including such nonwoven materials.

The nonwoven materials have deformations formed therein. The deformations form protrusions that extend outward from the first surface of the nonwoven material and a base opening inside the narrowest portion of the protrusion adjacent the second surface of the nonwoven material. The protrusions may comprise a cap portion. The maximum interior width of the cap portion of the protrusions may be wider than the width of the base opening. The protrusions may comprise fibers that extend from the base of the protrusion to the distal end of the protrusions that contribute to form a portion of the sides and cap of the protrusion. In some cases, multiple such fibers may be disposed substantially completely around the sides of the protrusions. In some cases, when compressive forces are applied on the nonwoven web, at least some of the protrusions may be configured to collapse in a controlled manner such that the base opening may remain open. In some cases, the width of the protrusions may vary along the length of the protrusions. In some cases, the nonwoven material comprises at least two layers, and the layers may differ in the concentration of fibers and/or the presence of thermal point bonds at various locations in and around the protrusions. In some cases, the deformations may have greater light transmission than the adjacent undeformed regions. Any of the properties described herein may be present in the nonwoven materials separately, or in any combination.

The method of forming deformations in a nonwoven material includes the steps of: a) providing at least one precursor nonwoven web; b) providing a pair of forming members which include: a first forming member having a surface comprising a plurality of discrete, spaced apart male forming elements; and a second forming member having a surface comprising a plurality of recesses in the second forming member, wherein the recesses are each aligned and configured to receive at least one of the male forming elements therein, wherein the recesses may have a plan view periphery that is larger than, and may completely surround, the plan view periphery of the male elements; and c) placing the precursor nonwoven web between the forming members and mechanically deforming the precursor nonwoven web with the forming members. The method forms a nonwoven web having a generally planar first region and a plurality of discrete deformations. The deformations form protrusions that extend outward from the first surface of the nonwoven web and an opening in the second surface of the nonwoven web.

BRIEF DESCRIPTION OF THE DRAWINGS

FIG. 15D is a cross-sectional view taken along the transverse axis of a deformation of an alternative embodiment of a multi-layer nonwoven web shown with the base opening facing upward.

FIG. 15E is a cross-sectional view taken along the transverse axis of a deformation of an alternative embodiment of a multi-layer nonwoven web shown with the base opening facing upward.

FIG. 15F is a cross-sectional view taken along the transverse axis of a deformation of an alternative embodiment of a multi-layer nonwoven web shown with the base opening facing upward.

FIG. 21 is a perspective view of one example of an apparatus for forming the nonwoven material described herein.

FIG. 22 is an enlarged perspective view of a portion of the male roll shown in FIG. 21.

FIG. 25 is an absorbent article in the form of a diaper comprising an exemplary topsheet/acquisition layer composite structure wherein the length of the acquisition layer is less that the length of the topsheet with some layers partially removed.

FIG. 26 is one transverse cross-section of the diaper of FIG. 25 taken along line 26-26.

FIG. 33A is a plan view of a base bonded nonwoven made by the apparatus shown in FIG. 32 (shown with the base opening oriented upward).

FIG. 33B is a schematic cross-sectional view of the base bonded nonwoven shown in FIG. 33A taken along line 33B-33B.

FIG. 34 is a plan view photomicrograph showing the bonds formed by the apparatus shown in FIG. 32.

FIG. 35 is a schematic side view of an apparatus for base bonding the deformed nonwoven material to an additional layer.

Figure 1:
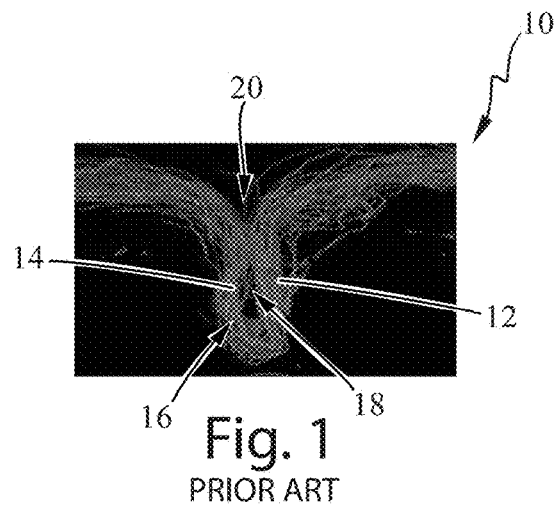
FIG. 1 is a photomicrograph showing the end view of a prior art tuft.

The embodiment(s) of the nonwoven material, the articles, the method and the apparatus(es) shown in the drawings are illustrative in nature and are not intended to be limiting of the invention defined by the claims. Moreover, the features of the invention will be more fully apparent and understood in view of the detailed description.

DETAILED DESCRIPTION

I. Definitions

The term "absorbent article" includes disposable articles such as sanitary napkins, panty liners, tampons, interlabial devices, wound dressings, diapers, adult incontinence articles, wipes, and the like. At least some of such absorbent articles are intended for the absorption of body liquids, such as menses or blood, vaginal discharges, urine, and feces. Wipes may be used to absorb body liquids, or may be used for other purposes, such as for cleaning surfaces. Various absorbent articles described above will typically comprise a liquid pervious topsheet, a liquid impervious backsheet joined to the topsheet, and an absorbent core between the topsheet and backsheet. The nonwoven material described herein can comprise at least part of other articles such as scouring pads, wet or dry-mop pads (such as SWIFFER® pads), and the like.

The term "absorbent core", as used herein, refers to the component of the absorbent article that is primarily responsible for storing liquids. As such, the absorbent core typically does not include the topsheet or backsheet of the absorbent article.

The term "aperture", as used herein, refers to a regular or substantially regularly-shaped hole that is intentionally formed and extends completely through a web or structure (that is, a through hole). The apertures can either be punched cleanly through the web so that the material surrounding the aperture lies in the same plane as the web prior to the formation of the aperture (a "two dimensional" aperture), or the holes can be formed such that at least some of the material surrounding the opening is pushed out of the plane of the web. In the latter case, the apertures may resemble a depression with an aperture therein, and may be referred to herein as a "three dimensional" aperture, a subset of apertures.

The term "component" of an absorbent article, as used herein, refers to an individual constituent of an absorbent article, such as a topsheet, acquisition layer, liquid handling layer, absorbent core or layers of absorbent cores, backsheets, and barriers such as barrier layers and barrier cuffs.

The term "cross-machine direction" or "CD" means the path that is perpendicular to the machine direction in the plane of the web.

The term "deformable material", as used herein, is a material which is capable of changing its shape or density in response to applied stresses or strains.

The term "discrete", as used herein, means distinct or unconnected. When the term "discrete" is used relative to forming elements on a forming member, it is meant that the distal (or radially outwardmost) ends of the forming elements are distinct or unconnected in all directions, including in the machine and cross-machine directions (even though bases of the forming elements may be formed into the same surface of a roll, for example).

The term "disposable" is used herein to describe absorbent articles and other products which are not intended to be laundered or otherwise restored or reused as an absorbent article or product (i.e., they are intended to be discarded after use and, preferably, to be recycled, composted or otherwise disposed of in an environmentally compatible manner).

The term "forming elements", as used herein, refers to any elements on the surface of a forming member that are capable of deforming a web.

The term "integral", as used herein as in "integral extension" when used to describe the protrusions, refers to fibers of the protrusions having originated from the fibers of the precursor web(s). Thus, as used herein, "integral" is to be distinguished from fibers introduced to or added to a separate precursor web for the purpose of making the protrusions.

The term "joined to" encompasses configurations in which an element is directly secured to another element by affixing the element directly to the other element; configurations in which the element is indirectly secured to the other element by affixing the element to intermediate member(s) which in turn are affixed to the other element; and configurations in which one element is integral with another element, i.e., one element is essentially part of the other element. The term "joined to" encompasses configurations in which an element is secured to another element at selected locations, as well as configurations in which an element is completely secured to another element across the entire surface of one of the elements. The term "joined to" includes any known manner in which elements can be secured including, but not limited to mechanical entanglement.

The term "machine direction" or "MD" means the path that material, such as a web, follows through a manufacturing process.

The term "macroscopic", as used herein, refers to structural features or elements that are readily visible and distinctly discernable to a human having 20/20 vision when the perpendicular distance between the viewer's eye and the web is about 12 inches (30 cm). Conversely, the term "microscopic" refers to such features that are not readily visible and distinctly discernable under such conditions.

The term "mechanically deforming", as used herein, refers to processes in which a mechanical force is exerted upon a material in order to permanently deform the material. The term "permanently deformed", as used herein, refers to the state of a deformable material whose shape or density has been permanently altered in response to applied stresses or strains.

The terms "SELF" and "SELF'ing", refer to Procter & Gamble technology in which SELF stands for Structural Elastic Like Film. While the process was originally developed for deforming polymer film to have beneficial structural characteristics, it has been found that the SELF'ing process can be used to produce beneficial structures in other materials. Processes, apparatuses, and patterns produced via SELF are illustrated and described in U.S. Pat. Nos. 5,518,801; 5,691,035; 5,723,087; 5,891,544; 5,916,663; 6,027,483; and 7,527,615 B2.

The term "tuft", as used herein, refers to a particular type of feature that may be formed from fibers in a nonwoven web. Tufts may have a tunnel-like configuration which may be open at both of their ends.

The term "web" is used herein to refer to a material whose primary dimension is X-Y, i.e., along its length (or longitudinal direction) and width (or transverse direction). It should be understood that the term "web" is not necessarily limited to single layers or sheets of material. Thus the web can comprise laminates or combinations of several sheets of the requisite type of materials.

The term "Z-dimension" refers to the dimension orthogonal to the length and width of the web or article. The Z-dimension usually corresponds to the thickness of the web or material. As used herein, the term "X-Y dimension" refers to the plane orthogonal to the thickness of the web or material. The X-Y dimension usually corresponds to the length and width, respectively, of the web or material.

II. Nonwoven Materials

The present invention is directed to nonwoven materials having discrete three-dimensional deformations, which deformations provide protrusions on one side of the material, and openings on the other side of the nonwoven materials. Methods of making the nonwoven materials are also disclosed. The nonwoven materials can be used in absorbent articles and other articles.

As used herein, the term "nonwoven" refers to a web or material having a structure of individual fibers or threads which are interlaid, but not in a repeating pattern as in a woven or knitted fabric, which latter types of fabrics do not typically have randomly oriented or substantially randomly-oriented fibers. Nonwoven webs will have a machine direction (MD) and a cross machine direction (CD) as is commonly known in the art of web manufacture. By "substantially randomly oriented" is meant that, due to processing conditions of the precursor web, there may be a higher amount of fibers oriented in the MD than the CD, or vice versa. For example, in spunbonding and meltblowing processes continuous strands of fibers are deposited on a support moving in the MD. Despite attempts to make the orientation of the fibers of the spunbond or meltblown nonwoven web truly "random," usually a slightly higher percentage of fibers are oriented in the MD as opposed to the CD.

Nonwoven webs and materials are often incorporated into products, such as absorbent articles, at high manufacturing line speeds. Such manufacturing processes can apply compressive and shear forces on the nonwoven webs that may damage certain types of three-dimensional features that have been purposefully formed in such webs. In addition, in the event that the nonwoven material is incorporated into a product (such as a disposable diaper) that is made or packaged under compression, it becomes difficult to preserve the three-dimensional character of some types of prior three-dimensional features after the material is subjected to such compressive forces.

Figure 2:
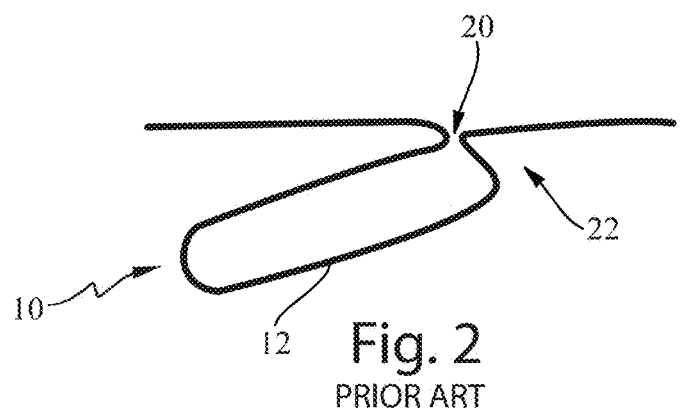
FIG. 2 is a schematic end view of a prior art tuft after it has been subjected to compression.

For instance, FIGS. 1 and 2 show an example of a prior art nonwoven material 10 with a tufted structure. The nonwoven material comprises tufts 12 formed from looped fibers 14 that form a tunnel-like structure having two ends 16. The tufts 12 extend outward from the plane of the nonwoven material in the Z-direction. The tunnel-like structure has a width that is substantially the same from one end of the tuft to the opposing end. Often, such tufted structures will have holes or openings 18 at both ends and an opening 20 at their base. Typically, the openings 18 at the ends of the tufts are at the machine direction (MD) ends of the tufts. The openings 18 at the ends of the tufts can be a result of the process used to form the tufts. If the tufts 12 are formed by forming elements in the form of teeth with a relatively small tip and vertical leading and trailing edges that form a sharp point, these leading and/or trailing edges may punch through the nonwoven web at least one of the ends of the tufts. As a result, openings 18 may be formed at one or both ends of the tufts 12.

Figure 3:
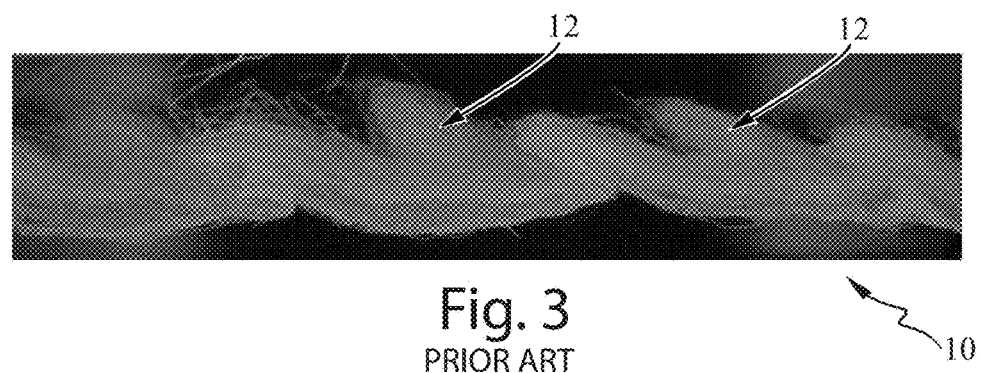
FIG. 3 is a photomicrograph of the end of a prior art nonwoven web showing a plurality of collapsed tufts.

While such a nonwoven material 10 provides well-defined tufts 12, the opening 20 at the base of the tuft structure can be relatively narrow and difficult to see with the naked eye. In addition, as shown in FIG. 2, the material of the tuft 12 surrounding this narrow base opening 20 may tend to form a hinge 22, or pivot point if forces are exerted on the tuft. If the nonwoven is compressed (such as in the Z-direction), in many cases, the tufts 12 can collapse to one side and close off the opening 20. Typically, a majority of the tufts in such a tufted material will collapse and close off the openings 20. FIG. 2 schematically shows an example of a tuft 12 after it has collapsed. In FIG. 2, the tuft 12 has folded over to the left side. FIG. 3 is an image showing a nonwoven material with several upwardly-oriented tufts, all of which have folded over to the side. However, not all of the tufts 12 will collapse and fold over to the same side. Often, some tufts 12 will fold to one side, and some tufts will fold to the other side. As a result of the collapse of the tufts 12, the openings 20 at the base of the tufts can close up, become slit-like, and virtually disappear.

Figure 4:
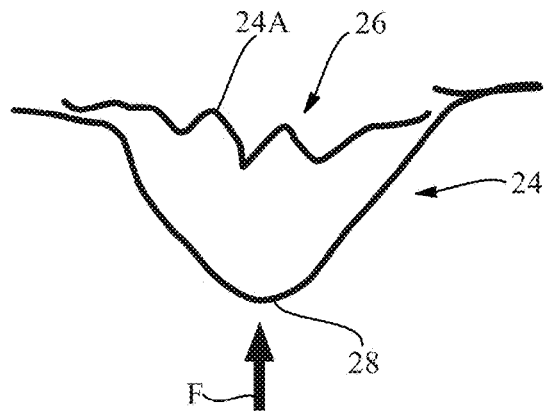
FIG. 4 is a schematic side view of a prior art conical-shaped structure before and after it has been subjected to compression.

Prior art nonwoven materials with certain other types of three dimensional deformations, such as conical structures, can also be subject to collapse when compressed. As shown in FIG. 4, conical structures 24 will not necessarily fold over as will certain tufted structures when subjected to compressive forces F. However, conical structures 24 can be subject to collapse in that their relatively wide base opening 26 and smaller tip 28 causes the conical structure to push back toward the plane of the nonwoven material, such as to the configuration designated 24A.

The nonwoven materials of at least some embodiments of the present invention described herein are intended to better preserve the structure of discrete three-dimensional features in the nonwoven materials after compression.

Figure 5:
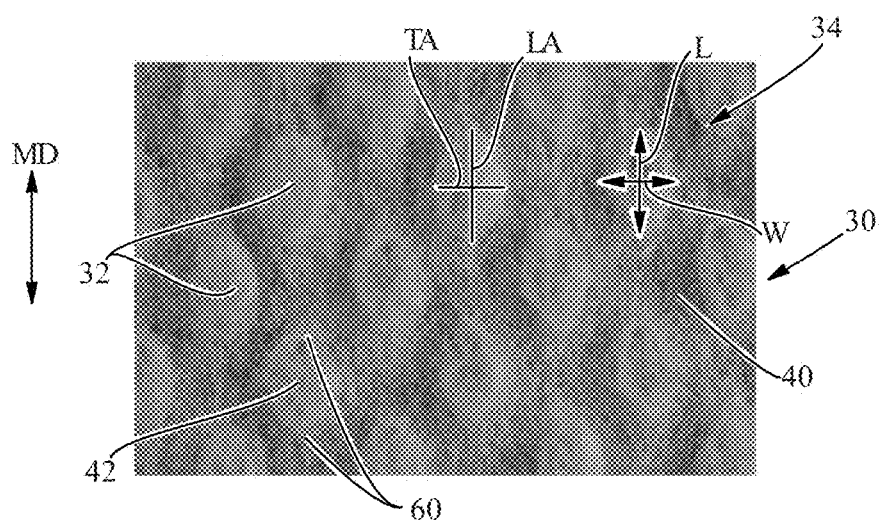
FIG. 5 is a plan view photomicrograph showing one side of the nonwoven material having three-dimensional deformations formed therein, with the protrusions oriented upward.
Figure 6:
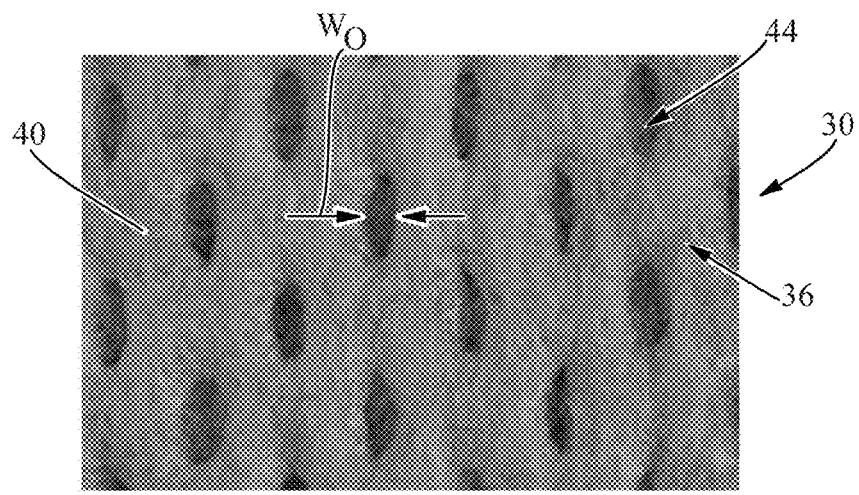
FIG. 6 is a plan view photomicrograph showing the other side of a nonwoven material similar to that shown in FIG. 5, with the openings in the nonwoven facing upward.
Figure 7:
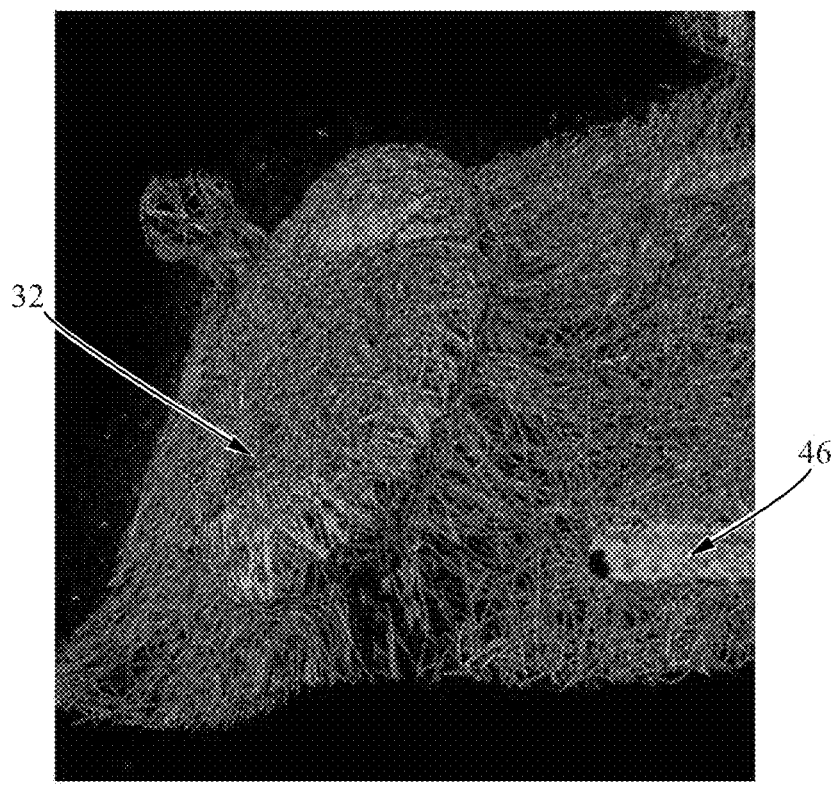
FIG. 7 is a Micro CT scan image showing a perspective view of a protrusion in a single layer nonwoven material.
Figure 8:
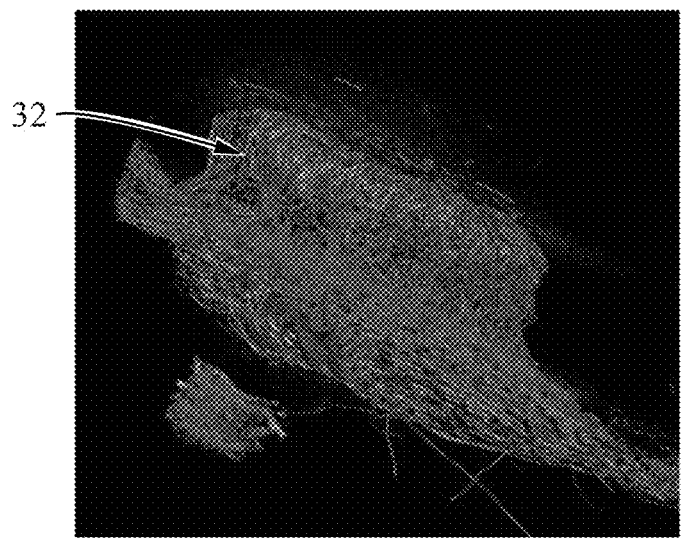
FIG. 8 is a Micro CT scan image showing a side of a protrusion in a single layer nonwoven material.
Figure 9:
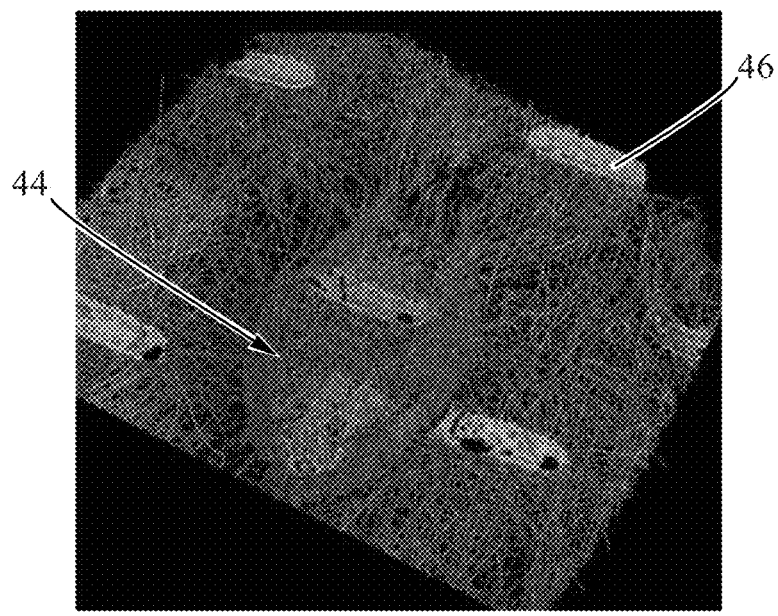
FIG. 9 is a Micro CT scan image showing a perspective view of a deformation with the opening facing upward in a single layer nonwoven material.

FIGS. 5-14 show examples of nonwoven materials 30 with three-dimensional deformations comprising protrusions 32 therein. The nonwoven materials 30 have a first surface 34, a second surface 36, and a thickness T therebetween (the thickness being shown in FIG. 12). FIG. 5 shows the first surface 34 of a nonwoven material 30 with the protrusions 32 that extend outward from the first surface 34 of the nonwoven material oriented upward. FIG. 6 shows the second surface 36 of a nonwoven material 30 such as that shown in FIG. 5, having three-dimensional deformations formed therein, with the protrusions oriented downward and the base openings 44 oriented upward. FIG. 7 is a Micro CT scan image showing a perspective view of a protrusion 32. FIG. 8 is a Micro CT scan image showing a side view of a protrusion 32 (of one of the longer sides of the protrusion). FIG. 9 is a Micro CT scan image showing a perspective view of a deformation with the opening 44 facing upward. The nonwoven materials 30 comprise a plurality of fibers 38 (shown in FIGS. 7-11 and 14). As shown in FIGS. 7 and 9, in some cases, the nonwoven material 30 may have a plurality of bonds 46 (such as thermal point bonds) therein to hold the fibers 38 together. Any such bonds 46 are typically present in the precursor material from which the nonwoven materials 30 are formed.

The protrusions 32 may, in some cases, be formed from looped fibers (which may be continuous) 38 that are pushed outward so that they extend out of the plane of the nonwoven web in the Z-direction. The protrusions 32 will typically comprise more than one looped fiber. In some cases, the protrusions 32 may be formed from looped fibers and at least some broken fibers. In addition, in the case of some types of nonwoven materials (such as carded materials, which are comprised of shorter fibers), the protrusions 32 may be formed from loops comprising multiple discontinuous fibers. Multiple discontinuous fibers in the form of a loop are shown as layer 30A in FIGS. 15A-15F. The looped fibers may be: aligned (that is, oriented in substantially the same direction); not be aligned; or, the fibers may be aligned in some locations within the protrusions 32, and not aligned in other parts of the protrusions.

In some cases, if male/female forming elements are used to form the protrusions 32, and the female forming elements substantially surround the male forming elements, the fibers in at least part of the protrusions 32 may remain substantially randomly oriented (rather than aligned), similar to their orientation in the precursor web(s). For example, in some cases, the fibers may remain substantially randomly oriented in the cap of the protrusions, but be more aligned in the side walls such that the fibers extend in the Z-direction from the base of the protrusions to the cap. In addition, if the precursor web comprises a multi-layer nonwoven material, the alignment of fibers can vary between layers, and can also vary between different portions of a given protrusion 32 within the same layer.

The nonwoven material 30 may comprise a generally planar first region 40 and the three-dimensional deformations may comprise a plurality of discrete integral second regions 42. The term "generally planar" is not meant to imply any particular flatness, smoothness, or dimensionality. Thus, the first region 40 can include other features that provide the first region 40 with a topography. Such other features can include, but are not limited to small projections, raised network regions around the base openings 44, and other types of features. Thus, the first region 40 is generally planar when considered relative to the second regions 42. The first region 40 can have any suitable plan view configuration. In some cases, the first region 40 is in the form of a continuous inter-connected network which comprises portions that surround each of the deformations.

Figure 10:
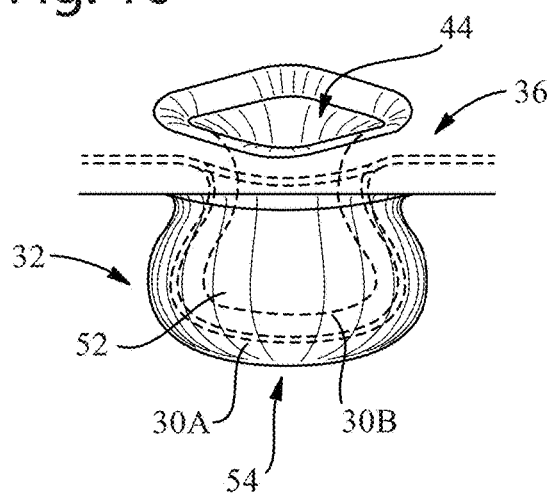
FIG. 10 is a perspective view of a deformation in a two layer nonwoven material with the opening facing upward.

The term "deformation", as used herein, includes both the protrusions 32 formed on one side of the nonwoven material and the base openings 44 formed in the opposing side of the material. The base openings 44 are most often not in the form of an aperture or a through-hole. The base openings 44 may instead appear as depressions. The base openings 44 can be analogized to the opening of a bag. A bag has an opening that typically does not pass completely through the bag. In the case of the present nonwoven materials 30, as shown in FIG. 10, the base openings 44 open into the interior of the protrusions 32.

Figure 11:
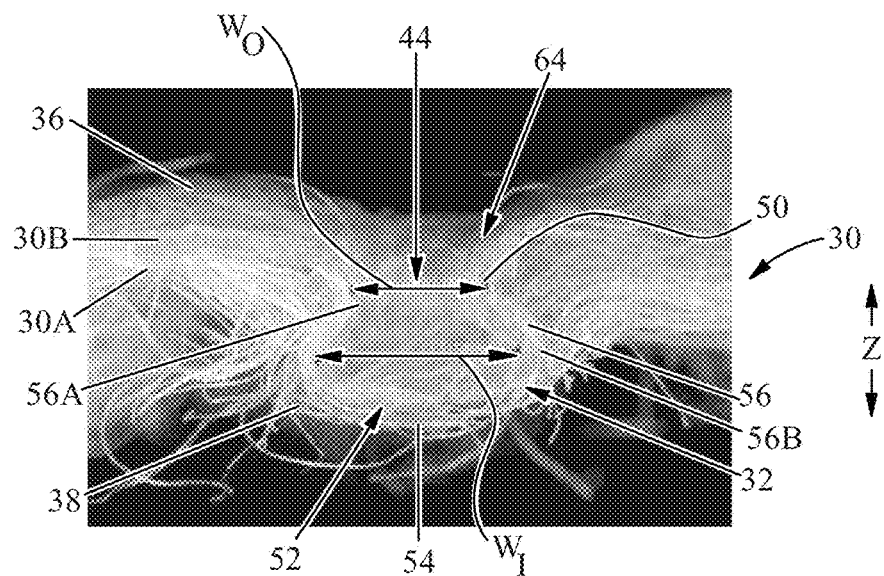
FIG. 11 is a photomicrograph of a cross-section taken along the transverse axis of a deformation showing one example of a multi-layer nonwoven material having a three-dimensional deformation in the form of a protrusion on one side of the material that provides a wide opening on the other side of the material, with the opening facing upward.

FIG. 11 shows one example of a multi-layer nonwoven material 30 having a three-dimensional deformation in the form of a protrusion 32 on one side of the material that provides a wide base opening 44 on the other side of the material. The dimensions of "wide" base openings are described in further detail below. In this case, the base opening 44 is oriented upward in the figure. When there is more than one nonwoven layer, the individual layers can be designated 30A, 30B, etc. The individual layers 30A and 30B each have first and second surfaces, which can be designated similarly to the first and second surfaces 34 and 36 of the nonwoven material (e.g., 34A and 36A for the first and second surfaces of the first layer 30A; and, 34B and 36B for the first and second surfaces of the second layer 30B).

Figure 12:
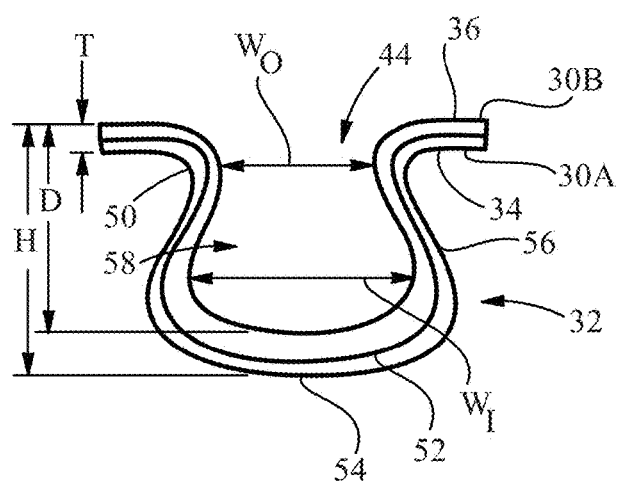
FIG. 12 is a schematic view of the protrusion shown in FIG. 11.

As shown in FIGS. 11 and 12, the protrusions 32 comprise: a base 50 proximate the first surface 34 of the nonwoven material; an opposed enlarged distal portion or cap portion, or "cap" 52, that extends to a distal end 54; side walls (or "sides") 56; an interior 58; and a pair of ends 60 (the latter being shown in FIG. 5). The "base" 50 of the protrusions 32 comprises the narrowest portion of the protrusion when viewed from one of the ends of the protrusion. The term "cap" does not imply any particular shape, other than it comprises the wider portion of the protrusion 32 that includes and is adjacent to the distal end 54 of the protrusion 32. The side walls 56 have an inside surface 56A and an outside surface 56B. As shown in FIGS. 11 and 12, the side walls 56 transition into, and may comprise part of the cap 52. Therefore, it is not necessary to precisely define where the side walls 56 end and the cap 52 begins. The cap 52 will have a maximum interior width, $W_I$, between the inside surfaces 56A of the opposing side walls 56. The cap 52 will also have a maximum exterior width W between the outside surfaces 56B of the opposing side walls 56. The ends 60 of the protrusions 32 are the portions of the protrusions that are spaced furthest apart along the longitudinal axis, L, of the protrusions.

As shown in FIGS. 11 and 12, the narrowest portion of the protrusion 32 defines the base opening 44. The base opening 44 has a width $W_O$. The base opening 44 may be located (in the z-direction) between the plane defined by the second surface 36 of the material and the distal end 54 of the protrusion. As shown in FIGS. 11 and 12, the nonwoven material 30 may have an opening in the second surface 36 (the "second surface opening" 64) that transitions into the base opening 44 (and vice versa), and is the same size as, or larger than the base opening 44. The base opening 44 will, however, generally be discussed more frequently herein since its size will often be more visually apparent to the consumer in those embodiments where the nonwoven material 30 is placed in an article with the base openings 44 visible to the consumer. It should be understood that in certain embodiments, such as in some embodiments in which the base openings 44 face outward (for example, toward a consumer and away from the absorbent core in an absorbent article), it may be desirable for the base openings 44 not to be covered and/or closed off by another web.

As shown in FIG. 12, the protrusions 32 have a depth D measured from the second surface 36 of the nonwoven web to the interior of the protrusion at the distal end 54 of the protrusions. The protrusions 32 have a height H measured from the second surface 36 of the nonwoven web to the distal end 54 of the protrusions. In most cases the height H of the protrusions 32 will be greater than the thickness T of the first region 40. The relationship between the various portions of the deformations may be such that as shown in FIG. 11, when viewed from the end, the maximum interior width $W_I$ of the cap 52 of the protrusions is wider than the width, $W_O$, of the base opening 44.

The protrusions 32 may be of any suitable shape. Since the protrusions 32 are three-dimensional, describing their shape depends on the angle from which they are viewed. When viewed from above (that is, perpendicular to the plane of the web, or plan view) such as in FIG. 5, suitable shapes include, but are not limited to: circular, diamond-shaped, rounded diamond-shaped, U.S. football-shaped, oval-shaped, clover-shaped, heart-shaped, triangle-shaped, teardrop shaped, and elliptical-shaped. (The base openings 44 will typically have a shape similar to the plan view shape of the protrusions 32.) In other cases, the protrusions 32 (and base openings 44) may be non-circular. The protrusions 32 may have similar plan view dimensions in all directions, or the protrusions may be longer in one dimension than another. That is, the protrusions 32 may have different length and width dimensions. If the protrusions 32 have a different length than width, the longer dimension will be referred to as the length of the protrusions. The protrusions 32 may, thus, have a ratio of length to width, or an aspect ratio. The aspect ratios can range from about 1:1 to about 10:1.

As shown in FIG. 5, the protrusions 32 may have a width, W, that varies from one end 60 to the opposing end 60 when the protrusions are viewed in plan view. The width W may vary with the widest portion of the protrusions in the middle of the protrusions, and the width of the protrusions decreasing at the ends 60 of the protrusions. In other cases, the protrusions 32 could be wider at one or both ends 60 than in the middle of the protrusions. In still other cases, protrusions 32 can be formed that have substantially the same width from one end of the protrusion to the other end of the protrusion. If the width of the protrusions 32 varies along the length of the protrusions, the portion of the protrusion where the width is the greatest is used in determining the aspect ratio of the protrusions.

When the protrusions 32 have a length L that is greater than their width W, the length of the protrusions may be oriented in any suitable direction relative to the nonwoven material 30. For example, the length of the protrusions 32 (that is, the longitudinal axis, LA, of the protrusions) may be oriented in the machine direction, the cross-machine direction, or any desired orientation between the machine direction and the cross-machine direction. The protrusions 32 also have a transverse axis TA generally orthogonal to the longitudinal axis LA in the MD-CD plane. In the embodiment shown in FIGS. 5 and 6, the longitudinal axis LA is parallel to the MD. In some embodiments, all the spaced apart protrusions 32 may have generally parallel longitudinal axes LA.

The protrusions 32 may have any suitable shape when viewed from the side. Suitable shapes include those in which there is a distal portion or "cap" with an enlarged dimension and a narrower portion at the base when viewed from at least one side. The term "cap" is analogous to the cap portion of a mushroom. (The cap does not need to resemble that of any particular type of mushroom. In addition, the protrusions 32 may, but need not, have a mushroom-like stem portion.) In some cases, the protrusions 32 may be referred to as having a bulbous shape when viewed from the end 60, such as in FIG. 11. The term "bulbous", as used herein, is intended to refer to the configuration of the protrusions 32 as having a cap 52 with an enlarged dimension and a narrower portion at the base when viewed from at least one side (particularly when viewing from one of the shorter ends 60) of the protrusion 32. The term "bulbous" is not limited to protrusions that have a circular or round plan view configuration that is joined to a columnar portion. The bulbous shape, in the embodiment shown (where the longitudinal axis LA of the deformations 32 is oriented in the machine direction), may be most apparent if a section is taken along the transverse axis TA of the deformation (that is, in the cross-machine direction). The bulbous shape may be less apparent if the deformation is viewed along the length (or longitudinal axis LA) of the deformation such as in FIG. 8.

The protrusions 32 may comprise fibers 38 that at least substantially surround the sides of the protrusions. This means that there are multiple fibers that extend (e.g., in the Z-direction) from the base 50 of the protrusions 32 to the distal end 54 of the protrusions, and contribute to form a portion of the sides 56 and cap 52 of a protrusion. In some cases, the fibers may be substantially aligned with each other in the Z-direction in the sides 56 of the protrusions 32. The phrase "substantially surround", thus, does not require that each individual fiber be wrapped in the X-Y plane substantially or completely around the sides of the protrusions. If the fibers 38 are located completely around the sides of the protrusions, this would mean that the fibers are located 360° around the protrusions. The protrusions 32 may be free of large openings at their ends 60, such as those openings 18 at the leading end and trailing end of the tufts shown in FIG. 1. In some cases, the protrusions 32 may have an opening at only one of their ends, such as at their trailing end. The protrusions 32 also differ from embossed structures such as shown in FIG. 4. Embossed structures typically do not have distal portions that are spaced perpendicularly away (that is, in the Z-direction) from their base that are wider than portions that are adjacent to their base, as in the case of the cap 52 on the present protrusions 32.

The protrusions 32 may have certain additional characteristics. As shown in FIGS. 11 and 12, the protrusions 32 may be substantially hollow. As used herein, the term "substantially hollow" refers to structures which the protrusions 32 are substantially free of fibers in interior of protrusions. The term "substantially hollow", does not, however, require that the interior of the protrusions must be completely free of fibers. Thus, there can be some fibers inside the protrusions. "Substantially hollow" protrusions are distinguishable from filled three-dimensional structures, such as those made by laying down fibers, such as by airlaying or carding fibers onto a forming structure with recesses therein.

The side walls 56 of the protrusions 32 can have any suitable configuration. The configuration of the side walls 56, when viewed from the end of the protrusion such as in FIG. 11, can be linear or curvilinear, or the side walls can be formed by a combination of linear and curvilinear portions. The curvilinear portions can be concave, convex, or combinations of both. For example, the side walls 56 in the embodiment shown in FIG. 11 comprise portions that are curvilinear concave inwardly near the base of the protrusions and convex outwardly near the cap of the protrusions. The sidewalls 56 and the area around the base opening 44 of the protrusions may, under 20× magnification, have a visibly significantly lower concentration of fibers per given area (which may be evidence of a lower basis weight or lower opacity) than the portions of the nonwoven in the unformed first region 40. The protrusions 32 may also have thinned fibers in the sidewalls 56. The fiber thinning, if present, will be apparent in the form of necked regions in the fibers 38 as seen in scanning electron microscope (SEM) images taken at 200× magnification. Thus, the fibers may have a first cross-sectional area when they are in the undeformed nonwoven precursor web, and a second cross-sectional area in the side walls 56 of the protrusions 32 of the deformed nonwoven web, wherein the first cross-sectional area is greater than the second cross-sectional area. The side walls 56 may also comprise some broken fibers as well. In some embodiments, the side walls 56 may comprise greater than or equal to about 30%, alternatively greater than or equal to about 50% broken fibers.

In some embodiments, the distal end 54 of the protrusions 32 may be comprised of original basis weight, non-thinned, and non-broken fibers. If the base opening 44 faces upward, the distal end 54 will be at the bottom of the depression that is formed by the protrusion. The distal end 54 will be free from apertures formed completely through the distal end. Thus, the nonwoven materials may be nonapertured. The term "apertures", as used herein, refers to holes formed in the nonwovens after the formation of the nonwovens, and does not include the pores typically present in nonwovens. The term "apertures" also does not refer to irregular breaks (or interruptions) in the nonwoven material(s) such as shown in FIGS. 15D-15F and FIG. 20 resulting from localized tearing of the material(s) during the process of forming deformations therein, which breaks may be due to variability in the precursor material(s). The distal end 54 may have relatively greater fiber concentration in comparison to the remaining portions of the structure that forms the protrusions. The fiber concentration can be measured by viewing the sample under a microscope and counting the number of fibers within an area. As described in greater detail below, however, if the nonwoven web is comprised of more than one layer, the concentration of fibers in the different portions of the protrusions may vary between the different layers.

The protrusions 32 may be of any suitable size. The size of the protrusions 32 can be described in terms of protrusion length, width, caliper, height, depth, cap size, and opening size. (Unless otherwise stated, the length L and width W of the protrusions are the exterior length and width of the cap 52 of the protrusions.) The dimensions of the protrusions and openings can be measured before and after compression (under either a pressure of 7 kPa or 35 KPa, whichever is specified) in accordance with the Accelerated Compression Method described in the Test Methods section. The protrusions have a caliper that is measured between the same points as the height H, but under a 2 KPa load, in accordance with the Accelerated Compression Method. All dimensions of the protrusions and openings other than caliper (that is, length, width, height, depth, cap size, and opening size) are measured without pressure applied at the time of making the measurement using a microscope at 20× magnification.

In some embodiments, the length of the cap 52 may be in a range from about 1.5 mm to about 10 mm. In some embodiments, the width of the cap (measured where the width is the greatest) may be in a range from about 1.5 mm to about 5 mm. The cap portion of the protrusions may have a plan view surface area of at least about 3 $mm^2$. In some embodiments, the protrusions may have a pre-compression height H that is in a range from about 1 mm to about 10 mm, alternatively from about 1 mm to about 6 mm. In some embodiments, the protrusions may have a post-compression height H that is in a range from about 0.5 mm to about 6 mm, alternatively from about 0.5 mm to about 1.5 mm. In some embodiments, the protrusions may have a depth D, in an uncompressed state that is in a range from about 0.5 mm to about 9 mm, alternatively from about 0.5 mm to about 5 mm. In some embodiments, the protrusions may have a depth D, after compression that is in a range from about 0.25 mm to about 5 mm, alternatively from about 0.25 mm to about 1 mm.

The nonwoven material 30 can comprise a composite of two or more nonwoven materials that are joined together. In such a case, the fibers and properties of the first layer will be designated accordingly (e.g., the first layer is comprised of a first plurality of fibers), and the fibers and properties of the second and subsequent layers will be designated accordingly (e.g., the second layer is comprised of a second plurality of fibers). In a two or more layer structure, there are a number of possible configurations the layers may take following the formation of the deformations therein. These will often depend on the extensibility of the nonwoven materials used for the layers. It is desirable that at least one of the layers have deformations which form protrusions 32 as described herein in which, along at least one cross-section, the width of the cap 52 of the protrusions is greater than the width of the base opening 44 of the deformations. For example, in a two layer structure where one of the layers will serve as the topsheet of an absorbent article and the other layer will serve as an underlying layer (such as an acquisition layer), the layer that has protrusions therein may comprise the topsheet layer. The layer that most typically has a bulbous shape will be the one which is in contact with the male forming member during the process of deforming the web. FIG. 15A-FIG. 15E show different alternative embodiments of three-dimensional protrusions 32 in multiple layer materials.

Figure 15A:
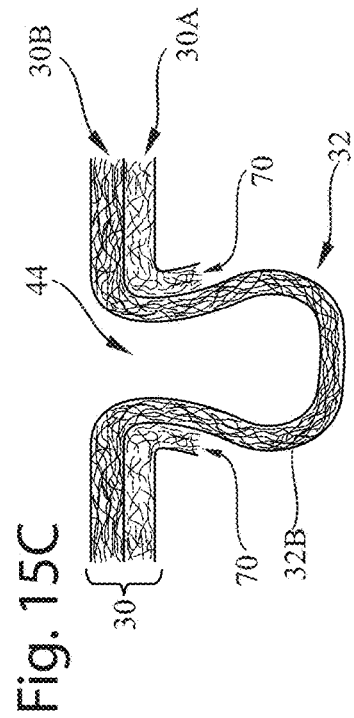
FIG. 15A is a cross-sectional view taken along the transverse axis of a deformation of one embodiment of a multi-layer nonwoven web shown with the base opening facing upward.

In certain embodiments, such as shown in FIGS. 11, 12, and 15A, similar-shaped looped fibers may be formed in each layer of multiple layer nonwoven materials, including in the layer 30A that is spaced furthest from the discrete male forming elements during the process of forming the protrusions 32 therein, and in the layer 30B that is closest to the male forming elements during the process. In the protrusions 32, portions of one layer such as 30B may fit within the other layer, such as 30A. These layers may be referred to as forming a "nested" structure in the protrusions 32. Formation of a nested structure may require the use of two (or more) highly extensible nonwoven precursor webs. In the case of two layer materials, nested structures may form two complete loops, or (as shown in some of the following drawing figures) two incomplete loops of fibers.

As shown in FIG. 15A, a three-dimensional protrusion 32 comprises protrusions 32A formed in the first layer 30A and protrusions 32B formed in the second layer 30B. In one embodiment, the first layer 30A may be incorporated into an absorbent article as an acquisition layer, and the second layer 30B may be a topsheet, and the protrusions formed by the two layers may fit together (that is, are nested). In this embodiment, the protrusions 32A and 32B formed by the first and second layers 30A and 30B fit closely together. The three-dimensional protrusion 32A comprises a plurality of fibers 38A and the three-dimensional protrusion 32B comprises a plurality of fibers 38B. The three-dimensional protrusion 32B is nested into the three-dimensional protrusion 32A. In the embodiment shown, the fibers 38A in the first layer 30A are shorter in length than the fibers 38B in the second layer 30B. In other embodiments, the relative length of fibers in the layers may be the same, or in the opposite relationship wherein the fibers in the first layer are longer than those in the second layer. In addition, in this embodiment, and any of the other embodiments described herein, the nonwoven layers can be inverted when incorporated into an absorbent article, or other article, so that the protrusions 32 face upward (or outward). In such a case, the material suitable for the topsheet will be used in layer 30A, and material suitable for the underlying layer will be used in layer 30B.

Figure 15B:
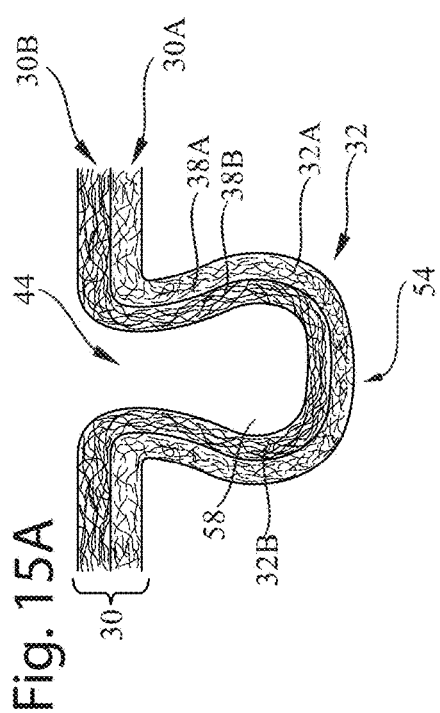
FIG. 15B is a cross-sectional view taken along the transverse axis of a deformation of an alternative embodiment of a multi-layer nonwoven web shown with the base opening facing upward.

FIG. 15B shows that the nonwoven layers need not be in a contacting relationship within the entirety of the protrusion 32. Thus, the protrusions 32A and 32B formed by the first and second layers 30A and 30B may have different heights and/or widths. The two materials may have substantially the same shape in the protrusion 32 as shown in FIG. 15B (where one of the materials has the same the curvature as the other). In other embodiments, however, the layers may have different shapes. It should be understood that FIG. 15B shows only one possible arrangement of layers, and that many other variations are possible, but that as in the case of all the figures, it is not possible to provide a drawing of every possible variation.

Figure 15C:
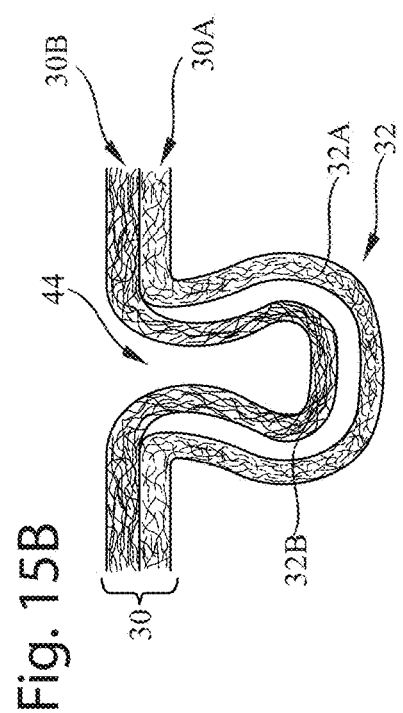
FIG. 15C is a cross-sectional view taken along the transverse axis of a deformation of an alternative embodiment of a multi-layer nonwoven web shown with the base opening facing upward.

As shown in FIG. 15C, one of the layers, such as first layer 30A (e.g., an acquisition layer) may be ruptured in the area of the three-dimensional protrusion 32. As shown in FIG. 15C, the protrusions 32 are only formed in the second layer 30B (e.g., the topsheet) and extend through openings in the first layer 30A. That is, the three-dimensional protrusion 32B in the second layer 30B interpenetrates the ruptured first layer 30A. Such a structure may place the topsheet in direct contact an underlying distribution layer or absorbent core, which may lead to improved dryness. In such an embodiment, the layers are not considered to be "nested" in the area of the protrusion. (In the other embodiments shown in FIGS. 15D-15F, the layers would still be considered to be "nested".) Such a structure may be formed if the material of the second layer 30B is much more extensible than the material of the first layer 30A. In such a case, the openings can be formed by locally rupturing first precursor web by the process described in detail below. The ruptured layer may have any suitable configuration in the area of the protrusion 32. Rupture may involve a simple splitting open of first precursor web, such that the opening in the first layer 30A remains a simple two-dimensional aperture. However, for some materials, portions of the first layer 30A can be deflected or urged out-of-plane (i.e., out of the plane of the first layer 30A) to form flaps 70. The form and structure of any flaps is highly dependent upon the material properties of the first layer 30A. Flaps can have the general structure shown in FIG. 15C. In other embodiments, the flaps 70 can have a more volcano-like structure, as if the protrusion 32B is erupting from the flaps.

Alternatively, as shown in FIGS. 15D-15F, one or both of the first layer 30A and the second layer 30B may be interrupted (or have a break therein) in the area of the three-dimensional protrusion 32. FIGS. 15D and 15E show that the three-dimensional protrusion 32A of the first layer 30A may have an interruption 72A therein. The three-dimensional protrusion 32B of the non-interrupted second layer 30B may coincide with and fit together with the three-dimensional protrusion 32A of the interrupted first layer 30A. Alternatively, FIG. 15F shows an embodiment in which both the first and second layers 30A and 30B have interruptions, or breaks, therein (72A and 72B, respectively). In this case, the interruptions in the layers 30A and 30B are in different locations in the protrusion 32. FIGS. 15D-15F show unintentional random or inconsistent breaks in the materials typically formed by random fiber breakage, which are generally misaligned and can be in the first or second layer, but are not typically aligned and completely through both layers. Thus, there typically will not be an aperture formed completely through all of the layers at the distal end 54 of the protrusions 32.

For dual layer and other multiple layer structures, the basis weight distribution (or the concentration of fibers) within the deformed material 30, as well as the distribution of any thermal point bonds 46 can be different between the layers. As used herein, the term "fiber concentration" has a similar meaning as basis weight, but fiber concentration refers to the number of fibers/given area, rather than g/area as in basis weight. In the case of bond sites 46, the fibers may be melted which may increase the density of the material in the bond sites 46, but the number of fibers will typically be the same as before melting.

Some such dual and multiple layer nonwoven materials may be described in terms of such differences between layers, without requiring one or more of the other features described herein (such as characteristics of the cap portion; controlled collapse under compression; and varying width of the protrusions). Of course such dual and multiple layer nonwoven materials may have any of these other features.

In such dual and multiple layer nonwoven materials each of the layers comprises a plurality of fibers, and in certain embodiments, the protrusions 32 will be formed from fibers in each of the layers. For example, one of the layers, a first layer, may form the first surface 34 of the nonwoven material 30, and one of the layers, a second layer, may form the second surface 36 of the nonwoven material 30. A portion of the fibers in the first layer form part of: the first region 40, the side walls 56 of the protrusions, and the distal ends 54 of the protrusions 32. A portion of the fibers in the second layer form part of: the first region 40, the side walls 56 of the protrusions, and the distal ends 54 of the protrusions 32.

Figure 16:
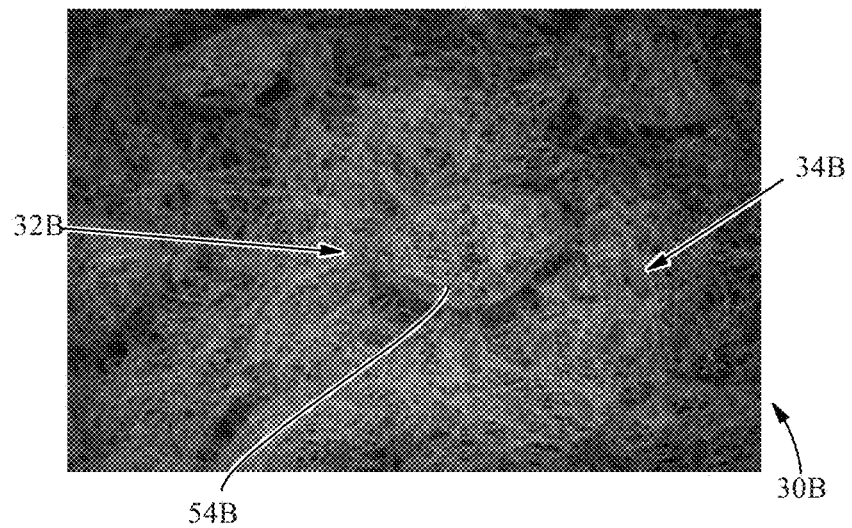
FIG. 16 is a plan view photomicrograph of a nonwoven web with the protrusions oriented upward showing the concentration of fibers in one layer of a two layer structure.
Figure 17:
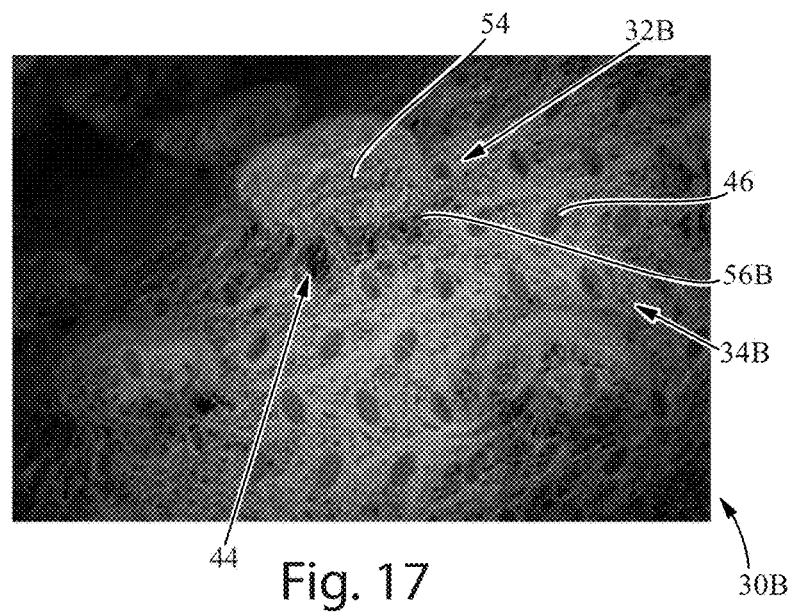
FIG. 17 is a perspective view photomicrograph showing the reduced fiber concentration in the side walls of the protrusions in a layer similar to that shown in FIG. 16.
Figure 18:
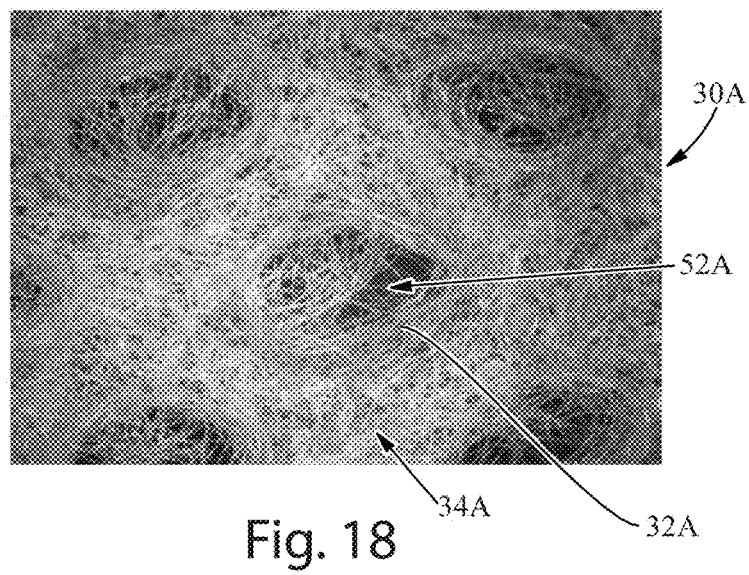
FIG. 18 is a plan view photomicrograph of a nonwoven web with the protrusions oriented upward showing the reduced concentration of fibers in the cap of a protrusion in the other layer (i.e. vs. the layer shown in FIG. 16) of a two layer structure.
Figure 19:
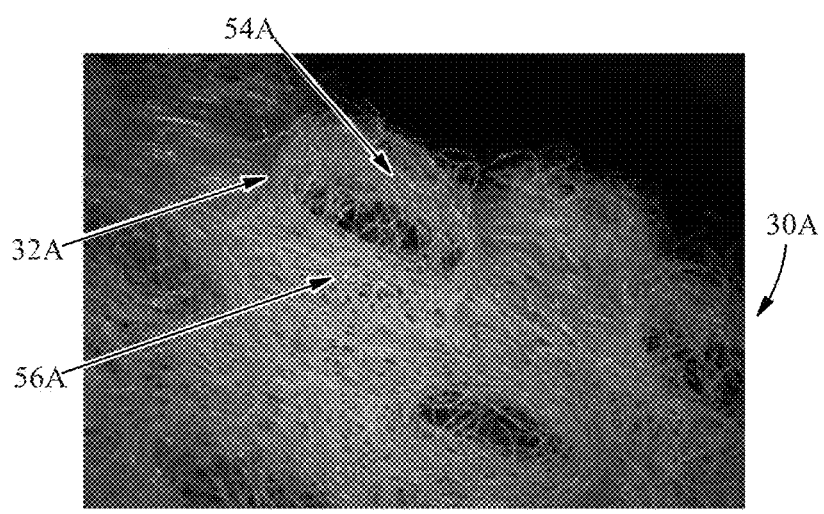
FIG. 19 is a perspective view photomicrograph showing the decreased fiber concentration in the side walls of the protrusions in a layer similar to that shown in FIG. 18.
Figure 19A:
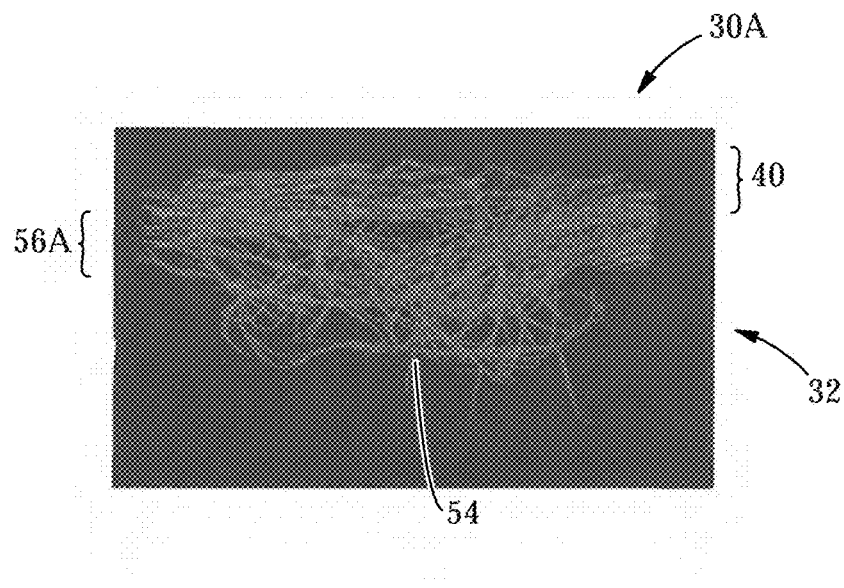
FIG. 19A is a Micro CT scan image showing the side of a protrusion in a single layer of nonwoven material with the protrusion oriented downward.
Figure 19B:
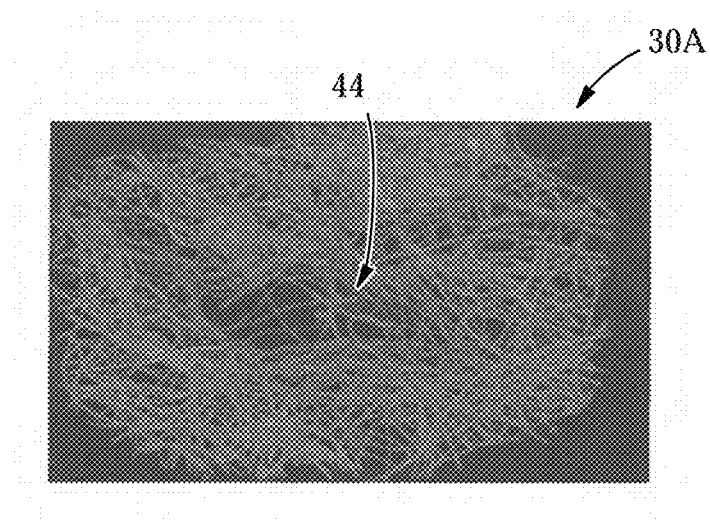
FIG. 19B is a Micro CT scan plan view image showing the base opening of a deformation in a single layer of nonwoven material.

As shown in FIG. 16, the nonwoven layer in contact with the male forming element (e.g., 30B) may have a large portion at the distal end 54B of the protrusion 32B with a similar basis weight to the original nonwoven (that is, to the first region 40). As shown in FIG. 17, the basis weight in the sidewalls 56B of the protrusion 32B and near the base opening 44 may be lower than the basis weight of the first region 40 of the nonwoven layer and the distal end 54 of the protrusion 32B. As shown in FIG. 18, the nonwoven layer in contact with the female forming element (e.g., 30A) may, however, have significantly less basis weight in the cap 52A of the protrusion 32A than in the first region 40 of the nonwoven layer. As shown in FIG. 19, the sidewalls 56A of the protrusion 32A may have less basis weight than the first region 40 of the nonwoven. FIGS. 19A and 19B show that the nonwoven layer 30A in contact with the female forming element may have a fiber concentration that is greatest in the first region 40 (at the upper part of the image in FIG. 19A) and lowest at the distal end 54 of the protrusion 32. The fiber concentration in the side wall 56A, in this case, may be less than that of the first region 40, but greater than that at the distal end 54 of the protrusion 32.

Forming deformations in the nonwoven material may also affect the bonds 46 (thermal point bonds) within the layer (or layers). In some embodiments, the bonds 46 within the distal end 54 of the protrusions 32 may remain intact (not be disrupted) by the deformation process that formed the protrusions 32. In the side walls 56 of the protrusions 32, however, the bonds 46 originally present in the precursor web may be disrupted. When it is said that the bonds 46 may be disrupted, this can take several forms. The bonds 46 can be broken and leave remnants of a bond. In other cases, such as where the nonwoven precursor material is underbonded, the fibers can disentangle from a lightly formed bond site (similar to untying a bow), and the bond site will essentially disappear. In some cases, after the deformation process, the side walls 56 of at least some of the protrusions 32 may be substantially free (or completely free) of thermal point bonds.

Numerous embodiments of dual layer and other multiple layer structures are possible. For example, a nonwoven layer 30B such as that shown in FIGS. 16 and 17 could be oriented with its base openings facing upward, and could serve as a topsheet of a dual or multiple layer nonwoven structure (with at least one other layer serving as an acquisition layer). In this embodiment, the bonds 46 within first region 40 of nonwoven layer 30B and the distal end 54 of the protrusions 32 remain intact. In the side walls 56 of the protrusions 32, however, the bonds 46 originally present in the precursor web are disrupted such that the side walls 56 are substantially free of thermal point bonds. Such a topsheet could be combined with an acquisition layer in which the concentration of fibers within the layer 30A in the first region 40 and the distal end 54 of the protrusions 32 is also greater than the concentration of fibers in the side walls 56 of the protrusions 32.

In other embodiments, the acquisition layer 30A described in the preceding paragraph may have thermal point bonds 46 within first region 40 of nonwoven layer 30B and the distal end 54 of the protrusions 32 that remain intact. In the side walls 56 of the protrusions 32, however, the bonds 46 originally present in the precursor web comprising the acquisition layer 30A are disrupted such that the side walls 56 of the acquisition layer 30A are substantially free of thermal point bonds. In other cases, the thermal point bonds in the acquisition layer 30A at the top of the protrusions 32 may also be disrupted so that the distal end 54 of at least some of the protrusions are substantially or completely free of thermal point bonds.

In other embodiments, a dual layer or multiple layer structure may comprise a topsheet and an acquisition layer that is oriented with its base openings facing upward in which the concentration of fibers at the distal end 54 of each layer (relative to other portions of the layer) differs between layers. For example, in one embodiment, in the layer that forms the topsheet (second layer), the concentration of fibers in the first region and the distal ends of the protrusions are each greater than the concentration of fibers in the side walls of the protrusions. In the layer that forms the acquisition layer (first layer), the concentration of fibers in the first region of the acquisition layer may be greater than the concentration of fibers in the distal ends of the protrusions. In a variation of this embodiment, the concentration of fibers in the first region of the first layer (acquisition layer) is greater than the concentration of fibers in the side walls of the protrusions in the first layer, and the concentration of fibers in the side walls of the protrusions in the first layer is greater than the concentration of fibers forming the distal ends of the protrusions in the first layer. In some embodiments in which the first layer comprises a spunbond nonwoven material (in which the precursor material had thermal point bonds distributed substantially evenly throughout), a portion of the fibers that form the first region in the first layer comprise thermal point bonds, and the portion of the fibers in the first layer forming the side walls and distal ends of at least some of the protrusions may be substantially free of thermal point bonds. In these embodiments, in at least some of the protrusions, at least some of the fibers in the first layer may form a nest or circle around (that is, encircle) the perimeter of the protrusion at the transition between the wide wall and the base of the protrusion as shown in FIG. 19.

The base openings 44 can be of any suitable shape and size. The shape of the base opening 44 will typically be similar to, or the same as, the plan view shape of the corresponding protrusions 32. The base opening 44 may have a width that is greater than about any of the following dimensions before (and after compression): 0.5 mm, 0.7 mm, 0.8 mm, 0.9 mm, 1 mm, or any 0.1 mm increment above 1 mm. The width of the base opening 44 may be in a range that is from any of the foregoing amounts up to about 4 mm, or more. The base openings 44 may have a length that ranges from about 1.5 mm or less to about 10 mm, or more. The base openings 44 may have an aspect ratio that ranges from about 1:1 to 20:1, alternatively from about 1:1 to 10:1.

Measurements of the dimensions of the base opening can be made on a photomicrograph. When the size of the width of the base opening 44 is specified herein, it will be appreciated that if the openings are not of uniform width in a particular direction, the width, $W_O$, is measured at the widest portion as shown in FIG. 6. The nonwoven materials of the present invention and the method of making the same may create deformations with a wider opening than certain prior structures which have a narrow base. This allows the base openings 44 to be more visible to the naked eye. The width of the base opening 44 is of interest because, being the narrowest portion of the opening, it will be most restrictive of the size of the opening. The deformations retain their wide base openings 44 after compression perpendicular to the plane of the first region 40.

The deformations may compress under load. In some cases, it may be desirable that the load is low enough so that, if the nonwoven is worn against a wearer's body, with the deformations in contact with the wearer's body, the deformations will be soft and will not imprint the skin. This applies in cases where either the protrusions 32 or the base openings 44 are oriented so that they are in contact with the wearer's body. For example, it may be desirable for the deformations to compress under pressures of 2 kPa or less. In other cases, it will not matter if the deformations imprint the wearer's skin. It may be desirable for at least one of the protrusions 32 in the nonwoven material 30 to collapse or buckle in the controlled manner described below under the 7 kPa load when tested in accordance with the Accelerated Compression Method in the Test Methods section below. Alternatively, at least some, or in other cases, a majority of the protrusions 32 may collapse in the controlled manner described herein. Alternatively, substantially all of the protrusions 32 may collapse in the controlled manner described herein. The ability of the protrusions 32 to collapse may also be measured under a load of 35 kPa. The 7 kPa and 35 kPa loads simulate manufacturing and compression packaging conditions. Wear conditions can range from no or limited pressure (if the wearer is not sitting on the absorbent article) up to 2 kPa, 7 kPa, or more.

Figure 13:
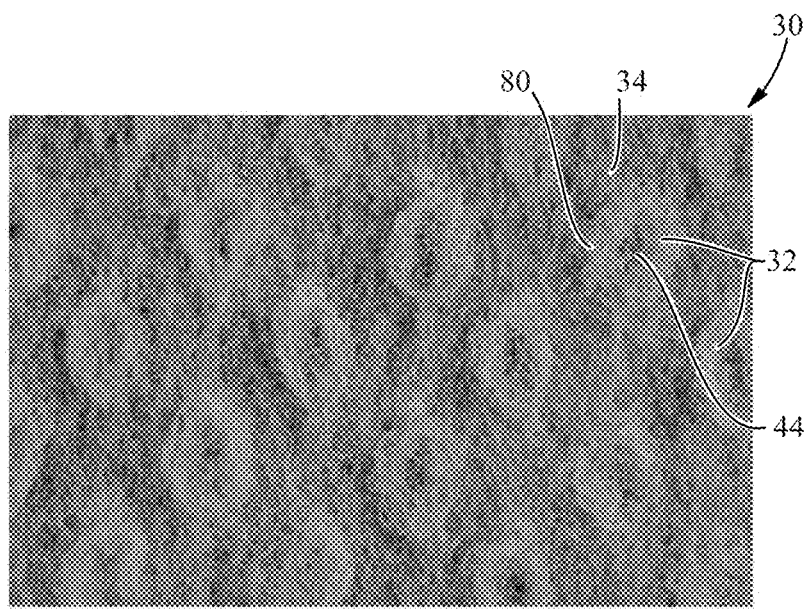
FIG. 13 is a plan view photomicrograph from the protrusion side of a material after it has been subjected to compression showing the high fiber concentration region around the perimeter of the protrusion.
Figure 14:
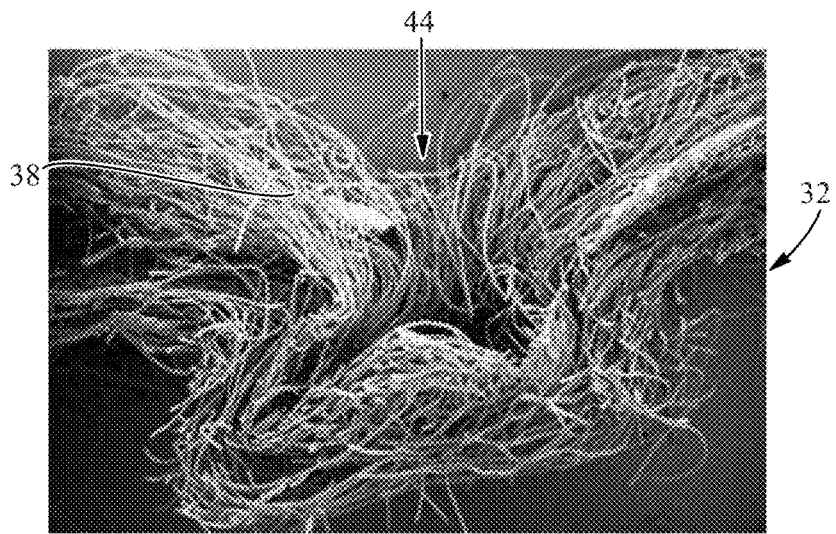
FIG. 14 is a photomicrograph of the cross-section of a protrusion taken along the transverse axis of the protrusion showing the protrusion after it has been subjected to compression.

The protrusions 32 may collapse in a controlled manner after compression to maintain the wide opening 44 at the base. FIG. 13 shows the first surface 34 of a nonwoven material 30 according to the present invention after it has been subjected to compression. FIG. 14 is a side view of a single downwardly-oriented protrusion 32 after it has been subjected to compression. As shown in FIG. 13, when the protrusions 32 have been compressed, there appears to be a higher concentration of fibers in the form of a ring of increased opacity 80 around the base opening 44. When a compressive force is applied to the nonwoven materials, the side walls 56 of the protrusions 32 may collapse in a more desirable/controlled manner such that the side walls 56 become concave and fold into regions of overlapping layers (such as into an s-shape/accordion-shape). The ring of increased opacity 80 represents folded layers of material. In other words, the protrusions 32 may have a degree of dimensional stability in the X-Y plane when a Z-direction force is applied to the protrusions. It is not necessary that the collapsed configuration of the protrusions 32 be symmetrical, only that the collapsed configuration prevent the protrusions 32 from flopping over or pushing back into the original plane of the nonwoven, and significantly reducing the size of the base opening (for example, by 50% or more). For example, as shown in FIG. 14, the left side of the protrusion 32 can form a z-folded structure, and the right side of the protrusion does not, but still appears, when viewed from above, to have higher opacity due to a degree of overlapping of the material in the folded portion. Without wishing to be bound by any particular theory, it is believed that the wide base opening 44 and large cap 52 (greater than the width of the base opening 44), combined with the lack of a pivot point, causes the protrusions 32 to collapse in a controlled manner (prevents the protrusion 32 from flopping over). Thus, the protrusions 32 are free of a hinge structure that would otherwise permit them to fold to the side when compressed. The large cap 52 also prevents the protrusion 32 from pushing back into the original plane of the nonwoven.

The deformations can be disposed in any suitable density across the surface of the nonwoven material 30. The deformations may, for example, be present in a density of: from about 5 to about 100 deformations; alternatively from about 10 to about 50 deformations; alternatively from about 20 to about 40 deformations, in an area of 10 $cm^2$.

The deformations can be disposed in any suitable arrangement across the plane of the nonwoven material. Suitable arrangements include, but are not limited to: staggered arrangements, and zones.

Figure 27:
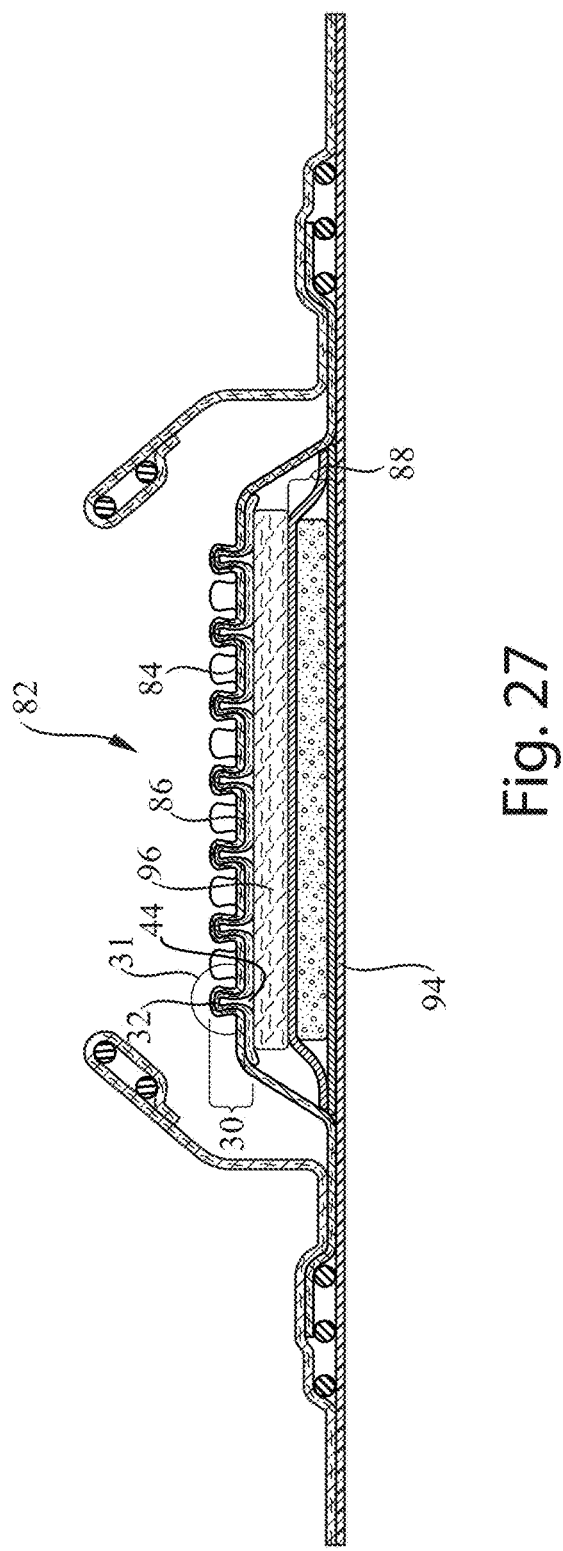
FIG. 27 is an alternative transverse cross-section of the diaper of FIG. 25.

The nonwoven webs 30 described herein can comprise any suitable component or components of an absorbent article. For example, the nonwoven webs can comprise the topsheet of an absorbent article, or as shown in FIG. 25, if the nonwoven web 30 comprises more than one layer, the nonwoven web can comprise a combined topsheet 84 and acquisition layer 86 of an absorbent article, such as diaper 82. The diaper 82 shown in FIGS. 25-27 also comprises an absorbent core 88, a backsheet 94, and a distribution layer 96. The nonwoven materials of the present disclosure may also form an outer cover of an absorbent article, such as backsheet 94. The nonwoven webs 30 can be placed in an absorbent article with the deformations 31 in any suitable orientation. For example, the protrusions 32 can be oriented up or down. In other words, the protrusions 32 may be oriented toward the absorbent core 88 as shown in FIG. 26. Thus, for example, it may be desirable for the protrusions 32 to point inward toward the absorbent core 88 in a diaper (that is, away from the body-facing side and toward the garment-facing side), or other absorbent article. Alternatively, the protrusions 32 may be oriented so that they extend away from the absorbent core of the absorbent article as shown in FIG. 27. In still other embodiments, the nonwoven webs 30 can be made so that they have some protrusions 32 that are oriented upward, and some that are oriented downward. Without wishing to be bound to any particular theory, it is believed that such a structure may be useful in that the protrusions that are oriented upward can be more effective for cleaning the body from exudates, while the protrusions that are oriented downward can be more effective for absorption of exudates into the absorbent core. Therefore, without being bound to theory, a combination of these two protrusion orientations will offer advantage that the same product can fulfill the two functions.

A two or more layer nonwoven structure may provide fluid handling benefits. If the layers are integrated together, and the protrusions 32 are oriented toward the absorbent core, they may also provide a dryness benefit. It may be desirable, on the other hand, for the protrusions 32 to point outward, away from the absorbent core in a pad for a wet or dry mop to provide a cleaning benefit. In some embodiments, when the nonwoven web 30 is incorporated into an absorbent article, the underlying layers can be either substantially, or completely free, of tow fibers. Suitable underlying layers that are free of tow fibers may, for example, comprise a layer or patch of cross-linked cellulose fibers. In some cases, it may be desirable that the nonwoven material 30 is not entangled with (that is, is free from entanglement with) another web.

The layers of the nonwoven structure (e.g., a topsheet and/or acquisition layer) may be colored. Color may be imparted to the webs in any suitable manner including, but not limited to by color pigmentation. The term "color pigmentation" encompasses any pigments suitable for imparting a non-white color to a web. This term therefore does not include "white" pigments such as $TiO_2$ which are typically added to the layers of conventional absorbent articles to impart them with a white appearance. Pigments are usually dispersed in vehicles or substrates for application, as for instance in inks, paints, plastics or other polymeric materials. The pigments may for example be introduced in a polypropylene masterbatch. A masterbatch comprises a high concentration of pigment and/or additives which are dispersed in a carrier medium which can then be used to pigment or modify the virgin polymer material into a pigmented bicomponent nonwoven. An example of suitable colored masterbatch material that can be introduced is Pantone color 270 Sanylen violet PP 42000634 ex Clariant, which is a PP resin with a high concentration of violet pigment. Typically, the amount of pigments introduced by weight of the webs may be of from 0.3%-2.5%. Alternatively, color may be imparted to the webs by way of impregnation of a colorant into the substrate. Colorants such as dyes, pigments, or combinations may be impregnated in the formation of substrates such as polymers, resins, or nonwovens. For example, the colorant may be added to molten batch of polymer during fiber or filament formation.

Precursor Materials.

The nonwoven materials of the present invention can be made of any suitable nonwoven materials ("precursor materials"). The nonwoven webs can be made from a single layer, or multiple layers (e.g., two or more layers). If multiple layers are used, they can be comprised of the same type of nonwoven material, or different types of nonwoven materials. In some cases, the precursor materials may be free of any film layers.

The fibers of the nonwoven precursor material(s) can be made of any suitable materials including, but not limited to natural materials, synthetic materials, and combinations thereof. Suitable natural materials include, but are not limited to cellulose, cotton linters, bagasse, wool fibers, silk fibers, etc. Cellulose fibers can be provided in any suitable form, including but not limited to individual fibers, fluff pulp, drylap, liner board, etc. Suitable synthetic materials include, but are not limited to nylon, rayon and polymeric materials. Suitable polymeric materials include, but are not limited to: polyethylene (PE), polyester, polyethylene terephthalate (PET), polypropylene (PP), and co-polyester. In some embodiments, however, the nonwoven precursor materials can be either substantially, or completely free, of one or more of these materials. For example, in some embodiments, the precursor materials may be substantially free of cellulose, and/or exclude paper materials. In some embodiments, one or more precursor materials can comprise up to 100% thermoplastic fibers. The fibers in some cases may, therefore, be substantially non-absorbent. In some embodiments, the nonwoven precursor materials can be either substantially, or completely free, of tow fibers.

The precursor nonwoven materials can comprise any suitable types of fibers. Suitable types of fibers include, but are not limited to: monocomponent, bicomponent, and/or biconstituent, non-round (e.g., shaped fibers (including but not limited to fibers having a trilobal cross-section) and capillary channel fibers). The fibers can be of any suitable size. The fibers may, for example, have major cross-sectional dimensions (e.g., diameter for round fibers) ranging from 0.1-500 microns. Fiber size can also be expressed in denier, which is a unit of weight per length of fiber. The constituent fibers may, for example, range from about 0.1 denier to about 100 denier. The constituent fibers of the nonwoven precursor web(s) may also be a mixture of different fiber types, differing in such features as chemistry (e.g., PE and PP), components (mono- and bi-), shape (i.e. capillary channel and round) and the like.

The nonwoven precursor webs can be formed from many processes, such as, for example, air laying processes, wetlaid processes, meltblowing processes, spunbonding processes, and carding processes. The fibers in the webs can then be bonded via spunlacing processes, hydroentangling, calendar bonding, through-air bonding and resin bonding. Some of such individual nonwoven webs may have bond sites 46 where the fibers are bonded together.

In the case of spunbond webs, the web may have a thermal point bond 46 pattern that is not highly visible to the naked eye. For example, dense thermal point bond patterns are equally and uniformly spaced are typically not highly visible. After the material is processed through the mating male and female rolls, the thermal point bond pattern is still not highly visible. Alternatively, the web may have a thermal point bond pattern that is highly visible to the naked eye. For example, thermal point bonds that are arranged into a macro-pattern, such as a diamond pattern, are more visible to the naked eye. After the material is processed through the mating male and female rolls, the thermal point bond pattern is still highly visible and can provide a secondary visible texture element to the material.

The basis weight of nonwoven materials is usually expressed in grams per square meter (gsm). The basis weight of a single layer nonwoven material can range from about 8 gsm to about 100 gsm, depending on the ultimate use of the material 30. For example, the topsheet of a topsheet/acquisition layer laminate or composite may have a basis weight from about 8 to about 40 gsm, or from about 8 to about 30 gsm, or from about 8 to about 20 gsm. The acquisition layer may have a basis weight from about 10 to about 120 gsm, or from about 10 to about 100 gsm, or from about 10 to about 80 gsm. The basis weight of a multi-layer material is the combined basis weight of the constituent layers and any other added components. The basis weight of multi-layer materials of interest herein can range from about 20 gsm to about 150 gsm, depending on the ultimate use of the material 30. The nonwoven precursor webs may have a density that is between about 0.01 and about 0.4 $g/cm^3$ measured at 0.3 psi (2 kPa).

The precursor nonwoven webs may have certain desired characteristics. The precursor nonwoven web(s) each have a first surface, a second surface, and a thickness. The first and second surfaces of the precursor nonwoven web(s) may be generally planar. It is typically desirable for the precursor nonwoven web materials to have extensibility to enable the fibers to stretch and/or rearrange into the form of the protrusions. If the nonwoven webs are comprised of two or more layers, it may be desirable for all of the layers to be as extensible as possible. Extensibility is desirable in order to maintain at least some non-broken fibers in the sidewalls around the perimeter of the protrusions. It may be desirable for individual precursor webs, or at least one of the nonwovens within a multi-layer structure, to be capable of undergoing an apparent elongation (strain at the breaking force, where the breaking force is equal to the peak force) of greater than or equal to about one of the following amounts: 100% (that is double its unstretched length), 110%, 120%, or 130% up to about 200%. It is also desirable for the precursor nonwoven webs to be capable of undergoing plastic deformation to ensure that the structure of the deformations is "set" in place so that the nonwoven web will not tend to recover or return to its prior configuration.

Figure 20:
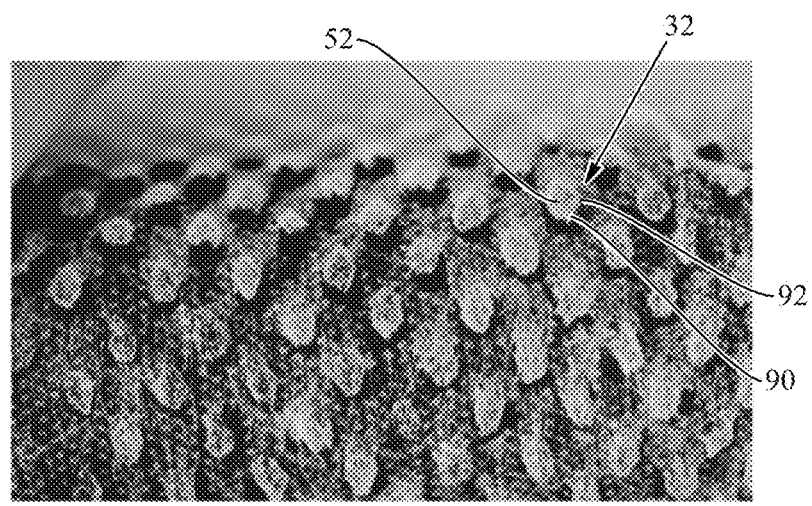
FIG. 20 is a perspective view photomicrograph of one layer of a multiple layer nonwoven material on the surface of a forming roll showing the "hanging chads" that can be formed in one of the layers when some nonwoven precursor web materials are used.

Materials that are not extensible enough (e.g., inextensible PP) may form broken fibers around much of the perimeter of the deformation, and create more of a "hanging chad" 90 (i.e., the cap 52 of the protrusions 32 may be at least partially broken from and separated from the rest of the protrusion (as shown in FIG. 20). The area on the sides of the protrusion where the fibers are broken is designated with reference number 92. Materials such as that shown in FIG.

20 will not be suitable for a single layer structure, and, if used, will typically be part of a composite multi-layer structure in which another layer has protrusions 32 as described herein.

When the fibers of a nonwoven web are not very extensible, it may be desirable for the nonwoven to be underbonded as opposed to optimally bonded. A thermally bonded nonwoven web's tensile properties can be modified by changing the bonding temperature. A web can be optimally or ideally bonded, underbonded, or overbonded. Optimally or ideally bonded webs are characterized by the highest breaking force and apparent elongation with a rapid decay in strength after reaching the breaking force. Under strain, bond sites fail and a small amount of fibers pull out of the bond site. Thus, in an optimally bonded nonwoven, the fibers 38 will stretch and break around the bond sites 46 when the nonwoven web is strained beyond a certain point. Often there is a small reduction in fiber diameter in the area surrounding the thermal point bond sites 46. Underbonded webs have a lower breaking force and apparent elongation when compared to optimally bonded webs, with a slow decay in strength after reaching the breaking force. Under strain, some fibers will pull out from the thermal point bond sites 46. Thus, in an underbonded nonwoven, at least some of the fibers 38 can be separated easily from the bond sites 46 to allow the fibers 38 to pull out of the bond sites and rearrange when the material is strained. Overbonded webs also have a lowered breaking force and elongation when compared to optimally bonded webs, with a rapid decay in strength after reaching the breaking force. The bond sites look like films and result in complete bond site failure under strain.

When the nonwoven web comprises two or more layers, the different layers can have the same properties, or any suitable differences in properties relative to each other. In one embodiment, the nonwoven web 30 can comprise a two layer structure that is used in an absorbent article. For convenience, the precursor webs and the material into which they are formed will generally be referred to herein by the same reference numbers. However, in some cases, for additional clarity the precursor web may be designated as 30'. As described above, one of the layers, a second layer 30B, can serve as the topsheet of the absorbent article, and the first layer 30A can be an underlying layer (or sub-layer) and serve as an acquisition layer. The acquisition layer 30A receives liquids that pass through the topsheet and distributes them to underlying absorbent layers. In such a case, the topsheet 30B may be less hydrophilic than sub-layer(s) 30A, which may lead to better dewatering of the topsheet. In other embodiments, the topsheet can be more hydrophilic than the sub-layer(s). In some cases, the pore size of the acquisition layer may be reduced, for example via using fibers with smaller denier or via increasing the density of the acquisition layer material, to better dewater the pores of the topsheet.

The second nonwoven layer 30B that may serve as the topsheet can have any suitable properties. Properties of interest for the second nonwoven layer, when it serves as a topsheet, in addition to sufficient extensibility and plastic deformation may include uniformity and opacity. As used herein, "uniformity" refers to the macroscopic variability in basis weight of a nonwoven web. As used, herein, "opacity" of nonwoven webs is a measure of the impenetrability of visual light, and is used as visual determination of the relative fiber density on a macroscopic scale. As used herein, "opacity" of the different regions of a single nonwoven deformation is determined by taking a photomicrograph at 20× magnification of the portion of the nonwoven containing the deformation against a black background. Darker areas indicate relatively lower opacity (as well as lower basis weight and lower density) than white areas.

Several examples of nonwoven materials suitable for use as the second nonwoven layer 30B include, but are not limited to: spunbonded nonwovens; carded nonwovens; and other nonwovens with high extensibility (apparent elongation in the ranges set forth above) and sufficient plastic deformation to ensure the structure is set and does not have significant recovery. One suitable nonwoven material as a topsheet for a topsheet/acquisition layer composite structure may be an extensible spunbonded nonwoven comprising polypropylene and polyethylene. The fibers can comprise a blend of polypropylene and polyethylene, or they can be bi-component fibers, such as a sheath-core fiber with polyethylene on the sheath and polypropylene in the core of the fiber. Another suitable material is a bi-component fiber spunbonded nonwoven comprising fibers with a polyethylene sheath and a polyethylene/polypropylene blend core.

The first nonwoven layer 30A that may, for example, serve as the acquisition layer can have any suitable properties. Properties of interest for the first nonwoven layer, in addition to sufficient extensibility and plastic deformation may include uniformity and opacity. If the first nonwoven layer 30A serves as an acquisition layer, its fluid handling properties must also be appropriate for this purpose. Such properties may include: permeability, porosity, capillary pressure, caliper, as well as mechanical properties such as sufficient resistance to compression and resiliency to maintain void volume. Suitable nonwoven materials for the first nonwoven layer when it serves as an acquisition layer include, but are not limited to: spunbonded nonwovens; through-air bonded ("TAB") carded nonwoven materials; spunlace nonwovens; hydroentangled nonwovens; and, resin bonded carded nonwoven materials. Of course, the composite structure may be inverted and incorporated into an article in which the first layer 30A serves as the topsheet and the second layer 30B serves as an acquisition layer. In such cases, the properties and exemplary methods of the first and second layers described herein may be interchanged.

The layers of a two or more layered nonwoven web structure can be combined together in any suitable manner. In some cases, the layers can be unbonded to each other and held together autogenously (that is, by virtue of the formation of deformations therein). For example, both precursor webs 30A and 30B contribute fibers to deformations in a "nested" relationship that joins the two precursor webs together, forming a multi-layer web without the use or need for adhesives or thermal bonding between the layers. In other embodiments, the layers can be joined together by other mechanisms. If desired an adhesive between the layers, ultrasonic bonding, chemical bonding, resin or powder bonding, thermal bonding, or bonding at discrete sites using a combination of heat and pressure can be selectively utilized to bond certain regions or all of the precursor webs. In addition, the multiple layers may be bonded during processing, for example, by carding one layer of nonwoven onto a spunbond nonwoven and thermal point bonding the combined layers. In some cases, certain types of bonding between layers may be excluded. For example, the layers of the present structure may be non-hydroentangled together.

If adhesives are used, they can be applied in any suitable manner or pattern including, but not limited to: slots, spirals, spray, and curtain coating. Adhesives can be applied in any suitable amount or basis weight including, but not limited to between about 0.5 and about 30 gsm, alternatively between about 2 and about 5 gsm. Examples of adhesives could include hot melt adhesives, such as polyolefins and styrene block copolymers.

A certain level of adhesive may reduce the level of fuzz on the surface of the nonwoven material even though there may be a high percentage of broken fibers as a result of the deformation process. Glued dual-layer laminates produced as described herein are evaluated for fuzz. The method utilizes a Martindale Abrasion Tester, based upon ASTM D4966-98. After abrading the samples, they are graded on a scale of 1-10 based on the degree of fiber pilling (1=no fiber pills; 10=large quantity and size of fiber pills). The protrusions are oriented away from the abrader so the land area in between the depressions is the primary surface abraded. Even though the samples may have a significant amount of fiber breakage (greater than 25%, sometimes greater than 50%) in the side walls of the protrusions/depressions, the fuzz value may be low (around 2) for several different material combinations, as long as the layers do not delaminate during abrasion. Delamination is best prevented by glue basis weight, for example a glue basis weight greater than 3 gsm, and glue coverage.

Figure 24:
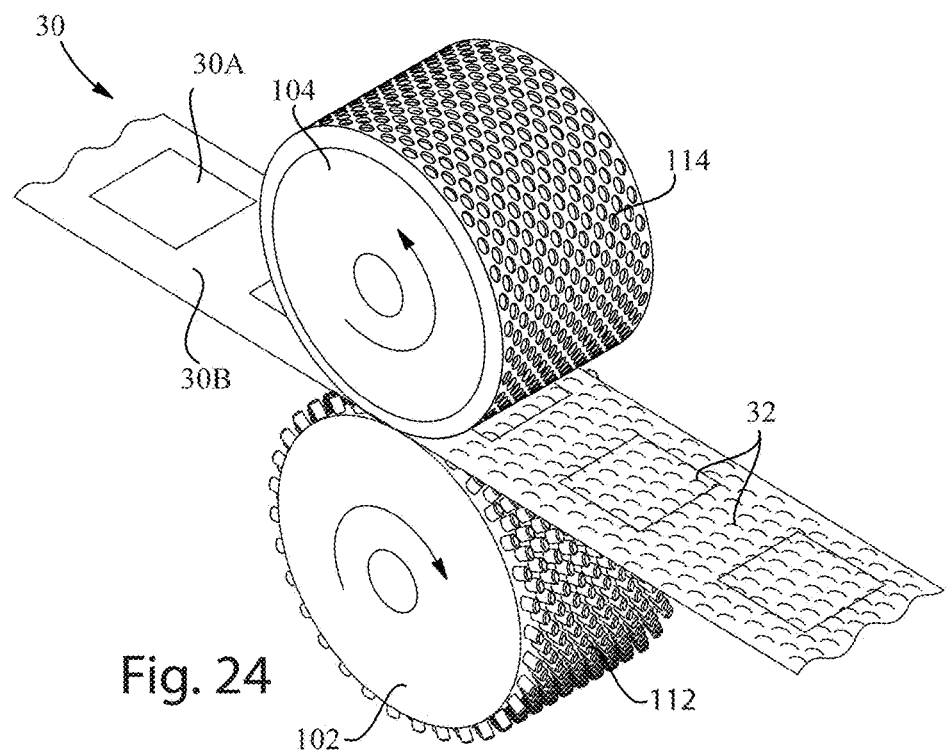
FIG. 24 is a schematic perspective view of one version of a method of making nonwoven materials having deformations therein where two precursor materials are used, one of which is a continuous web and the other of which is in the form of discrete pieces.

When the precursor nonwoven web comprises two or more layers, it may be desirable for at least one of the layers to be continuous, such as in the form of a web that is unwound from a roll. In some embodiments, each of the layers can be continuous. In alternative embodiments, such as shown in FIG. 24, one or more of the layers can be continuous, and one or more of the layers can have a discrete length. The layers may also have different widths. For example, in making a combined topsheet and acquisition layer for an absorbent article, the nonwoven layer that will serve as the topsheet may be a continuous web, and the nonwoven layer that will serve as the acquisition layer may be fed into the manufacturing line in the form of discrete length (for example, rectangular, or other shaped) pieces that are placed on top of the continuous web. Such an acquisition layer may, for example, have a lesser width than the topsheet layer. The layers may be combined together as described above.

III. Methods of Making the Nonwoven Materials

The nonwoven materials are made by a method comprising the steps of: a) providing at least one precursor nonwoven web; b) providing an apparatus comprising a pair of forming members comprising a first forming member (a "male" forming member) and a second forming member (a "female" forming member); and c) placing the precursor nonwoven web(s) between the forming members and mechanically deforming the precursor nonwoven web(s) with the forming members. The forming members have a machine direction (MD) orientation and a cross-machine direction (CD) orientation.

The first and second forming members can be plates, rolls, belts, or any other suitable types of forming members. In some embodiments, it may be desirable to modify the apparatus for incrementally stretching a web described in U.S. Pat. No. 8,021,591, Curro, et al. entitled "Method and Apparatus for Incrementally Stretching a Web" by providing the activation members described therein with the forming elements of the type described herein. In the embodiment of the apparatus 100 shown in FIG. 21, the first and second forming members 102 and 104 are in the form of non-deformable, meshing, counter-rotating rolls that form a nip 106 therebetween. The precursor web(s) is/are fed into the nip 106 between the rolls 102 and 104. Although the space between the rolls 102 and 104 is described herein as a nip, as discussed in greater detail below, in some cases, it may be desirable to avoid compressing the precursor web(s) to the extent possible.

First Forming Member.

The first forming member (such as "male roll") 102 has a surface comprising a plurality of first forming elements which comprise discrete, spaced apart male forming elements 112. The male forming elements are spaced apart in the machine direction and in the cross-machine direction. The term "discrete" does not include continuous or non-discrete forming elements such as the ridges and grooves on corrugated rolls (or "ring rolls") which have ridges that may be spaced apart in one, but not both, of the machine direction and in the cross-machine direction.

As shown in FIG. 22, the male forming elements 112 have a base 116 that is joined to (in this case is integral with) the first forming member 102, a top 118 that is spaced away from the base, and side walls (or "sides") 120 that extend between the base 116 and the top 118 of the male forming elements. The male elements 112 may also have a transition portion or region 122 between the top 118 and the side walls 120. The male elements 112 also have a plan view periphery, and a height $H_1$ (the latter being measured from the base 116 to the top 118). The discrete elements on the male roll may have a top 118 with a relatively large surface area (e.g., from about 1 mm to about 10 mm in width, and from about 1 mm to about 20 mm in length) for creating a wide deformation. The male elements 112 may, thus, have a plan view aspect ratio (ratio of length to width) that ranges from about 1:1 to about 10:1. For the purpose of determining the aspect ratio, the larger dimension of the male elements 112 will be consider the length, and the dimension perpendicular thereto will be considered to be the width of the male element. The male elements 112 may have any suitable configuration.

The base 116 and the top 118 of the male elements 112 may have any suitable plan view configuration, including but not limited to: a rounded diamond configuration as shown in FIGS. 21 and 22, an American football-like shape, triangle, circle, clover, a heart-shape, teardrop, oval, or an elliptical shape. The configuration of the base 116 and the configuration of the top 118 of the male elements 112 may be in any of the following relationships to each other: the same, similar, or different. The top 118 of the male elements 112 can be flat, rounded, or any configuration therebetween.

Figure 22A:
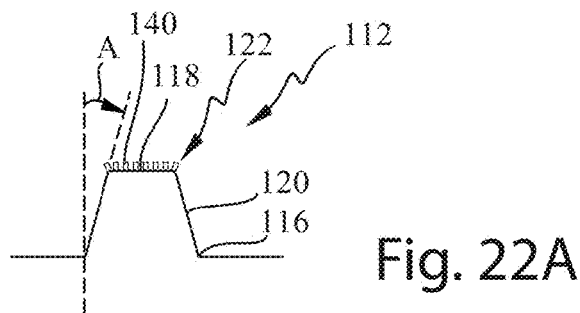
FIG. 22A is a schematic side view of a male element with tapered side walls.
Figure 22B:
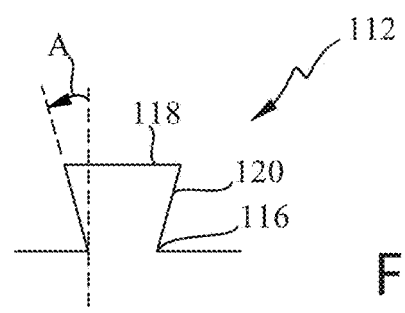
FIG. 22B is a schematic side view of a male element with undercut side walls.

The side walls 120 of the male elements 112 may have any suitable configuration. The male elements 112 may have vertical side walls 120, or tapered side walls 120. By vertical side walls, it is meant that the side walls 120 have zero degree side wall angles relative to the perpendicular from the base 116 of the side wall. In other embodiments, as shown in FIG. 22A, the side walls 120 can be tapered inwardly toward the center of the male forming elements 112 from the base 116 to the top 118 so that the side walls 120 form an angle, A, greater than zero. In still other embodiments, as shown in FIG. 22B, the male forming elements 112 may have a wider top surface than base so that the side walls 120 are angled outwardly away from the center of the male forming elements 112 from the base 116 to the top 118 of the male elements 112 (that is, the side walls may be undercut). The side wall angle can be the same on all sides of the male elements 112. Alternatively, the male elements 112 may have a different side wall angle on one or more of their sides. For example, the leading edge (or "LE") and trailing edge (or "TE") of the male elements (with respect to the machine direction) may have equal side wall angles, and the sides of the male elements may have equal side wall angles, but the side wall angles of the LE and TE may be different from the side wall angle of the sides. In certain embodiments, for example, the side wall angle of the sides of the male elements 112 may be vertical, and the side walls of the LE and TE may be slightly undercut.

Figure 22C:
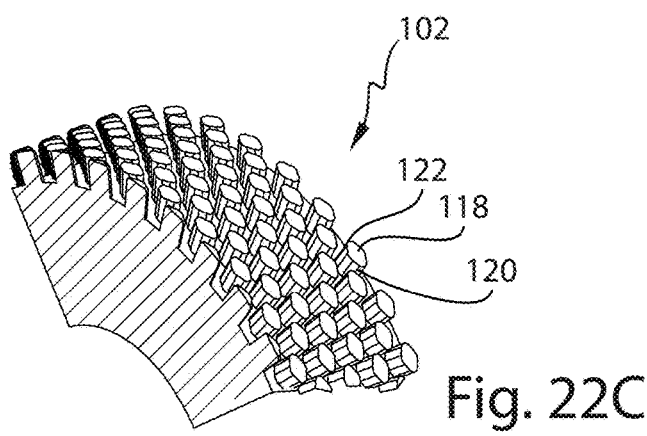
FIG. 22C is an enlarged perspective view of a portion of a male roll having an alternative configuration.
Figure 22D:
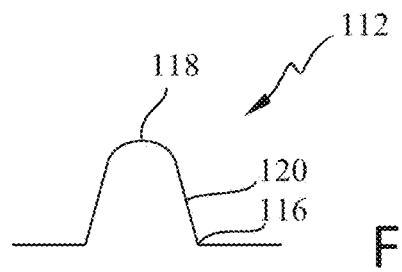
FIG. 22D is a schematic side view of a male element with a rounded top.

The transition region or "transition" 122 between the top 118 and the side walls 120 of the male elements 112 may also be of any suitable configuration. The transition 122 can be in the form of a sharp edge (as shown in FIG. 22C) in which case there is zero, or a minimal radius where the side walls 120 and the top 118 of the male elements meet. That is, the transition 122 may be substantially angular, sharp, non-radiused, or non-rounded. In other embodiments, such as shown in FIG. 22, the transition 122 between the top 118 and the side walls 120 of the male elements 112 can be radiused, or alternatively beveled. Suitable radiuses include, but are not limited to: zero (that is, the transition forms a sharp edge), 0.01 inch (about 0.25 mm), 0.02 inch (about 0.5 mm), 0.03 inch (about 0.76 mm), 0.04 inch (about 1 mm) (or any 0.01 inch increment above 0.01 inch), up to a fully rounded male element as shown in FIG. 22D.

In some cases, it may be desired to roughen the surface of all, or a portion, of the male elements 112. The surface of the male elements 112 can be roughened in any suitable manner. The surface of the male elements 112 can be roughened, for example, by: media blasting (that is, roughened with shot or "shot blasted"); wet blasting (roughed with water jets); plasma coating, machining, or knurling (i.e., pressure embossing of surface of first forming member); or combinations of the same. The roughened configuration and characteristics of the male elements 112 will depend on the type of process used to roughen the same. The roughening will typically provide at least the top 118 of at least some of the male elements 112 with greater than or equal to two discrete first surface texture elements protruding therefrom.

Figure 22E:
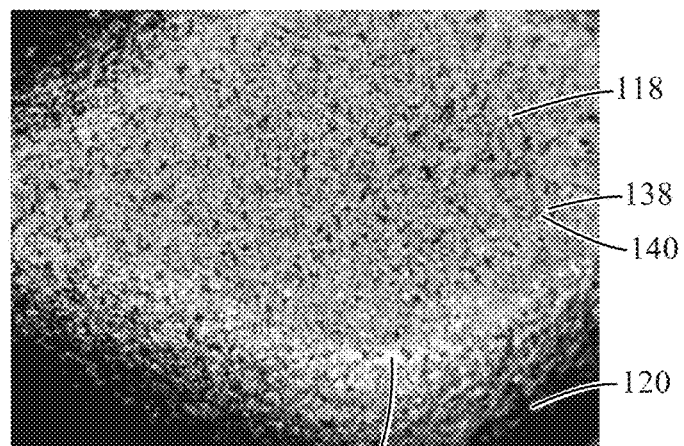
FIG. 22E is a magnified photograph of the top surface of a male element that has been roughened by sandblasting.

If a media or wet blasting process is used to roughen the surface of the male elements 112, such processes will typically form a plurality of randomly arranged pits 138 in the surface of the male elements 112 that form discrete randomly arranged raised elements or "first surface texture elements" 140 therebetween. The surface of the male elements 112, as shown in FIG. 22E, may resemble sandpaper. The surface of the male elements 112 may be described in terms of the fineness of the media used to roughen the same and/or the number of raised elements per area (such as per square inch). For example the surface of the male elements 112 may be roughened by 80, 120 or 150 grit media. The roughened surface can be described using the Surface Texture Characterization method outlined below.

Figure 22F:
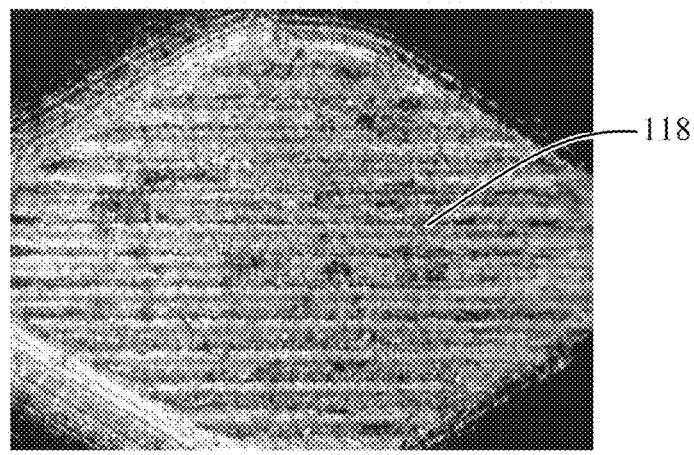
FIG. 22F is a magnified photograph of the top surface of a male element that has a relatively smooth surface formed by machining the same.
Figure 22G:
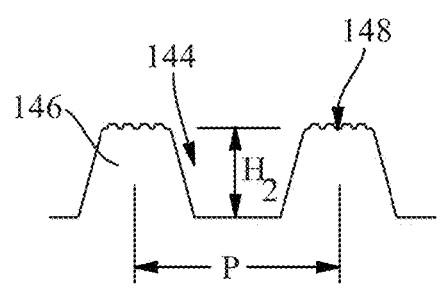
FIG. 22G is a schematic side view showing an example of macro texture and micro texture that can be created by knurling the surface of a male or female forming member.

If knurling is used to roughen the surface of the male elements 112, this will typically be performed by contacting the first forming member 102 with a rotating patterned roll made of a harder material than that of the first forming member. As shown in FIG. 22G, knurling will result in displacing material on the top surface 118 of the male elements 112 to create a pattern of valleys 144 with raised areas 146 therebetween. Knurling may modify the surface of a female forming member in the same or a similar manner. Such processes will typically form a macroscale texture (valleys 144 and raised areas 146) on the top surface 118 of the male elements 112. Such a pattern may, for example, appear in plan view as a plurality of diamond-shaped elements, diagonal lines, or straight (MD or CD) lines with a diametral pitch that may range, for example, from about 60 (coarse) to about 160 (extra fine). The macroscale texture can be characterized using a microscope with, for example, a 60× field of view. The spacing or pitch P of the elements 144 and 146 may range from about 0.5-about 2.0 mm. The height H2 of the macroscale texture elements may range from about 0.1-about 2 mm, alternatively from about 0.1-about 0.5 mm. In addition to creating a macroscale texture, the knurling process creates a microscale texture 148 on the top surfaces of the raised macroscale texture elements 146, which can be described using the Surface Texture Characterization method below.

As mentioned above, any suitable portion of the male elements 112 may be roughened. Suitable portions of the male elements that may be roughened include: the top surface 118; the side walls 120; the transition region 122 between the top surface and the side walls; or any combinations of the foregoing. For example, in some embodiments the top surface 118 and the transition region 122 may both be roughened. In other embodiments, only the transition region 122 may be roughened. Often, the portion of the male elements 112 that can be roughened will be dependent on the process used to roughen the same.

The surfaces of several rolls textured using the techniques mentioned above can be described using the Surface Texture Characterization method set out below and contrasted to non-roughened surfaces. As shown in FIG. 22F, non-roughened surfaces may comprise machining marks, such as continuous ridges and grooves, but they are very regular and have little height compared to the textured surfaces described herein. For the male rolls, analysis is made of the top surface 118 of the male elements 112 and the transition region 122 between the top surface and the side walls. For a knurled female roll, the analysis is made on the microtexture 148 that is on top of the macroscale raised texture elements 146. The data in Table 1 below includes information on various surface texture parameters, including Sq, Sxp, Str, and Vmp. Table 1 shows the Sq of a microtextured surface may have a value >1.7 μm. The Sq may be up to about 15 μm, or more. The Sxp of a microtextured surface may have a value >3.0 mm, and may be up to about 50 μm, or more. The Str of a microtextured surface may have a value >0.27 μm, and may be up to about 1.0 μm. The Vmp of a microtextured surface may have a value >0.07 mL/m$^2$, and may be up to about 1.1 mL/m$^2$, or more

TABLE 1

Surface Texture Characterization of Forming Members

| Surface | Sq (μm) | Sxp (μm) | Str | Vmp (mL/m$^2$) |
|---|---|---|---|---|
| Non-Roughened Male | | | | |
| Top surface - male element 1 | 1.41 | 2.32 | 0.12 | 0.04 |
| Top surface - male element 2 | 1.51 | 2.59 | 0.15 | 0.05 |
| Transition region | 0.86 | 1.71 | 0.25 | 0.05 |
| Media Blasted Male (150 Grit) | | | | |
| Top surface - male element 1 | 2.18 | 4.17 | 0.81 | 0.11 |
| Top surface - male element 2 | 2.17 | 4.26 | 0.96 | 0.12 |
| Transition region | 2.27 | 4.18 | 0.80 | 0.11 |
| Media Blasted Male (120 Grit) | | | | |
| Top surface - male element 1 | 3.82 | 6.76 | 0.92 | 0.18 |
| Top surface - male element 2 | 3.85 | 6.59 | 0.89 | 0.18 |
| Transition region | 3.86 | 6.87 | 0.85 | 0.19 |
| Knurled Female - Top of Knurl | | | | |
| Top of knurl - sample area 1 | 9.35 | 26.52 | 0.43 | 0.88 |
| Top of knurl - sample area 2 | 10.99 | 28.31 | 0.31 | 1.07 |
| Top of knurl - sample area 3 | 9.59 | 26.97 | 0.40 | 0.88 |

Numerous other embodiments of the male forming elements 112 are possible. In other embodiments, the top 118 of the male elements 112 can be of different shapes from those shown in the drawings. In other embodiments, the male forming elements 112 can be disposed in other orientations on the first forming member 102 rather than having their length oriented in the machine direction (including CD-orientations, and orientations between the MD and CD). The male forming elements 112 on the first forming member 102 may, but need not, all have the same configuration or properties. In certain embodiments, the first forming member 102 can comprise some male forming elements 112 having one configuration and/or properties, and other male forming elements 112 having one or more different configurations and/or properties.

The method of making the nonwoven materials may be run with the first forming member 102 and male elements 112 under any of the following conditions: at room temperature; with a chilled first forming member 102 and/or male elements 112; or with heated first forming member and/or male elements. In some cases, it may be desired to avoid heating the first forming member 102 and/or male elements 112. It may be desirable to avoid heating the first forming member and/or the male elements altogether. Alternatively, it may be desirable to avoid heating the first forming member and/or the male elements to a temperature at or above that which would cause the fibers of the nonwoven to fuse together. In some cases, it may be desirable to avoid heating the first forming member and/or the male elements to a temperature that is greater than or equal to any of the following temperatures: 130° C., 110° C., 60° C., or greater than 25° C.

Second Forming Member.

As shown in FIG. 21, the second forming member (such as "female roll") 104 has a surface 124 having a plurality of cavities or recesses 114 therein. The recesses 114 are aligned and configured to receive the male forming elements 112 therein. Thus, the male forming elements 112 mate with the recesses 114 so that a single male forming element 112 fits within the periphery of a single recess 114, and at least partially within the recess 114 in the z-direction. The recesses 114 have a plan view periphery 126 that is larger than the plan view periphery of the male elements 112. As a result, the recess 114 on the female roll may completely encompass the discrete male element 112 when the rolls 102 and 104 are intermeshed. The recesses 114 have a depth $D_1$ shown in FIG. 23. In some cases, the depth $D_1$ of the recesses may be greater than the height $H_1$ of the male forming elements 112.

The recesses 114 have a plan view configuration, side walls 128, a top edge or rim 134 around the upper portion of the recess where the side walls 128 meet the surface 124 of the second forming member 104, and a bottom edge 130 around the bottom 132 of the recesses where the side walls 128 meet the bottom 132 of the recesses.

The recesses 114 may have any suitable plan view configuration provided that the recesses can receive the male elements 112 therein. The recesses 114 may have a similar plan view configuration as the male elements 112. In other cases, some or all of the recesses 114 may have a different plan view configuration from the male elements 112.

The side walls 128 of the recesses 114 may be oriented at any suitable angle. In some cases, the side walls 128 of the recesses may be vertical. In other cases, the side walls 128 of the recesses may be oriented at an angle. Typically, this will be an angle that is tapered inwardly from the top 134 of the recess 114 to the bottom 132 of the recess. The angle of the side walls 128 of the recesses can, in some cases, be the same as the angle of the side walls 120 of the male elements 112. In other cases, the angle of the side walls 128 of the recesses can differ from the angle of the side walls 120 of the male elements 112.

Figure 23:
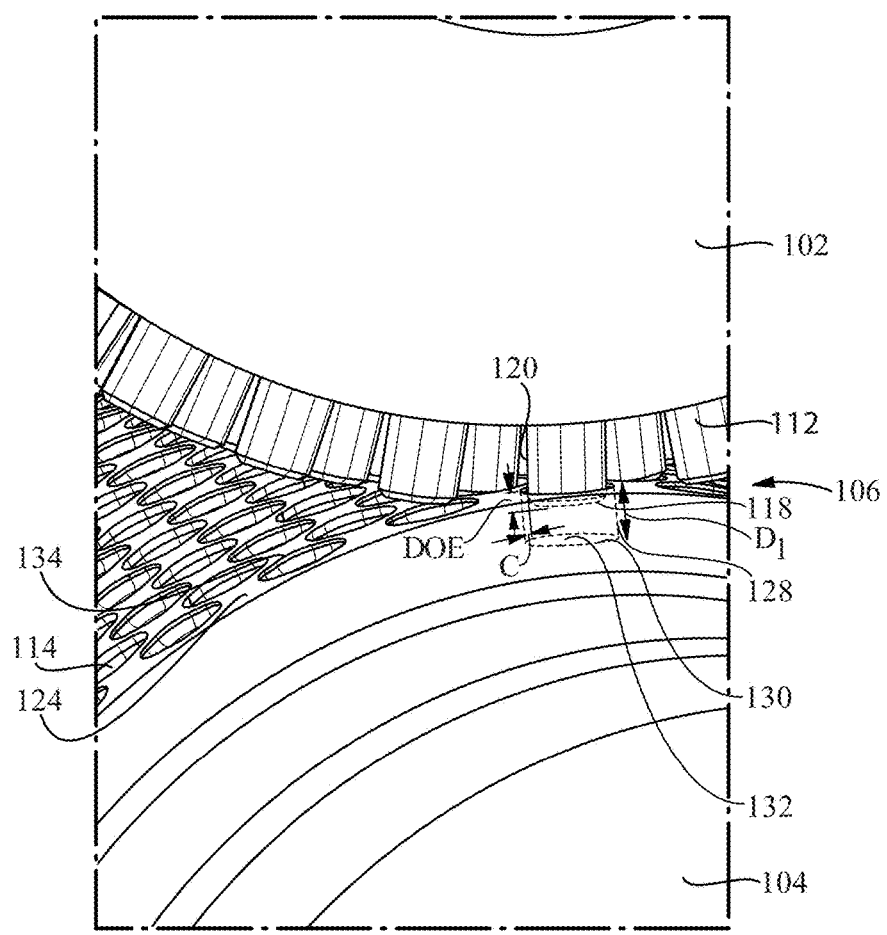
FIG. 23 is an enlarged perspective view showing the nip between the rolls shown in FIG. 21.
Figure 23A:
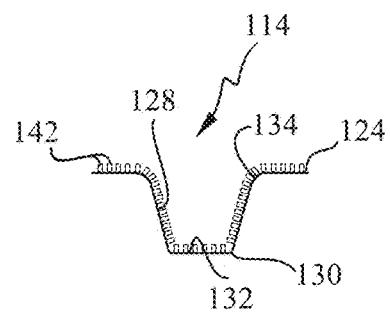
FIG. 23A is a schematic side view of a recess in a female forming member with a rounded top edge or rim.

The top edge or rim 134 around the upper portion of the recess where the side walls 128 meet the surface 124 of the second forming member 104 may have any suitable configuration. The rim 134 can be in the form of a sharp edge (as shown in FIG. 23) in which case there is zero, or a minimal radius where the side walls 128 of the recesses meet the surface of the second forming member 104. That is, the rim 134 may be substantially angular, sharp, non-radiused, or non-rounded. In other embodiments, such as shown in FIG. 23A, the rim 134 can be radiused, or alternatively beveled. Suitable radiuses include, but are not limited to: zero (that is, form a sharp edge), 0.01 inch (about 0.25 mm), 0.02 inch (about 0.5 mm), 0.03 inch (about 0.76 mm), 0.04 inch (about 1 mm) (or any 0.01 inch increment above 0.01 inch) up to a fully rounded land area between some or all of the side walls 128 around each recess 114. The bottom edge 130 of the recesses 114 may be sharp or rounded.

In some cases, it may be desired to roughen the surface of all, or a portion, of the second forming member 104 and/or recesses 114 by providing the same with a plurality of discrete second surface texture elements 142 thereon. The surface of the second forming member 104 and/or recesses 114 can be roughened in any of the manners described above for roughening the surface of the male elements 112. This may provide the surface of the second forming member 104 and/or recesses 114 with second surface texture elements 142 (and/or valleys 144, raised areas 146, and microscale texture 148 as shown in FIG. 22G) having the same or similar properties as the first surface texture elements 140 on the male elements 112. Thus, the second surface texture elements 142 can be distributed on the surface of the second forming member 104 in a regular pattern or a random pattern.

Figure 23B:
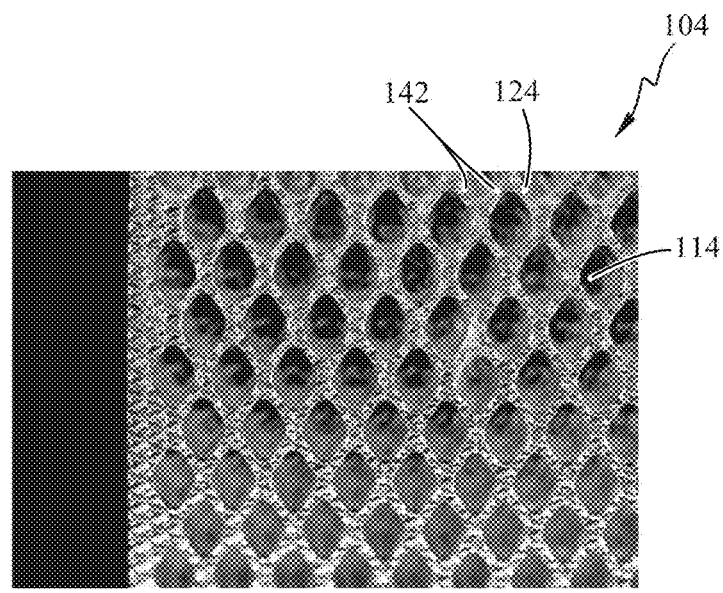
FIG. 23B is a photograph of a second forming member having a surface that has been roughened with diamond type knurling.

Any suitable portion of the second forming member 104 and/or recesses 114 may be roughened. As shown in FIG. 23A, suitable portions of the second forming member 104 and/or recesses 114 that may be roughened include: the surface 124 of the second forming member; the side walls 128 of the recesses; the top edge or rim 134 around the upper portion of the recess 114 where the side walls 128 meet the surface 124 of the second forming member 104; or any combinations of the foregoing. For example, in some embodiments the top surface 124 and the rim 134 may both be roughened. In other embodiments, only the rims 134 of the recesses 114 may be roughened. Often, the portion of the second forming member 104 and/or recesses 114 that can be roughened, as in the case of the male elements, will be dependent on the process used to roughen the same. FIG. 23B is a photograph of a second forming member 104 having a surface 124 that has been roughened with diamond type knurling.

As discussed above, the recesses 114 may be deeper than the height $H_1$ of the male elements 112 so the nonwoven material is not nipped (or squeezed) between the male and female rolls 102 and 104 to the extent possible. However, it is understood that passing the precursor web(s) between two rolls with a relatively small space therebetween will likely apply some shear and compressive forces to the web(s). The present method, however, differs from some embossing processes in which the top of the male elements compress the material to be embossed against the bottom of the female elements, thereby increasing the density of the region in which the material is compressed.

The depth of engagement (DOE) is a measure of the level of intermeshing of the forming members. As shown in FIG. 23, the DOE is measured from the top 118 of the male elements 112 to the (outermost) surface 124 of the female forming member 114 (e.g., the roll with recesses). The DOE should be sufficiently high, when combined with extensible nonwoven materials, to create protrusions 32 having a distal portion or cap 52 with a maximum width that is greater than the width of the base opening 44. The DOE may, for example, range from at least about 1.5 mm, or less, to about 5 mm, or more. In certain embodiments, the DOE may be between about 2.5 mm to about 5 mm, alternatively between about 3 mm and about 4 mm. The formation of protrusions 32 having a distal portion with a maximum width that is greater than the width of the base opening 44 is believed to differ from most embossing processes in which the embossments typically take the configuration of the embossing elements, which have a base opening that is wider than the remainder of the embossments.

As shown in FIG. 23, there is a clearance, C, between the sides 120 of the male elements 112 and the sides (or side walls) 128 of the recesses 114. The clearances and the DOE's are related such that larger clearances can permit higher DOE's to be used. The clearance, C, between the male and female roll may be the same, or it may vary around the perimeter of the male element 112. For example, the forming members can be designed so that there is less clearance between the sides of the male elements 112 and the adjacent side walls 128 of the recesses 114 than there is between the side walls at the end of the male elements 112 and the adjacent side walls of the recesses 114. In other cases, the forming members can be designed so that there is more clearance between the sides 120 of the male elements 112 and the adjacent side walls 128 of the recesses 114 than there is between the side walls at the end of the male elements 112 and the adjacent side walls of the recesses. In still other cases, there could be more clearance between the side wall on one side of a male element 112 and the adjacent side wall of the recess 114 than there is between the side wall on the opposing side of the same male element 112 and the adjacent side wall of the recess. For example, there can be a different clearance at each end of a male element 112; and/or a different clearance on each side of a male element 112. Clearances can range from about 0.005 inches (about 0.1 mm) to about 0.1 inches (about 2.5 mm).

Some of the aforementioned male element 112 configurations alone, or in conjunction with the second forming member 104 and/or recess 114 configurations may provide additional advantages. This may be due to by greater lock of the nonwoven material on the male elements 112, which may result in more uniform and controlled strain on the nonwoven precursor material. This may produce more well-defined protrusions 32 and a stronger visual signal for consumers, giving the appearance of softness, absorbency, and/or dryness.

The precursor nonwoven web 30 is placed between the forming members 102 and 104. The precursor nonwoven web can be placed between the forming members with either side of the precursor web (first surface 34 or second surface 36) facing the first forming member, male forming member 102. For convenience of description, the second surface 36 of the precursor nonwoven web will be described herein as being placed in contact with the first forming member 102. (Of course, in other embodiments, the second surface 36 of the precursor nonwoven web can be placed in contact with the second forming member 104.)

The precursor material is mechanically deformed with the forming members 102 and 104 when a force is applied on the nonwoven web with the forming members 102 and 104. The force can be applied in any suitable manner. If the forming members 102 and 104 are in the form of plates, the force will be applied when the plates are brought together. If the forming members 102 and 104 are in the form of counter-rotating rolls (or belts, or any combination of rolls and belts), the force will be applied when the precursor nonwoven web passes through the nip between the counter-rotating elements. The force applied by the forming members impacts the precursor web and mechanically deforms the precursor nonwoven web.

Numerous additional processing parameters are possible. If desired, the precursor nonwoven web may be heated before it is placed between the forming members 102 and 104. If the precursor nonwoven web is a multi-layer structure, any layer or layers of the same can be heated before the layers are combined. Alternatively, the entire multi-layer nonwoven web can be heated before it is placed between the forming members 102 and 104. The precursor nonwoven web, or layer(s) of the same, can be heated in any suitable manner including, but not limited to using conductive heating (such as by bringing the web(s) in contact with heated rolls), or by convective heating (i.e., by passing the same under a hot air knife or through an oven). The heating should be non-targeted, and without the help of any agent. The first forming member 102 and/or second forming member 104 (or any suitable portion thereof) can also be heated. If desired, the web could be additionally, or alternatively, heated after it is mechanically deformed.

If the precursor material is fed between forming members comprising counter-rotating rolls, several processing parameters may be desirable. With regard to the speed at which the precursor web is fed between the counter-rotating rolls, it may be desirable to overfeed the web (create a negative draw) going into the nip 106 between the rolls. The surface speed of the metering roll immediately upstream of the forming members 102 and 104 may be between about 1 and 1.2 times the surface speed of the forming members 102 and 104. It may be desirable for the tension on the precursor web immediately before forming members 102 and 104 to be less than about 5 lbs. force (about 22 N), alternatively less than about 2 lbs. force (about 9 N) for a web width of 0.17 m. With regard to the speed at which the deformed web 30 is removed from between the counter-rotating rolls, it may be desirable to create a positive draw coming out of the nip between the rolls. The surface speed of the metering roll immediately downstream of the forming members 102 and 104 may be between about 1 and 1.2 times the surface speed of the forming members 102 and 104. It may be desirable for the tension on the web immediately after the forming members 102 and 104 to be less than about 5 lbs. force (about 22 N), alternatively less than about 2 lbs. force (about 9 N).

Figure 24A:
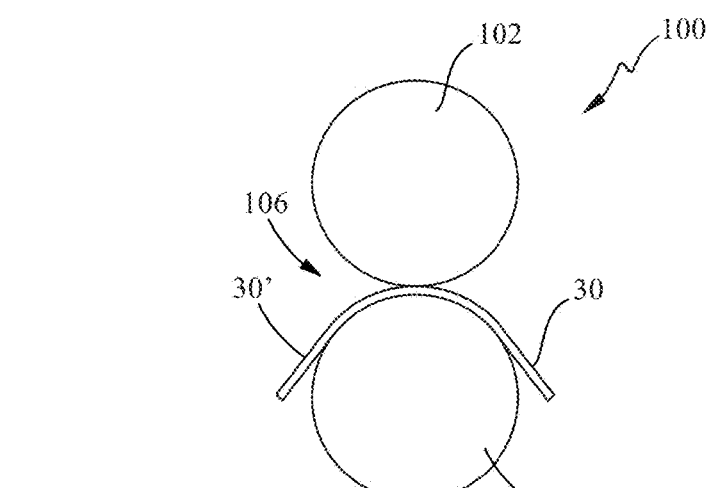
FIG. 24A is a schematic side view of an apparatus for forming the nonwoven material in which the web wraps around one of the rolls before and after passing through the nip between the rolls.

As shown in FIG. 24A, rather than feeding the precursor web 30' into the nip 106 between the forming members 102 and 104 without the precursor web 30' contacting any portion of the forming members prior to or after the nip, it may be desirable for the web to pre-wrap the second forming member 104 prior to entering the nip 106, and for the web 30 to post wrap second forming member 104 after passing through the nip.

The apparatus 100 for deforming the web can comprise multiple nips for deforming portions of the web in the same location such as described in U.S. Patent Publication No. US 2012/0064298 A1, Orr, et al. For example, the apparatus may comprise a central roll and satellite rolls with equal DOE or progressively greater DOE with each successive roll. This can provide benefits such as reducing damage to the web and/or helping to further ensure that the deformations are permanently set in the web thereby preventing the web from recovering toward its undeformed condition.

The apparatus for deforming the web can also comprise belts, or other mechanisms, for holding down the longitudinal edges of the web to prevent the web from being drawn inward in the cross-machine direction.

When deforming multiple webs that are laminated together with an adhesive, it may be desirable to chill the forming members in order to avoid glue sticking to and fouling the forming members. The forming members can be chilled using processes know in the art. One such process could be an industrial chiller that utilizes a coolant, such as propylene glycol. In some cases, it may be desirable to operate the process in a humid environment such that a layer of condensate forms on the forming members.

The apparatus 100 for deforming the web can be at any suitable location in any suitable process. For example, the apparatus can be located in-line with a nonwoven web making process or a nonwoven laminate making process. Alternatively, the apparatus 100 can be located in-line in an absorbent article converting process (such as after the precursor web is unwound and before it is incorporated as part of the absorbent article).

The process forms a nonwoven web 30 comprising a generally planar first region 40 and a plurality of discrete integral second regions 42 that comprise deformations comprising protrusions 32 extending outward from the first surface 34 of the nonwoven web and openings in the second surface 36 of the nonwoven web. (Of course, if the second surface 36 of the precursor nonwoven web is placed in contact with the second forming member 104, the protrusions will extend outward from the second surface of the nonwoven web and the openings will be formed in the first surface of the nonwoven web.) Without wishing to be bound by any particular theory, it is believed that the extensibility of the precursor web (or at least one of the layers of the same) when pushed by the male forming elements 112 into the recesses 114 with depth of engagement DOE being less than the depth $D_1$ of the recesses, stretches a portion of the nonwoven web to form a deformation comprising a protrusion with the enlarged cap and wide base opening described above. (This can be analogized to sticking one's finger into an uninflated balloon to stretch and permanently deform the material of the balloon.)

In cases in which the precursor nonwoven material 30' comprises more than one layer, and one of the layers is in the form of discrete pieces of nonwoven material, as shown in FIG. 24, it may be desirable for the deformations to be formed so that the base openings 44 are in the continuous layer (such as 30B) and the protrusions 32 extend toward the discrete layer (such as 30A). Of course, in other embodiments, the deformations in such a structure can be in the opposite orientation. The deformations can be distributed in any suitable manner over the surfaces of such continuous and discrete layers. For example, the deformations can: be distributed over the full length and/or width of the continuous layer; be distributed in an area narrower than the width of the continuous layer; or be limited to the area of the discrete layer.

The method of deforming the nonwoven materials described herein may exclude (or be distinguishable from) the following processes: hydroforming (hydroentangling); hydromolding; use of air jets; rigid-to-resilient (e.g., steel/rubber) embossing; and the use of a patterned surface against a flat anvil surface (e.g., rigid-to-rigid embossing). The method may also exclude (or be distinguishable from) The Procter & Gamble Company's processes for making Structural Elastic-Like Films ("SELF" processes). The forming members used herein differ from the forming members used in SELFing processes to form corrugated structures (and tufted structures) in that the SELF teeth typically have a comparatively small diameter tip, and the ridges of the mating ring roll only border the SELF teeth on the sides, and not the front and back of the teeth.

IV. Optional Processing Steps

The precursor web material 30' and/or the nonwoven web material 30 with deformations therein can be subjected to an optional additional processing step. The additional steps can include, but are not limited to embossing and/or bonding.

A. Embossing.

The precursor web material 30' and/or the nonwoven web material 30 with deformations therein can be subjected to an optional embossing step. The precursor web material 30' can be embossed prior to the formation of deformations therein. In addition, or alternatively, the nonwoven web materials 30 described herein may be embossed after the formation of deformations (protrusions 32 and base openings 44) therein.

The embossments can be provided in any known manner. Suitable embossing methods include, but are not limited to rigid-to-resilient and rigid-to-rigid methods described in the preceding section. If the precursor nonwoven material or the nonwoven web materials 30 with deformations therein are embossed, the embossments can be positioned in a specific location relative to the deformations. That is, the embossments may be registered with the deformations. In other embodiments, the embossments may be randomly positioned relative to the deformations.

B. Optional Bonding Steps.

1. Bonding Together Portions of a Deformed Nonwoven Material.

a) Tip Bonding of a Deformed Nonwoven Material.

One optional bonding step involves bonding portions of the deformed nonwoven material 30 together at the tops or distal ends 54 of the protrusions 32 ("tip bonding"). If the deformed nonwoven material 30 is a single layer material, then this step will bond the fibers in the layer together at the distal ends 54 of the protrusions 32. If the deformed nonwoven material 30 is a dual or multiple layer nonwoven material, then this step will bond the fibers together at the distal ends 54 of the protrusions 32 and will also bond fibers in each of the layers together at the distal ends 54 of the protrusions 32.

Figure 28:
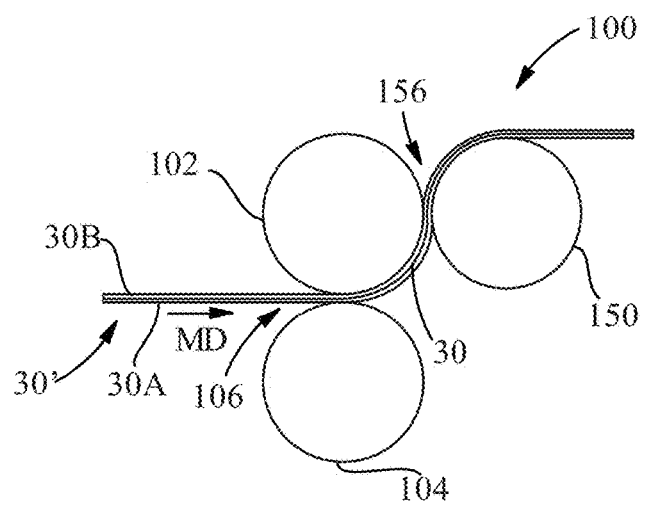
FIG. 28 is a schematic side view of an apparatus for forming the nonwoven material which includes an additional roll for tip bonding the layers of a multiple layer nonwoven material.

FIG. 28 shows one embodiment of an apparatus 100 for deforming the nonwoven material which includes an additional bonding roll 150 for tip bonding the deformed nonwoven material 30. As shown in FIG. 28, a precursor web 30' is fed into the deforming nip 106 between first forming roll 102 and second forming roll 104. After leaving the deforming nip 106, the deformed web 30 is wrapped partially around the first forming roll, male roll 102. Vacuum, hold down belts, or some other mechanism could be used to keep the deformed web 30 seated on the first forming roll 102. While the web 30 is still in contact with the male roll 102, it passes through a second nip 156 between male roll 102 and the additional bonding roll 150. The additional bonding roll 150 can compress the fibers at the distal ends 54 of the protrusions 32 sufficient to partially melt and bond the fibers at this location together. The bonding roll 150 may be heated to help facilitate bonding. Alternatively, ultrasonics could be used to facilitate bonding. In the case of at least some of the precursor materials described herein, the materials can be bonded together if the bonding roll 150 surface temperature is between about 120° F. (about 50° C.) and about 270° F. (about 130° C.). Upon exit of the second nip 156, the web may wrap the bonding roll 150 as shown in FIG. 28, or it may wrap the male roll 102.

Figure 29:
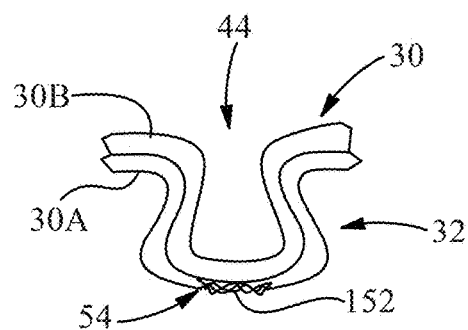
FIG. 29 is a schematic cross-sectional view of a tip bonded protrusion (shown oriented downward) made by the apparatus shown in FIG. 28.

As shown in FIG. 29, this produces a protrusion 32 in which the layers are bonded together at the tops (or distal ends 54) of the protrusions 32. This will form a tip bonded portion 152. The tip bonded portion 152 (and the bonds formed in the other optional post bonding steps described herein) will often differ in at least one of: size (that is, they may be larger), shape, and location from any thermal point bonds present in spunbonded nonwoven layers. The post deformation bond sites will typically be registered with the deformations in the deformed nonwoven, while thermal point bonds are provided in a separate and different pattern in a spunbonded precursor web. The bonding may result in a more translucent (film-like) bonded portion 152. Placing a layer containing color adjacent to the deformed material 30 could result in color showing through primarily in the translucent bonded portion 152, highlighting the protrusion 32.

Without wishing to be bound by any particular theory, it is believed that bonding the layers together at the distal ends 54 of the protrusions 32 may provide benefits which include: 1) increased perception of the depth of the base openings 44 when the base openings are oriented toward the consumer, as well as 2) improved dryness (by reducing the hang-up of fluid in the bottoms of the protrusions when the base openings 44 are oriented toward the consumer); and 3) reduction or elimination of the need to glue or otherwise bond the layers of a dual or multilayer precursor web together.

b) Base Bonding of a Deformed Nonwoven Material.

Another optional bonding step involves bonding portions of the deformed nonwoven material 30 together at base bond sites in the undeformed first region 40 outside of the bases 50 of the protrusions 32 ("base bonding"). If the deformed nonwoven material 30 is a single layer material, then this step will bond the fibers of the layer together in the undeformed first region 40 outside of the bases 50 of the protrusions 32. If the deformed nonwoven material 30 is a dual or multiple layer nonwoven material, then this step will bond the fibers together in the undeformed first region 40 outside of the bases of the protrusions 32 and will also bond fibers in each of the layers together in the undeformed first region 40 outside of the bases of the protrusions 32.

Figure 32:
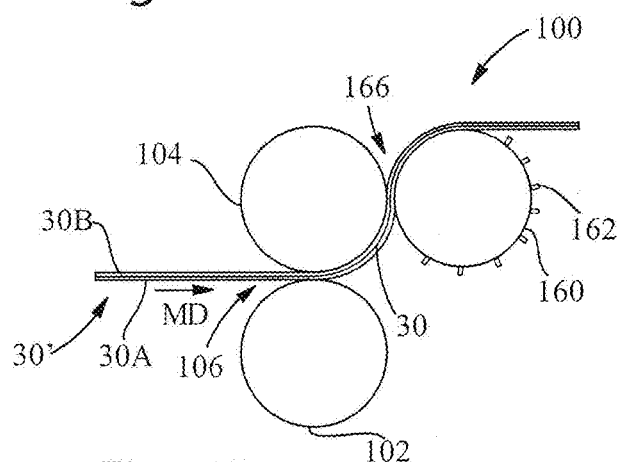
FIG. 32 is a schematic side view of an apparatus for deforming the nonwoven material which includes an additional roll for base bonding the deformed nonwoven material.

FIG. 32 shows one embodiment of an apparatus 100 for deforming the nonwoven material which includes an additional bonding roll 160 for base bonding the deformed nonwoven material 30. In FIG. 32, the position of first and second forming rolls 102 and 104 are reversed and the female roll 104 is located on top of the male roll 102. However, in other embodiments, the male roll 102 could be on top as shown in the tip bonding roll arrangements described above. A precursor nonwoven web 30' is fed into the deforming nip 106 between first forming roll 102 and second forming roll 104. After leaving the deforming nip 106, the deformed web 30 is wrapped partially around the second forming roll, female roll 104. Vacuum, hold down belts, or some other mechanism could be used to keep the deformed web 30 seated on the second forming roll 104. While the web 30 is still in contact with the female roll 104, it passes through a second nip 166 between female roll 104 and the additional bonding roll 160. The additional bonding roll 160 can compress the fibers in the undeformed first region 40 outside of the bases 50 of the protrusions 32 sufficient to partially melt and bond the fibers at this location together. The bonding roll may be heated to facilitate bonding in the case of at least some of the precursor materials described herein. Ultrasonics may also be used to facilitate bonding. Upon exit of the second nip 166, the web may wrap the bonding roll 160 as shown in FIG. 32, or it may wrap the female roll 104.

Figure 35A:
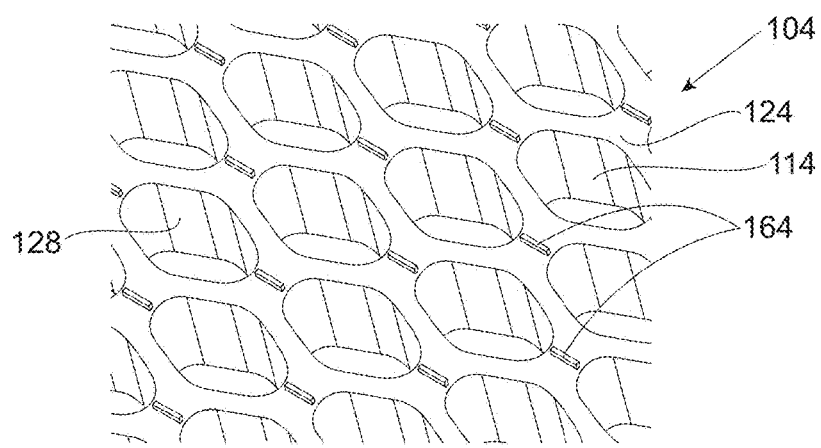
FIG. 35A is an enlarged perspective view of a portion of one embodiment of a female roll having a plurality of discrete bonding elements on its surface.
Figure 35B:
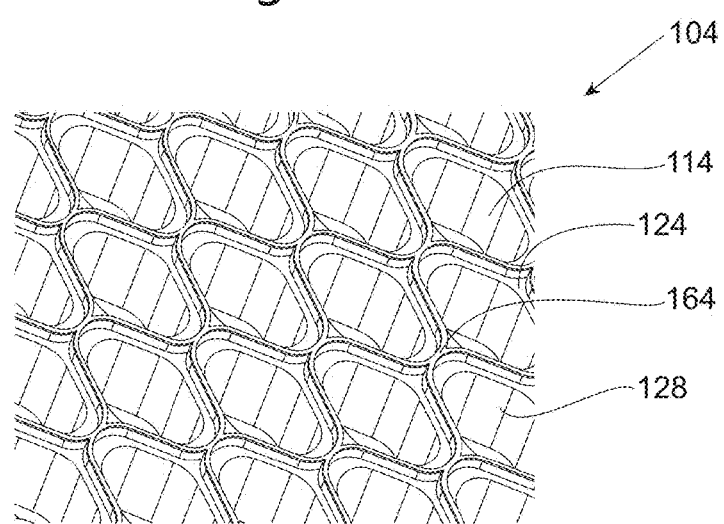
FIG. 35B is an enlarged perspective view of a portion of one embodiment of a female roll having continuous bonding elements on its surface.
Figure 35C:
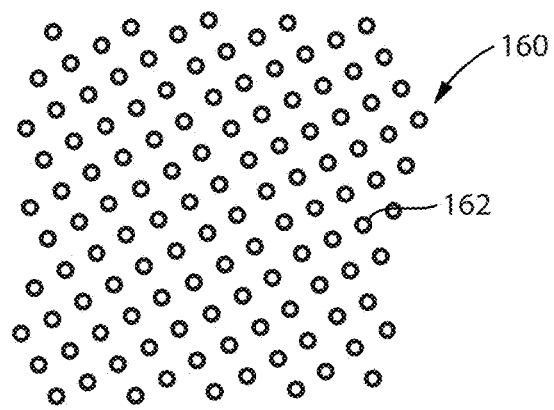
FIG. 35C is a plan view of a portion of the surface of one embodiment of a bonding roll with a plurality of discrete bonding elements thereon.
Figure 36:
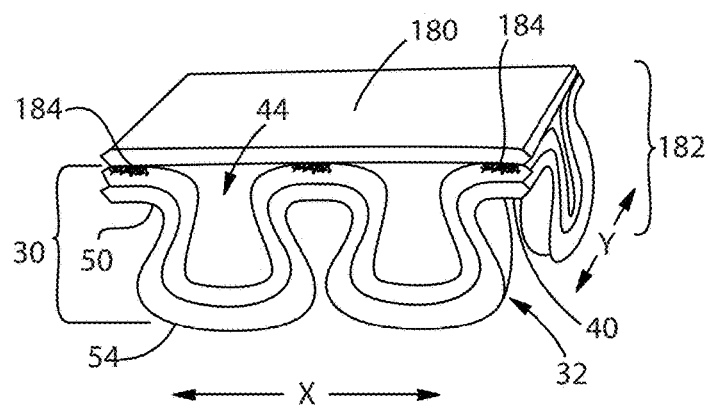
FIG. 36 is a schematic perspective view of a portion of a deformed nonwoven web that is base bonded to an additional layer (only a portion of the additional layer is shown) made by the apparatus shown in FIG. 35.

There are a number of variations of the roll configurations in the bonding step. The surface of the bonding roll 160 may be substantially smooth. Alternatively, as shown in FIGS. 32 and 35C, it can have a plurality of discrete, spaced-apart bonding elements 162 protruding from its surface. The portions of the surface 124 of the female roll 104 that are located outside of the recesses 114 in the female roll 104 may also be substantially smooth, or they may have a plurality of discrete, spaced-apart bonding elements 164 protruding from the surface 124. The bonding elements 164 on the surface 124 of the female roll 104 may be discrete, spaced-apart bonding elements 164 as shown in FIG. 35A, or they may be continuous bonding elements 164 as shown in FIG. 35B.

In those cases in which the surface of the bonding roll 160 is substantially smooth, the base bond sites 168 may be at least substantially continuous and may substantially or completely surround the deformations in the web 30. FIG. 33A shows a web having continuous base bond sites 168. FIG. 33B is a cross-section of the web shown in FIG. 33A.

As shown in FIG. 34, in those cases in which the bonding roll 160 or the female roll 104 have a plurality of discrete, spaced-apart bonding elements 162 and 164, respectively, protruding from their surfaces, the bonding elements will only bond discrete, spaced-apart regions of the web 30 in the undeformed first region 40 outside of the bases 50 of the protrusions 32. In such case, the base bonds 168 may be located in at least two discrete portions of the first region 40 which are adjacent to and lie outside of at least some of the deformations. In other words, in such cases there may be at least two base bond sites 168 for a given deformation.

c) Tip and Base Bonding.

In another embodiment, the deformed nonwoven material 30 can be both tip and base bonded. This can be done in a process that is a combination of the processes shown in FIGS. 28 and 32.

Figure 40:
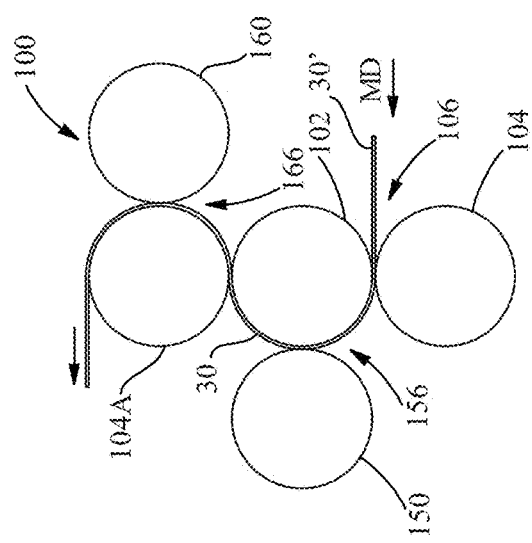
FIG. 40 is a schematic side view of an apparatus for deforming the nonwoven material which includes additional rolls for tip bonding and base bonding the deformed nonwoven material.

FIG. 40 shows one embodiment of an apparatus 100 for carrying out such a process. The rolls 102, 104, and 150 comprise the tip bonding portion of the apparatus, which is similar to the apparatus shown in FIG. 28. FIG. 40 differs in that the precursor web 30' is shown as being fed into the deforming nip 106 from the right side in FIG. 40, instead of the left side, and the deformed web 30 wraps around male roll 102 instead of bonding roll 150 after it leaves the deforming nip 106. Therefore, the description of this portion of the apparatus will incorporate the above description of the apparatus shown in FIG. 28, and will not be repeated in its entirety herein. The apparatus shown in FIG. 40 further comprises a second female roll 104A and a base bonding roll 160. The male roll 102, the second female roll 104A, and the base bonding roll 160 comprise the base bonding portion of the apparatus, which is similar to the apparatus shown in FIG. 32. FIG. 40 differs in that the deformed bonded web 30 is shown as wrapping around the second female roll 104A as it leaves the apparatus in FIG. 40, instead of wrapping around the base bonding roll 160. Therefore, the description of this portion of the apparatus will incorporate the above description of the apparatus shown in FIG. 32, and will not be repeated in its entirety herein.

As shown in FIG. 40, the precursor web 30' is fed into the deforming nip 106 between first forming roll 102 and second forming roll 104. After leaving the deforming nip 106, the deformed web 30 is wrapped partially around the first forming roll, male roll 102. While the web 30 is still in contact with the male roll 102, it passes through a second nip 156 between male roll 102 and the additional bonding roll 150. The additional bonding roll 150 can compress the fibers at the distal ends 54 of the protrusions 32 sufficient to partially melt and bond the fibers at this location together. Heat and/or ultrasonics may also be used to help facilitate bonding. As shown in FIG. 29, this produces a protrusion 32 in which the deformed nonwoven material 30 is bonded together at the tops (or distal ends 54) of the protrusions 32. The deformed tip bonded web 30 then passes between male roll 102 and second female roll 104A. After that, the deformed tip bonded web 30 is wrapped partially around the second female roll 104A. While the web 30 is still in contact with the second female roll 104A, it passes through a second nip 166 between the second female roll 104A and the additional bonding roll 160. The additional bonding roll 160 can compress the fibers in the undeformed first region 40 outside of the bases 50 of the protrusions 32 sufficient to partially melt and bond the fibers at this location together. Heat and/or ultrasonics may also be used to help facilitate bonding. This will provide the tip bonded web with base bonds 168 which may be continuous as shown in FIG. 33A, or discrete as shown in FIG. 34.

2. Bonding the Nonwoven Materials to an Additional Layer.

In other embodiments, a deformed nonwoven material can be bonded to another material to form a composite web or sheet. The term "sheet" will be used herein to refer to a portion (e.g., a discrete length) of a web that has been cut into an individual piece from the web, typically as a final step in a manufacturing process. Therefore, if a property is described herein as being present in the composite web, it will also be present in the composite sheet. The components of the composite sheet may be described as being "partially bonded" together. By this it is meant that the components are bonded together at certain locations on their surfaces, and are not bonded together over their entire surfaces. The components of the composite sheet in any of the embodiments described herein can be bonded together using any suitable type of bonding process including, but not limited to ultrasonics, adhesives, and heat and/or pressure, or combinations of the same.

a) Tip Bonding.

In some embodiments, a deformed nonwoven material can be bonded to another material to form a composite web or sheet by bonding the layers together at the tops or distal ends 54 of the protrusions 32 of the deformed nonwoven material.

Figure 30:
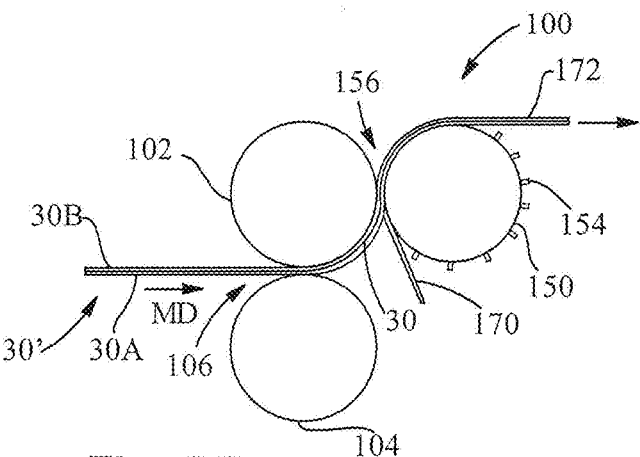
FIG. 30 is a schematic side view of an apparatus for tip bonding the deformed nonwoven material to an additional layer.

FIG. 30 shows one embodiment of an apparatus 100 similar to that shown in FIG. 28. The apparatus shown in FIG. 30 deforms the nonwoven material and also includes an additional bonding roll 150. In this embodiment, the bonding roll 150 is used for bonding the deformed nonwoven material 30 to an additional layer 158 at the distal ends 54 of the protrusions 32 in the deformed nonwoven material 30. As shown in FIG. 30, the additional bonding roll 150 is located downstream of the first nip, deforming nip 106. The bonding roll 150 can have any suitable surface configuration. In some embodiments, the surface of the bonding roll 150 may be substantially smooth. In other cases, the bonding roll 150 may have a plurality of bonding elements 154 protruding from the surface of the bonding roll 150. The second nip 156 is formed between the male roll 102 and the bonding roll 150.

The nonwoven web with deformations therein, which comprises a first web 30, and a second nonwoven web 170 are fed into the second nip 156. Vacuum, hold down belts, or some other mechanism could be used to keep the deformed web 30 seated on the first forming roll 102 as it is transferred to the second nip 156. The nonwoven web 30 with deformations therein can be a single layer nonwoven web or a dual or multiple layer nonwoven web. The second nonwoven web 170 can comprise any of the types of nonwoven webs specified as being suitable for use as precursor webs for the nonwoven material. The second nonwoven web 170, however, need not be deformed as in the case of the first web 30, and thus may be substantially planar. In some embodiments, at least one of the first web 30 and second web 170 comprises a spunbond nonwoven which has discrete bond sites 46 therein. The first web 30 can have any of the characteristics of the deformed nonwoven materials described herein (e.g., one or more layers, bulbous protrusions, bond sites, areas with different fiber concentration, etc.). The bonding roll 150 can have any other properties (heated or unheated) and manner of bonding (compression and/or melting) in the tip bonding process described above. In addition, adhesive may be applied to the second nonwoven web 170 prior to the second nip 156 in order to facilitate bonding.

The second nip 156 bonds at least a portion of the distal ends 54 of the protrusions in the first web 30 to the second web 170 to form a tip-bonded composite web 172 in which the first and second webs are bonded together at inter-web bond sites 174. The first web 30 has a first region 40 that can be considered to have an X-direction orientation (which may be in the machine direction), a Y-direction orientation (which may be in the cross-machine direction), and the protrusions 32 extend outward therefrom in the Z-direction. The inter-web bond sites 174 are spaced apart in the X-direction and the Y-direction so that the composite web 172 has unbonded regions between the inter-web bond sites 174 in all directions. This differs from corrugated materials which typically contact and are bonded to a second layer along the length of the corrugations rather than at discrete bond sites.

The inter-web bond sites 174 comprise bonded portions of the protrusions 32. In some embodiments, the bonded portions 174 of the protrusions 32 may comprise fibers that are more densely packed than the fibers in the first region 40 of the first web or sheet 30. In some cases, at least portions of the fibers in the bonded portions 174 of the protrusions 32 may be melted. In those cases in which the surface of the bonding roll 150 is substantially smooth, the inter-web bond sites 174 will be formed on substantially the entire distal ends 54 of the protrusions 32 in the first web 30. In those cases in which the bonding roll 150 has a plurality of discrete, spaced-apart bonding elements 154 protruding from the surface of the bonding roll 150, the bonding elements 154 will only bond a portion of the distal ends 54 of the protrusions 32 in the first web 30. In some cases, the inter-web bond sites 174 can be formed in less than or equal to 25% of the area on the distal ends 54 of the protrusions 32.

Forming a composite sheet by bonding the deformed nonwoven material 30 to another layer or material is believed to improve the resiliency of the deformed web material 30 to compressive forces.

b) Base Bonding.

In still other embodiments, the deformed nonwoven material 30 can be bonded to another material to form a composite sheet by bonding the layers together at the base of the protrusions of the deformed nonwoven material. The layers of the composite sheet can be bonded together using any suitable type of bonding process including, but not limited to ultrasonics, adhesives, and heat and/or pressure, or combinations of the same.

FIG. 35 shows one embodiment of an apparatus 100 for deforming the nonwoven material which includes an additional bonding roll 160 for bonding the deformed nonwoven material 30 to an additional layer outside the base 50 of the protrusions 32 of the deformed nonwoven material 30. As shown in FIG. 35, the additional bonding roll 160 is located downstream of the first nip 106. The second nip 166 is formed between the female roll 104 and the bonding roll 160.

The nonwoven web 30 with deformations therein, which comprises a first sheet and a second nonwoven web 180 are fed into the second nip 166. Vacuum, hold down belts, or some other mechanism could be used to keep the deformed web 30 seated on the female roll 104 as it is transferred to the second nip 166. The nonwoven web 30 with deformations therein can be a single layer nonwoven web or a dual or multiple layer nonwoven web. The second nonwoven web 180 can comprise any of the types of nonwoven webs specified as being suitable for use as precursor webs for the nonwoven material and can have any of the properties of the second nonwoven web 170 in the tip bonding process (of the deformed nonwoven to an additional layer) described above.

The second nip 166 bonds at least a portion of the deformed nonwoven web 30 outside the base 50 of the protrusions 32 in the first web 30 to the second web 180 to form a base-bonded composite web or sheet 182 in which the first and second webs are bonded together at inter-web bond sites 184. As in the case of the tip bonding process, the inter-web bond sites 184 are spaced apart in the X-direction and the Y-direction.

The inter-web bond sites 184 comprise bonded portions at the base 50 of the protrusions 32 outside of the deformations and in the first region 40 of the first web 30 to form a base-bonded composite web 182. In some embodiments, the base bonded portions 184 may comprise fibers that are more densely packed than the fibers in the first region 40 of the first web 30. In some cases, at least portions of the fibers in the base bonded portions 184 of the first web 30 may be melted.

There are a number of variations of the roll configurations in the bonding step. The surface of the bonding roll 160 may be substantially smooth. Alternatively, as shown in FIGS. 35 and 35C, it can have a plurality of discrete, spaced-apart bonding elements 162 protruding from its surface. The portions of the surface 124 of the female roll 104 that are located outside of the recesses 114 in the female roll 104 may also be substantially smooth, or they may have a plurality of discrete, spaced-apart bonding elements 164 protruding from the surface 124. The bonding elements 164 on the surface 124 of the female roll 104 may be discrete, spaced-apart bonding elements 164 as shown in FIG. 35A, or they may be continuous bonding elements 164 as shown in FIG. 35B.

In those cases in which the surface of the bonding roll 160 is substantially smooth, the inter-web bond sites 184 may be at least substantially continuous and may substantially or completely surround the deformations in the first web 30 similar to the base bond sites 168 shown in FIG. 33A.

In those cases in which the bonding roll 160 or the bonding roll 104 have a plurality of discrete, spaced-apart bonding elements 162 and 164, respectively, protruding from their surfaces, the bonding elements will only bond discrete, spaced-apart regions of the first web 30 (that lie outside of the deformations) to the second web 180. In such cases, the inter-web bonds 184 may be located in at least two discrete portions of the first region 40 which are adjacent to and lie outside of at least some of the deformations. Thus, in such cases there may be at least two inter-web base bond sites 184 for a given deformation similar to the base bond sites 168 shown in FIG. 34.

c) Tip and Base Bonding.

In other embodiments, the deformed nonwoven material 30 can be tip bonded or base bonded as described above, and then also bonded to another material to form a composite web or sheet.

Figure 41:
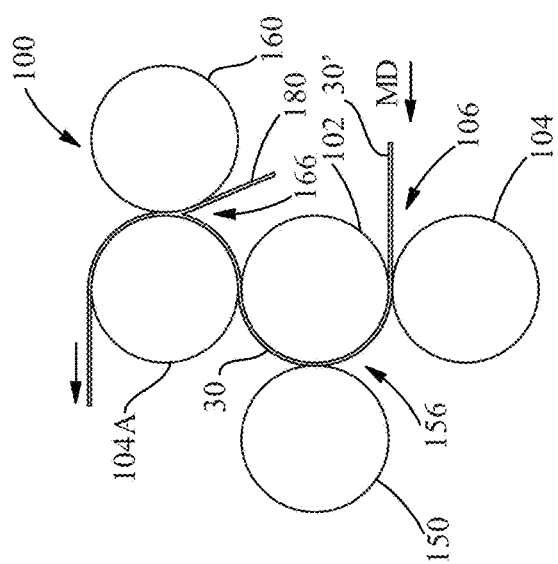
FIG. 41 is a schematic side view of an apparatus for deforming the nonwoven material which includes additional rolls for tip bonding the deformed nonwoven material and then base bonding the deformed nonwoven material to an additional layer.

FIG. 41 shows one embodiment of an apparatus 100 for carrying out a tip bonding process in which the tip bonded deformed nonwoven web 30 is then base bonded to another material to form a composite web or sheet. The apparatus 100 shown in FIG. 41 is similar to the apparatus shown in FIG. 40. FIG. 41 differs from the apparatus shown in FIG. 40 in that an additional layer 180 is fed into the apparatus and is bonded to the deformed nonwoven material 30 outside the base 50 of the protrusions 32 of the deformed nonwoven material 30. This aspect of the apparatus shown in FIG. 41 (feeding an additional layer for base bonding) is similar to that shown in FIG. 35. Therefore, the description of the apparatus shown in FIG. 41 will incorporate the above descriptions of the apparatuses shown in FIGS. 35 and 40, and will not be repeated in its entirety herein.

As shown in FIG. 41, the precursor web 30' is fed into the deforming nip 106 between first forming roll 102 and second forming roll 104. After leaving the deforming nip 106, the deformed web 30 is wrapped partially around the first forming roll, male roll 102. While the web 30 is still in contact with the male roll 102, it passes through a second nip 156 between male roll 102 and the additional bonding roll 150. The additional bonding roll 150 can compress the fibers at the distal ends 54 of the protrusions 32 sufficient to partially melt and bond the fibers at this location together. As shown in FIG. 29, this produces a protrusion 32 in which the deformed nonwoven material 30 is bonded together at the tops (or distal ends 54) of the protrusions 32. The deformed tip bonded web 30 then passes between male roll 102 and second female roll 104A. After that, the deformed tip bonded web 30 is wrapped partially around the second female roll 104A. While the web 30 is still in contact with the second female roll 104A, it passes through a second nip 166 between the second female roll 104A and the additional bonding roll 160. The second nip 166 bonds at least a portion of the deformed nonwoven web 30 outside the base 50 of the protrusions 32 in the first web 30 the second web 180 to form a base-bonded composite web or sheet 182 in which the first and second webs are bonded together at inter-web bond sites 184. The inter-web base bonds 184 may be continuous similar to the base bonds 168 shown in FIG. 33A, or discrete similar to the base bonds 168 shown in FIG. 34.

Figure 42:
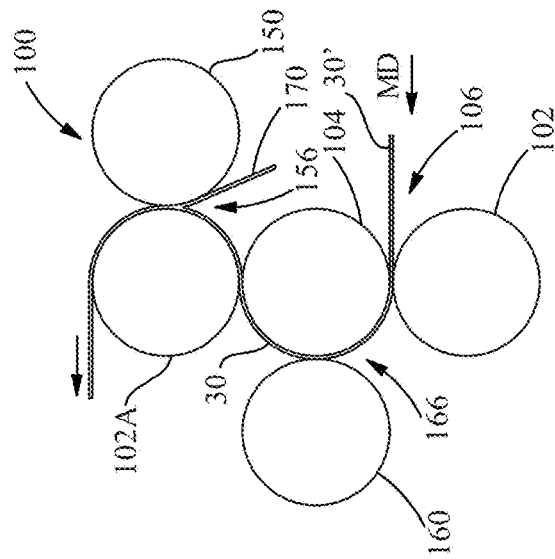
FIG. 42 is a schematic side view of an apparatus for deforming the nonwoven material which includes additional rolls for base bonding the deformed nonwoven material and then tip bonding the deformed nonwoven material to an additional layer.

FIG. 42 shows one embodiment of an apparatus 100 for carrying out a base bonding process in which the base bonded deformed nonwoven web 30 is then tip bonded to another material to form a composite web or sheet.

The rolls 102, 104, and 160 shown in FIG. 42 comprise the base bonding portion of the apparatus, which is similar to the apparatus shown in FIG. 32. FIG. 42 differs in that the precursor web 30' is shown as being fed into the deforming nip 106 from the right side, instead of the left side, and the deformed web 30 wraps partially around female roll 102 instead of bonding roll 160 after it leaves the deforming nip 106. Therefore, the description of this portion of the apparatus will incorporate the above description of the apparatus shown in FIG. 32, and will not be repeated in its entirety herein.

The apparatus shown in FIG. 42 further comprises a second male roll 102A and a tip bonding roll 150. The female roll 104, the second male roll 102A, and the tip bonding roll 150 comprise the tip bonding portion of the apparatus, which is similar to the apparatus shown in FIG. 30. FIG. 42 differs in that the deformed bonded web 30 is shown as wrapping around the second male roll 102A as it leaves the apparatus in FIG. 42, instead of wrapping around the tip bonding roll 150. Therefore, the description of this portion of the apparatus will incorporate the above description of the apparatus shown in FIG. 30, and will not be repeated in its entirety herein.

As shown in FIG. 42, the precursor web 30' is fed into the deforming nip 106 between first forming roll 102 and second forming roll 104. After leaving the deforming nip 106, the deformed web 30 is wrapped partially around the second forming roll, female roll 104. While the web 30 is still in contact with the female roll 104, it passes through a second nip 166 between female roll 104 and the additional bonding roll 160 for base bonding the deformed nonwoven material 30. The additional bonding roll 160 can compress the fibers in the undeformed first region 40 outside of the bases 50 of the protrusions 32 sufficient to partially melt and bond the fibers at this location together. This will provide the base bonded web with base bonds 168 which may be continuous similar to those shown in FIG. 33A, or discrete similar to those shown in FIG. 34. The deformed base bonded web 30 then passes between female roll 104 and second male roll 102A. After that, the deformed base bonded web 30 is wrapped partially around the second male roll 102A. While the web 30 is still in contact with the second male roll 102A, it passes through a second nip 156 between the second male roll 102A and the additional bonding roll 150.

Figure 31:
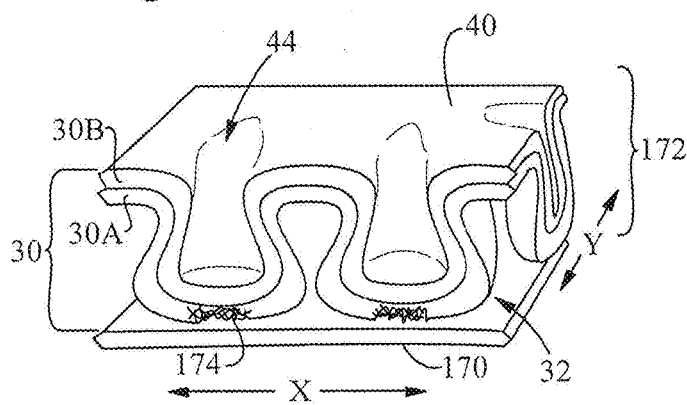
FIG. 31 is a schematic perspective view of a portion of a deformed nonwoven web protrusion tip bonded to an additional layer (only a portion of the additional layer is shown) made by the apparatus shown in FIG. 30.

At the second nip 156, an additional layer 170 is fed into the apparatus and is bonded to the deformed nonwoven material 30 at the tops (or distal ends 54) of the protrusions 32. This will form a composite web or sheet 172 similar to that shown in FIG. 31 comprising a base bonded deformed web 30 that is tip bonded to a second web 170.

V. Test Methods

A. Accelerated Compression Method.
1. Cut 10 samples of the specimen to be tested and 11 pieces of a paper towel into a 3 inch×3 inch (7.6 cm×7.6 cm) square.
2. Measure the caliper of each of the 10 specimens at 2.1 kPa and a dwell time of 2 seconds using a Thwing-Albert ProGage Thickness Tester or equivalent with a 50-60 millimeter diameter circular foot. Alternatively, a pressure of 0.5 kPa can be used. Record the pre-compression caliper to the nearest 0.01 mm.
3. Alternate the layers of the specimens to be tested with the pieces of paper towel, starting and ending with the paper towel. The choice of paper towel does not matter and is present to prevent "nesting" of the protrusions in the deformed samples. The samples should be oriented so the edges of each of the specimens and each of the paper towels are relatively aligned, and the protrusions in the specimens are all oriented the same direction.
4. Place the stack of samples into a 40±2° C. oven at 25±3% relative humidity and place a weight on top of the stack. The weight must be larger than the foot of the thickness tester. To simulate high pressures or low in-bag stack heights, apply 35 kPa (e.g. 17.5 kg weight over a 70×70 mm area). To simulate low pressures or high in-bag stack heights, apply 7.0 kPa (e.g. 3.4 kg weight over a 70×70 mm area), 4.0 kPa (e.g., 1.9 kg weight over a 70×70 mm area) of 1.0 kPa (e.g., 0.49 kg weight over a 70×70 mm area).
5. Leave the samples in the oven for 15 hours. After the time period has elapsed, remove the weight from the samples and remove the samples from the oven.
6. Within 30 minutes of removing the samples from the oven, measure the post-compression caliper as directed in step 2 above, making sure to maintain the same order in which the pre-compression caliper was recorded. Record the post-compression caliper of each of the 10 specimens to the nearest 0.01 mm.
7. Let the samples rest at 23±2° C. at 25±3% relative humidity for 24 hours without any weight on them.
8. After 24 hours, measure the post-recovery caliper of each of the 10 specimens as directed in step 2 above, making sure to maintain the same order in which the pre-compression and post-compression calipers were recorded. Record the post-recovery caliper of each of the 10 specimens to the nearest 0.01 mm. Calculate the amount of caliper recovery by subtracting the post-compression caliper from the post-recovery caliper and record to the nearest 0.01 mm.
9. If desired, an average of the 10 specimens can be calculated for the pre-compression, post-compression and post-recovery calipers.

B. Tensile Method

The MD and CD tensile properties are measured using World Strategic Partners (WSP) (harmonization of the two nonwovens organizations of INDA (North American based) and EDANA (Europe based)) Tensile Method 110.4 (05) Option B, with a 50 mm sample width, 60 mm gauge length, and 60 mm/min rate of extension. Note that the gauge length, rate of extension and resultant strain rate are from different from that specified within the method.

C. Surface Texture Characterization Method

The microscale surface texture of male elements is analyzed using a 3D Laser Scanning Confocal Microscope (suitable 3D Laser Scanning Confocal Microscope is the Keyence VK-X210, commercially available from Keyence Corporation of America, Itasca, Ill., USA). The microscope is interfaced with a computer running a measuring, control, and surface texture analysis software (suitable software is Keyence VK Viewer version 2.2.0.0 and Keyence VK Analyzer version 3.3.0.0, commercially available from Keyence Corporation of America, Itasca, Ill., USA).

The 3D surface Laser Scanning Confocal Microscope measures the surface heights of a specimen, and produces a map of surface height (z-directional or z-axis) versus displacement in the x-y plane. The surface map is then analyzed according to ISO 25178-2:2012, from which the areal surface texture parameters Sq, Sxp, Str and Vmp are calculated. These parameters describe key characteristics of the male element surface.

Using a 20× objective lens, a 1.0× zoom level and a 0.50 µm pitch (Z-step size), the microscope is programmed to collect a surface height image with a field of view of at least 500 µm×700 µm with an x-y pixel resolution of approximately 0.7 microns (μm)/pixel. If a larger field of view is required, multiple scans, maintaining the x-y resolution, over the surface can be collected and stitched together into a single image for analysis. The height resolution is set at 0.1 nm/digit, over a sufficient height range to capture all peaks and valleys within the field of view.

Calibrate the instrument according to the manufacturer's specifications.

Place the male element specimen on the stage beneath the objective lens. Collect a surface height image (z-direction) of the specimen by following the instrument manufacturer's recommended measurement procedures, which may include using the following settings to minimize noise and maximize the quality of the surface data: Real Peak Detection, single/double scan, surface profile mode, standard area, high-accuracy quality; laser intensity (Brightness and ND filter) set using auto gain. Save the surface height image.

Open the surface height image in the surface texture analysis software. ISO 25178-2:2012 describes a recommended filtration process, accordingly the following filtering procedure is performed on each image: 1) a Gaussian low pass S-filter with a nesting index (cut-off) of 2.5 μm; 2) an F-operation of plane tilt (auto) correction; and 3) a Gaussian high pass L-filter with a nesting index (cut-off) of 0.25 mm. Both Gaussian filters are run utilizing end effect correction. This filtering procedure produces the SL surface from which the areal surface texture parameters will be calculated.

Select the entire field of view for measurement, and calculate the areal surface roughness parameters on the SL Surface.

The surface texture parameters Sq, Sxp, Str and Vmp are described in ISO 25178-2:2012. Sq is the root mean square of the profile heights of the roughness surface. The units of Sq are μm. The parameters Sxp and Vmp are derived from the Areal Material Ratio (Abbott-Firestone) curve described in the ISO 13565-2:1996 standard extrapolated to surfaces, it is the cumulative curve of the surface height distribution histogram versus the range of surface heights. A material ratio is the ratio, given as a %, of the intersecting area of a plane passing through the surface at a given height to the cross sectional area of the evaluation region. The Peak Extreme Height, Sxp, is a measure of the difference in heights on the surface from the areal material ratio value of 2.5% (highest peaks, excluding outliers) to the areal material ratio value of 50% (the mean plane). The units of Sxp are μm. The Peak Material Volume, Vmp, is the actual volume of material comprising the surface from the height corresponding to a material ratio value of 10% to the highest peak (material ratio of 0%). The units of Vmp are mL/m$^2$. The Texture Aspect Ratio, Str, is a measure of the spatial isotropy or directionality of the surface texture. Str is a spatial parameter which involves the use of the mathematical technique of the autocorrelation function. The Str parameter has a value range between 0 and 1, and is unitless. An isotropic surface will have Str close to 1, while a strongly anisotropic surface will have Str close to 0. Str is calculated using a thresholding value of s=0.2. If a Str value is unable to be calculated, rotate the specimen by 30 degrees, rescan and reanalyze the surface.

Scan and analyze the surface textures of three replicate male elements. Average together the three Sq values and report to the nearest 0.01 μm. Average together the three Sxp values and report to the nearest 0.01 μm. Average together the three Vmp values and report to the nearest 0.01 mL/m$^2$. Average together the three Str values and report to the nearest 0.01 units.

D. Light Transmission.

The feature and land area light transmission method measures the average amount of light transmitted through specific regions of a specimen. A calibrated light transmission image is obtained using a flatbed scanner. A binary mask is generated using a corresponding surface topography image that is threshold at a given height to separate discrete feature regions from the surrounding land area. The binary mask is then registered to the light transmission image, and used to isolate the discrete features from the land area in the light transmission image. This enables the average light transmission value for each region to be calculated.

Sample Preparation—Topsheet/Underlying Layer Laminate

Tape the absorbent article to a rigid flat surface in a planar configuration with the body-facing surface up. Any leg elastics may be cut to facilitate laying the article flat. The entire topsheet/underlying layer (e.g. acquisition layer) laminate specimen is then carefully removed from the article. A scalpel and/or cryogenic spray (such as Cyto-Freeze, Control Company, Houston Tex. USA) can be used to remove the specimen from additional underlying layers, if necessary, to avoid any longitudinal and lateral extension of the specimen. The topsheet/underlying layer laminate specimen should be handled only with forceps around its peripheral edge. If the topsheet is not joined to an underlying layer, carefully remove only the topsheet layer as the specimen.

Identify a 40 mm×40 mm square region centered at, with the sides parallel to, the longitudinal and lateral centerlines of the specimen. Create registration marks on the specimen surface by using a black marker to make a small dot in the four corners of the identified 40 mm×40 mm square analysis region. Similarly, identify and mark a second and a third 40 mm×40 mm square analysis region. The second centered along the longitudinal centerline 50 mm inboard from the leading edge of the topsheet/underlying layer laminate, and the third centered along the longitudinal centerline 50 mm inboard from the trailing edge of the topsheet/underlying layer laminate. Depending on the length of the specimen the identified regions may overlap each other, if so, follow the procedure as described and analyze the entirety of each of the three regions. If the topsheet is not joined to an underlying layer, identify and mark the three 40 mm×40 mm analysis regions in like fashion, except use the leading and trailing edges of the topsheet to identify the location of the second and third analysis regions.

Five replicate topsheet/underlying layer laminate specimens are obtained from five substantially similar absorbent articles are similarly prepared for analysis. Precondition the specimens at about 23° C.±2 C.° and about 50%±2% relative humidity for 2 hours prior to testing.

Light Transmission Image

The color difference (delta E*) measurement is based on the CIE L* a* b* color system (CIELAB). A flatbed scanner capable of scanning a minimum of 24 bit color at 800 dpi and has manual control of color management (a suitable scanner is an Epson Perfection V750 Pro from Epson America Inc., Long Beach Calif. USA) is used to acquire images. The scanner is interfaced with a computer running color management software (suitable color management software is MonacoEZColor available from X-Rite Grand Rapids, Mich. USA). The scanner is calibrated against a color transparency target and corresponding reference file compliant with ANSI method IT8.7/1-1993 using the color management software to construct a calibrated color profile. The resulting calibrated scanner profile is used to color correct an image from a test specimen within an image analysis program that supports sampling in CIE L* a* b* (a suitable program is Photoshop S4 available from Adobe Systems Inc., San Jose, Calif. USA). All testing is performed in a conditioned room maintained at about 23±2° C. and about 50±2% relative humidity.

Turn on the scanner for 30 minutes prior to calibration. Deselect any automatic color correction or color management options that may be included in the scanner software. If the automatic color management cannot be disabled, the scanner is not appropriate for this application. Place the IT8 target face down onto the scanner glass, close the scanner lid, acquire an image at 200 dpi and 24 bit color and remove the IT8 target. Open the image file on the computer with the color management software. Follow the recommended steps within the color management software to create and export a calibrated color profile. These steps may include, ensuring that the scanned image is oriented and cropped correctly. The calibrated color profile must be compatible with the image analysis program. The color management software uses the acquired image to compare with the included reference file to create and export the calibrated color profile. After the profile is created the scan resolution (dpi) for test specimens can be changed, but all other settings must be kept constant while imaging specimens.

Open the scanner lid and place the specimen flat against the scanner glass with the skin facing surface facing the glass. Acquire and import a scan of the 40 mm×40 mm marked region of the specimen into the image analysis software at 24 bit color and at 800 dpi in transparency mode. Transparency mode illuminates the specimen from one side with the sensor capturing the image from the opposite side. Ensuring that each of the four registration marks are located in the corners of the scanned image. Assign the calibrated color profile to the image and change the color space mode to L*a*b* Color corresponding to the CIE L* a* b* standard. This produces a color corrected image for analysis. Save this color corrected image in an uncompressed format, such as a TIFF file.

Feature Area and Land Area Mask

The boundaries of the discrete feature areas and land area are identified by thresholding a 3D surface topography image at a specified height to generate a binary image, separating discrete feature areas from the surrounding land area. This binary image will then be used as a mask on the corresponding light transmission image to measure the average Light Transmission Values of the discrete feature areas separately from the average Light Transmission Values of the surrounding land area.

The 3D surface topography image is obtained using an optical 3D surface topography measurement system (a suitable optical 3D surface topography measurement system is the GFM MikroCAD Premium instrument commercially available from GFMesstechnik GmbH, Teltow/Berlin, Germany). The system includes the following main components: a) a Digital Light Processing (DLP) projector with direct digital controlled micro-mirrors; b) a CCD camera with at least a 1600×1200 pixel resolution; c) projection optics adapted to a measuring area of at least 60 mm×45 mm; d) recording optics adapted to a measuring area of 60 mm×45 mm; e) a table tripod based on a small hard stone plate; f) a blue LED light source; g) a measuring, control, and evaluation computer running surface topography analysis software (suitable software is ODSCAD software version 6.2 available from GFMesstechnik GmbH, Teltow/Berlin, Germany); and h) calibration plates for lateral (x-y) and vertical (z) calibration available from the vendor.

The optical 3D surface topography measurement system measures the surface height of a specimen using the digital micro-mirror pattern fringe projection technique. The result of the analysis is a map of surface height (z-directional or z-axis) versus displacement in the x-y plane. The system has a field of view of 60×45 mm with an x-y pixel resolution of approximately 40 microns. The height resolution is set at 0.5 micron/count, with a height range of +/−15 mm. All testing is performed in a conditioned room maintained at about 23±2° C. and about 50±2% relative humidity.

Calibrate the instrument according to manufacturer's specifications using the calibration plates for lateral (x-y axis) and vertical (z axis) available from the vendor.

Place specimen on the table beneath the camera. Center the marked 40 mm×40 mm analysis region of the specimen within the camera field of view, so that only the specimen surface is visible in the image. Place a steel frame (100 mm square, 1.5 mm thick with an opening 70 mm square) on the sample to ensure the specimen lays flat with minimal wrinkles, and still allows for an unobstructed access to the surface area being scanned.

Collect a height image (Z-direction) of the specimen by following the instrument manufacturer's recommended measurement procedures, which may include, focusing the measurement system and performing a brightness adjustment. No pre-filtering options should be utilized. Save the collected height image file.

Load the height image into the surface analysis portion of the software. The following filtering procedure is then performed on each image: 1) remove invalid points; 2) a 3×3 pixel median filter to remove noise; 4) an automatic planar alignment to remove form; and 3) a Gaussian high pass filter with a cut-off wavelength of 10 mm to filter out large scale waviness in the sample. Crop the image to the 40 mm×40 mm square area identified by the registration marks, so that each of the four registration marks are located in the four corners of the cropped image.

Determination of the thresholding height level utilizes the Areal Material Ratio (Abbott-Firestone) curve, described in the ISO 13565-2:1996 standard extrapolated to surfaces. It is the cumulative curve of the surface height distribution histogram versus the range of surface heights. A material ratio is the ratio, given as a %, of the intersecting area of a plane passing through the surface at a given height (cutting depth) to the cross sectional area of the evaluation region. If the specimen contains discrete features which are depressions oriented downward relative to the body facing surface or contains apertures, threshold the surface topography image at a cutting depth where the material ratio is 75%. A material ratio of 75% separates the deep valleys from the land area region. If the specimen contains discrete features which are protrusions or tufts oriented upward, threshold the surface topography image at a cutting depth where the material ratio is 25%. A material ratio of 25% separates the protruding peaks from the land area region. By thresholding at the levels described above, a binary mask image is produced with the discrete feature areas assigned one value, and the surrounding land area assigned a different value. For example, the discrete feature areas could appear black, and the surrounding land area could appear white. Save this binary mask image in an uncompressed format, such as a TIFF file.

Analysis of Light Transmission Image

Open both the color corrected light transmission image and the corresponding binary mask image in the image analysis software. To analyze the specimen light transmission image, first separate the L*, a* and b* channels, and select only the L* channel for analysis. The L* channel represents the "Lightness" of the image and has values that range from 0-100. Register the light transmission image and the binary mask image to each other so that the corresponding registration marks are aligned. Use the mask to remove the land area from the light transmission image, and calculate the average L* value (Light Transmission Value) for the remaining discrete features. Record this value as the Feature Light Transmission Value to the nearest 0.1 units. Then use the binary mask to remove the discrete features from the light transmission image, and calculate an average L* value (Light Transmission Value) for the remaining surrounding land area. Record this value as the Land Area Light Transmission Value to the nearest 0.1 units. Repeat this procedure for the other two regions on the specimen. Calculate the difference between the Feature Light Transmission Value and the Land Area Light Transmission Value for each of the three analyzed regions on a single specimen. Compare the three differences and keep the Feature Light Transmission Value and Land Area Light Transmission Value from the 40 mm×40 mm analysis region with the highest difference and discard the values from the other two regions. In like fashion repeat this procedure on all of the replicate specimens. Calculate and report the average of the five individual Feature Light Transmission Values and Land Area Light Transmission Values to the nearest 0.1 units.

VI. Examples

Comparative Example 1

In Comparative Example 1, the material is a composite of two materials glued together using H.B. Fuller of St. Paul, Minn., U.S.A. D3166ZP hot melt adhesive applied in a spiral pattern at a 1 gsm add on level. The composite material is processed through a nip formed by one of The Procter & Gamble Company's SELF rolls and a ring roll as described in U.S. Pat. No. 7,410,683 B2, Curro, et al., at 25 feet/minute (fpm) (7.6 meters per minute) and 0.135" (3.43 mm) DOE. The material layer in contact with the SELF roll is a 20 gsm spunbond nonwoven produced by Fitesa of Simpsonville, S.C., U.S.A. Such a material is described in Fitesa's U.S. patent application Ser. No. 14/206,699 entitled "Extensible Nonwoven Fabric" and is comprised of 2.5 denier fibers comprising a blend of PP and PE The material layer in contact with the ring roll is a 43 gsm spunbond nonwoven produced by Reicofil of Troisdorf, Germany, comprised of 7 denier co-PET/PET tipped-trilobal bicomponent fibers.

Example 1. Single Layer

In Example 1, the material is a 50 grams/m² (gsm) PE/PP sheath/core bicomponent spunbond nonwoven from Fitesa. It is processed at 25 fpm (7.6 meters per minute) speed at 0.155 inch (3.94 mm) depth of engagement (DOE) through male/female tooling (forming members). The teeth on the male tool have a rounded diamond shape like that shown in FIG. 21, with vertical sidewalls and a radiused or rounded edge at the transition between the top and the sidewalls of the male element. The teeth are 0.186 inch (4.72 mm) long and 0.125 inch (3.18 mm) wide with a CD spacing of 0.150 inch (3.81 mm) and an MD spacing of 0.346 inch (8.79 mm). The recesses in the mating female roll also have a rounded diamond shape, similar to that of the male roll, with a clearance between the rolls of 0.032-0.063 inch (0.813-1.6 mm), varying slightly around the perimeter of the recess.

Example 2. Two Layers

In Example 2, the material is a composite of two materials glued together using the same hot melt adhesive applied in a spiral pattern as described in Comparative Example 1. It is processed through the male/female tooling described in Example 1, at 800 feet per minute (fpm) (24.4 meters per minute) and 0.155 inch (3.94 mm) DOE. The material layer in contact with the male roll is the 20 gsm spunbond nonwoven produced by Fitesa comprised of 2.5 denier fibers with a blend of PP and PE described in Comparative Example 1. The material layer in contact with the female roll is a 60 gsm through-air bonded carded nonwoven produced by Beijing Dayuan Non-Woven Fabric Co, LTD of Beijing, China, comprised of 5 denier PE/PET sheath/core bicomponent fibers.

Example 3. Two Layers

In Example 3, the material is a composite of two materials glued together using the same hot melt adhesive applied in a spiral pattern as described in Comparative Example 1. It is processed through the male/female tooling described in Example 1, at 800 fpm and 0.155 inch (3.94 mm) DOE. The material layer in contact with the male roll is a 20 gsm spunbond nonwoven produced by Fitesa comprised of 2.5 denier fibers with a blend of PP and PE described in Example 2. The material layer in contact with the female roll is an 86 gsm spunbond nonwoven produced by Reicofil comprised of 7 denier co-PET/PET tipped-trilobal bicomponent fibers.

The samples are compressed for 15 hours according to the Accelerated Compression Method, with a 3.4 kg weight (7 kPa). The pre-compression caliper and the post-compression caliper of the samples are measured following the Accelerated Compression Method under 2.1 kPa pressure. The dimensions of the protrusions and openings are measured using a microscope at 20× magnification. The exterior dimensions of the cap are measured from a perspective view with the protrusions facing up, like that shown in FIG. 5. The protrusion depth and the interior cap width is measured from the cross-section of the material like that shown in FIG. 11.

TABLE 2

Material Examples

| Example | First Layer (Contacts Male Tool) | Second Layer (Contacts Female Tool) | Measured Before or After Compression | Caliper at 2.1 kPa (7 kPa) (mm) | Protrusion Depth (mm) | Base Opening Width ($W_0$) (mm) | Base Opening Length (mm) | Cap Width-Interior ($W_I$) (mm) | Cap Width-Exterior (mm) | Cap Length-Exterior (mm) | Ratio of Cap width-Interior to Base Opening Width |
|---|---|---|---|---|---|---|---|---|---|---|---|
| Comp. Ex. 1 | 20 gsm Spunbond PE/PP Blend | 43 gsm co-PET/PET Spunbond | Before Compression | 1.2 | 1.1 (Tuft) | 0.5 | 4.7 | <0.1* (Tuft) | 1.5 (Tuft) | 4.6 (Tuft) | — |
| | | | After Compression | 0.7 | 0.3 | 0* (opening was closed) | 4.7 | 0* (opening was closed) | 0.7 | 4.0 | — |

TABLE 2-continued

Material Examples

| Example | First Layer (Contacts Male Tool) | Second Layer (Contacts Female Tool) | Measured Before or After Compression | Caliper at 2.1 kPa (7 kPa) (mm) | Protrusion Depth (mm) | Base Opening Width ($W_O$) (mm) | Base Opening Length (mm) | Cap Width-Interior ($W_I$) (mm) | Cap Width-Exterior (mm) | Cap Length-Exterior (mm) | Ratio of Cap width-Interior to Base Opening Width |
|---|---|---|---|---|---|---|---|---|---|---|---|
| Ex. 1 | 50 gsm PE/PP Bico Spunbond | None | Before Compression | 0.48 | 1.3 | 1.5 | 3.3 | 1.7 | 2.4 | 4.2 | 1.1 |
|  |  |  | After Compression | 0.39 | 0.4 | 1.7 | 3.0 | 2.1 | 2.9 | 4.3 | 1.2 |
| Ex. 2 | 20 gsm Spunbond PE/PP Blend | 60 gsm PET Carded Through-air Bonded | Before Compression | 1.6 | 1.9 | 1.9 | 3.5 | 2.4 | 3.2 | 4.5 | 1.3 |
|  |  |  | After Compression | 0.88 | 0.5 | 1.6 | 3.3 | 1.8 | 2.7 | 4.4 | 1.1 |
| Ex. 3 | 20 gsm Spunbond PE/PP Blend | 86 gsm co-PET/PET Spunbond | Before Compression | 2.0 | 1.9 | 1.8 | 3.8 | 2.2 | 3.8 | 4.8 | 1.2 |
|  |  |  | After Compression | 1.3 | 0.7 | 1.5 | 3.6 | 2.5 | 3.7 | 5.2 | 1.7 |

*Difficult to measure because measurement was so small

Example 4—Light Transmission Differences

FIGS. 37-40 show images of several nonwoven topsheets that have been formed by different processes. Each has discrete features that are formed into the materials.

Figure 37:
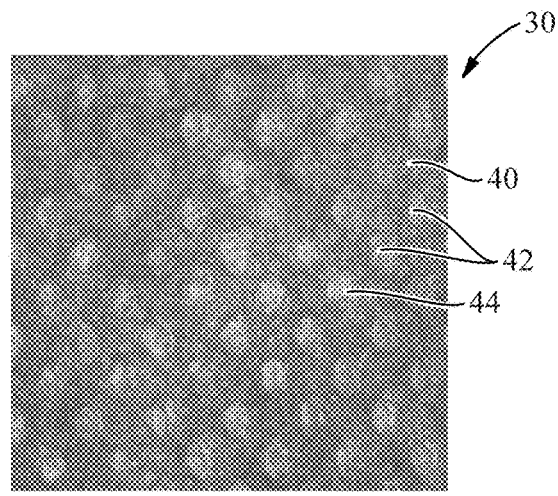
FIG. 37 is a plan view photograph of a nonwoven material as described herein with the base openings oriented upward.

FIG. 37 shows a nonwoven material 30 as described herein shown with the base openings 44 facing upward (which appear as depressions). The nonwoven material 30 comprises two layers that are joined together to form a topsheet and underlying acquisition layer. The layers comprise a 25 gsm polyethylene/polypropylene bicomponent fiber topsheet layer and a 43 gsm spunbond PET acquisition layer, glued together with 1 gsm spiral glue pattern that have been run through the deformation process described herein. The nonwoven material 30 comprises a generally planar first region 40 and a plurality of discrete integral second regions 42 that comprise spaced apart deformations (the depressions) in the nonwoven material. The first region 40 may form a continuous inter-connected network region wherein portions of the network surround each of the (depressions) deformations.

Figure 38:
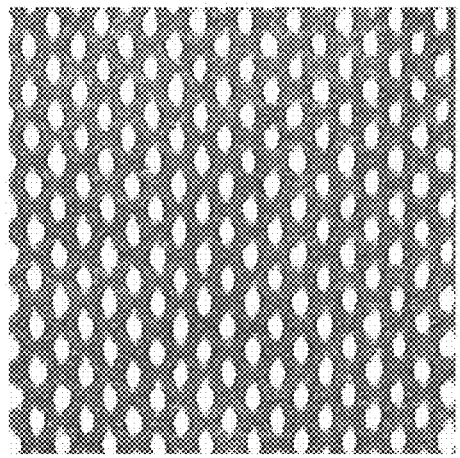
FIG. 38 is a plan view photograph of an apertured nonwoven material.

The first region 40 has a first light transmission value and the second regions 42 have a second transmission value. The light transmission values are summarized in Table 3 below. The second light transmission value in the deformations is at least about 5 units greater, alternatively at least about 9 units, alternatively about 10 units greater, than the first light transmission value. In this example, the fibers are not densified or melted together, which could also result in a higher light transmission value. The method of making the nonwoven web described herein creates that difference by rearranging the fibers in the web, resulting in a lower fiber concentration, and therefore a higher light transmission value, in the bottom of the depressions. The deformations/second regions 42 have a light transmission of less than or equal to about 90 units, indicating the absence of a through-hole in the bottom of the deformations. (For comparison, FIG. 38 is a photograph of an apertured nonwoven material. An aperture that is substantially clear of fibers has a light transmission value of between 95-100 units).

The nonwoven material 30 described herein is unique in that (like the topsheet shown in FIG. 38) it creates the "look" of an aperture that has depth, making it appear absorbent and dry, but without some of the softness negatives (technical and perceptual) associated with some apertures. Due to the increase in translucency in the deformation, placing a colored layer behind the nonwoven material 30 could result in color showing through primarily in the depression, highlighting the depression and, in some cases, making it appear to have even more depth.

Figure 39:
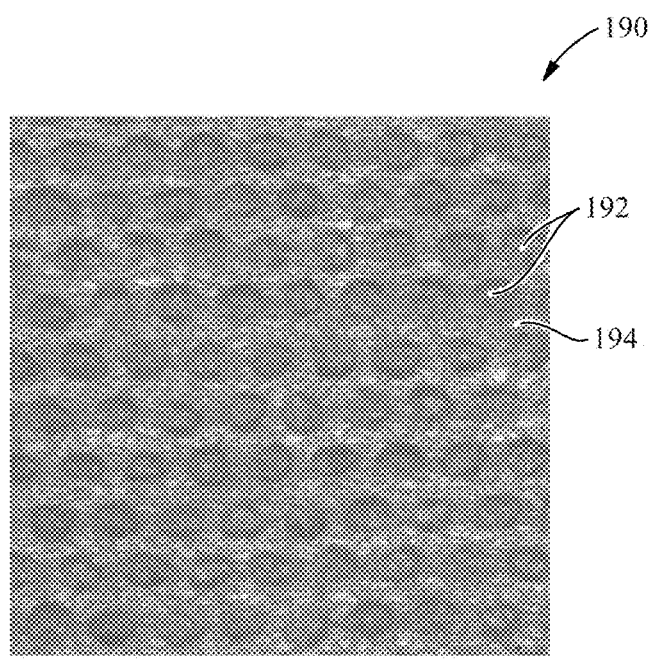
FIG. 39 is a plan view photograph of a currently marketed topsheet.

FIG. 39 is a photograph of a currently marketed Kimberly-Clark HUGGIES® diaper topsheet 190 which has discrete portions or tufts 192 oriented upward. In this example, the light transmission value in the discrete portions 192 is in the opposite relationship to that of the nonwoven material in FIG. 37. The light transmission value in the discrete portions 192 is at least about 5 units lower, and more typically is at least about 7 units lower, than the light transmission value in the continuous land region 194.

TABLE 3

Light Transmission Value

| Samples | Discrete Feature | Feature Mean | Feature Std Dev | Land Area Mean | Land Area Std Dev | Delta (Feature Minus Land) Mean |
|---|---|---|---|---|---|---|
| Example 4 | Depression | 65.5 | 8.7 | 56.5 | 7.2 | 9.0 |
| HUGGIES ® | Tuft | 51.9 | 5.5 | 59.3 | 7.9 | −7.4 |
| Apertured topsheet | Aperture | 97.8 | 0.16 | 60.8 | 9.0 | 37.0 |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "90°" is intended to mean "about 90°".

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A composite sheet comprising a first sheet and a second sheet which are partially bonded to each other at a number of spaced apart discrete inter-sheet bond locations, the composite sheet comprising:
   the first sheet, which comprises a nonwoven web having a plurality of fibers, the nonwoven web comprising:
      a first surface,
      a second surface,
      a generally planar first region having a X-direction orientation, a Y-direction orientation, and
      a plurality of discrete integral second regions that comprise deformations,
   wherein the first region is in the form of a continuous interconnected network which comprises portions that surround each of the deformations, and the deformations form protrusions of the fibers extending outward from the first surface of the nonwoven web, and openings formed in the second surface, wherein each of the protrusions comprises:
      a base proximate to the first surface, an opposed distal end extending outward from the base, and walls of the fibers between the base and the distal end, a base opening having a base opening width of 0.5 mm to 4 mm, and
      a cap comprising at least a portion of the walls and the distal end, the cap having a portion with a maximum interior width,
   wherein a ratio of the maximum interior width of the cap to the base opening width is about 1.1, about 1.2, or about 1.7, after compression; and
   the second sheet, which is generally planar and contacting the first region of the first sheet, the second sheet being bonded to the first sheet at a number of spaced apart discrete inter-sheet bond locations, wherein the inter-sheet bond locations are disposed outside the deformations on the first sheet at locations where the first region of the first sheet contacts the second sheet, and the inter-sheet bond locations are spaced apart in the X-direction and the Y-direction.

2. The composite sheet of claim 1 wherein the first sheet comprises at least two layers and both layers have deformations formed therein.

3. The composite sheet of claim 2 wherein at least one of the layers is a spunbond nonwoven which has discrete bond sites therein.

4. The composite sheet of claim 1 wherein the protrusions in the first sheet have a bulbous configuration.

5. The composite sheet of claim 1 wherein the first region of the first sheet has a first fiber concentration, the distal ends of the protrusions have a second fiber concentration, and the side walls of the protrusions have a third fiber concentration, wherein the first fiber concentration is greater than the third fiber concentration.

6. The composite sheet of claim 5 wherein at least the portion of the first sheet at locations are disposed outside the deformations on the first sheet at locations where the first region of the first sheet contacts the second sheet contribute to form the inter-sheet bond locations comprise base bonded portions, and the base bonded portions have fibers that are more densely packed than the fibers in the first region.

7. The composite sheet of claim 1 wherein in the case of at least some of the deformations in the first sheet, the inter-sheet bonds are located in at least two discrete portions of the first region outside of the deformations.

8. The composite sheet of claim 1 wherein in the case of at least some of the deformations in the first sheet, the inter-sheet bonds substantially surround the deformations.

9. The composite sheet of claim 1 wherein the first sheet is made from a precursor nonwoven web which is capable of undergoing an apparent elongation of greater than or equal to about 110%.

10. The composite sheet of claim 1 wherein when compressive forces of 7 kPa are applied on the first sheet perpendicular to the plane of the first region in accordance with the Accelerated Compression Method, at least some of the protrusions are configured to collapse in a controlled manner such that the base opening remains open, and the width of the base opening is greater than about 0.5 mm after compression.

11. The composite sheet of claim 10 wherein when the at least some protrusions collapse in a controlled manner, the side walls of such protrusions on at least one side form a z-folded structure.

12. The composite sheet of claim 1 wherein the first sheet comprises at least two layers that are joined together, the two layers comprising a first layer and a second layer, wherein a portion of the second layer is positioned inside a portion of the first layer in the protrusions, and wherein the fibers in the first layer are shorter in length than the fibers in the second layer.

13. The composite sheet of claim 12 wherein the fibers in the first layer are discontinuous and the fibers in the second layer are continuous.

14. The composite sheet of claim 1 wherein the first sheet comprises at least two nonwoven layers that are joined together, the two layers comprising a first layer and a second layer each layer comprising fibers, wherein the second layer also comprises a first surface, a second surface, a first region, and deformations forming protrusions extending outward from the first surface of the second layer, and openings formed in the second surface of the second layer, the protrusions being comprised of the fibers, wherein the protrusions comprise a base proximate the first surface of the second layer, an opposed distal end extending outward from the base, and side walls between the base and the distal end of the protrusion, wherein:
   a) the concentration of fibers in the first region of the first layer is greater than the concentration of fibers in the distal ends of the protrusions in the first layer; and
   b) the concentration of fibers in the second layer in the first region and the distal ends of the protrusions is greater than the concentration of fibers in the side walls of the protrusions in the second layer.

15. A composite sheet comprising a first sheet and a second sheet which are partially bonded to each other at a number of spaced apart discrete inter-sheet bond locations, the composite sheet comprising:
the first sheet, which comprises a nonwoven web having a plurality of fibers, the nonwoven web comprising:
a first surface,
a second surface,
a generally planar first region having a X-direction orientation, a Y-direction orientation, and
a plurality of discrete integral second regions that comprise deformations,
wherein the first region is in the form of a continuous interconnected network which comprises portions that surround each of the deformations, and the deformations form protrusions of the fibers extending outward from the first surface of the nonwoven web, and openings formed in the second surface, wherein each of the protrusions comprises:
a base proximate to the first surface, an opposed distal end extending outward from the base, and walls of the fibers between the base and the distal end, a base opening having a base opening width of 0.5 mm to 4 mm, and
a cap comprising at least a portion of the walls and the distal end, the cap having a portion with a maximum interior width,
wherein a ratio of the maximum interior width of the cap to the base opening width is from 1.1 to 1.3, before compression; and the second sheet, which is generally planar and contacting the first region of the first sheet, the second sheet being bonded to the first sheet at a number of spaced apart discrete inter-sheet bond locations, wherein the inter-sheet bond locations are disposed outside the deformations on the first sheet at locations where the first region of the first sheet contacts the second sheet, and the inter-sheet bond locations are spaced apart in the X-direction and the Y-direction.

16. The composite sheet of claim 15 wherein the first sheet comprises at least two layers and both layers have deformations formed therein.

17. The composite sheet of claim 16 wherein at least one of the layers is a spunbond nonwoven which has discrete bond sites therein.

18. The composite sheet of claim 15 wherein the protrusions in the first sheet have a bulbous configuration, wherein the first region of the first sheet has a first fiber concentration, the distal ends of the protrusions have a second fiber concentration, and the side walls of the protrusions have a third fiber concentration, wherein the first fiber concentration is greater than the third fiber concentration.

* * * * *